(12) United States Patent
Artof et al.

(10) Patent No.: US 7,101,396 B2
(45) Date of Patent: Sep. 5, 2006

(54) MINIMALLY INVASIVE VALVE REPLACEMENT SYSTEM

(75) Inventors: Jason Artof, Huntington Beach, CA (US); Tuoc Tan Nguyen, Irvine, CA (US); Keith E. Myers, Lake Forest, CA (US)

(73) Assignee: 3F Therapeutics, Inc., Lake Forest, CA (US)

( * ) Notice: Subject to any disclaimer, the term of this patent is extended or adjusted under 35 U.S.C. 154(b) by 53 days.

(21) Appl. No.: 10/680,071

(22) Filed: Oct. 6, 2003

(65) Prior Publication Data

US 2005/0075731 A1    Apr. 7, 2005

(51) Int. Cl.
*A61F 2/24*    (2006.01)

(52) U.S. Cl. .................... 623/2.18; 623/2.14

(58) Field of Classification Search ............... 623/1.24, 623/1.26, 2.11–2.19, 900
See application file for complete search history.

(56) References Cited

U.S. PATENT DOCUMENTS

| | | | |
|---|---|---|---|
| 3,657,744 A | 4/1972 | Ersek | |
| 3,714,671 A | 2/1973 | Edwards | |
| 4,680,031 A | 7/1987 | Alonso | |
| 5,411,552 A | 5/1995 | Andersen | |
| 5,500,014 A | 3/1996 | Quijano | |
| 5,840,081 A | 11/1998 | Andersen | |
| 5,855,601 A | 1/1999 | Bessler | |
| 5,957,949 A * | 9/1999 | Leonhardt et al. | 623/1.24 |
| 6,168,614 B1 | 1/2001 | Andersen | |
| 6,245,102 B1 * | 6/2001 | Jayaraman | 623/1.15 |
| 6,425,916 B1 | 7/2002 | Garrison | |
| 6,454,799 B1 | 9/2002 | Schreck | |
| 6,494,909 B1 | 12/2002 | Greenhalgh | |
| 6,503,272 B1 | 1/2003 | Duerig | |
| 6,530,952 B1 | 3/2003 | Vesely | |
| 6,558,417 B1 * | 5/2003 | Peredo | 623/2.13 |
| 6,558,418 B1 | 5/2003 | Carpentier | |
| 6,582,462 B1 | 6/2003 | Andersen | |
| 6,682,559 B1 | 1/2004 | Myers | |
| 6,730,118 B1 | 5/2004 | Spenser | |
| 6,733,525 B1 | 5/2004 | Yang | |
| 6,767,362 B1 | 7/2004 | Schreck | |
| 2001/0007956 A1 | 7/2001 | Letac | |
| 2001/0011017 A1 | 8/2001 | Letac | |
| 2001/0039450 A1 * | 11/2001 | Pavcnik et al. | 623/1.24 |
| 2002/0052651 A1 * | 5/2002 | Myers et al. | 623/2.15 |
| 2002/0099439 A1 * | 7/2002 | Schwartz et al. | 623/1.24 |
| 2002/1051970 | 10/2002 | Garrison | |
| 2003/0014104 A1 | 1/2003 | Cribier | |
| 2003/0040792 A1 | 2/2003 | Gabbay | |
| 2003/0060875 A1 | 3/2003 | Wittens | |
| 2003/0109924 A1 | 6/2003 | Cribier | |
| 2003/0130729 A1 | 7/2003 | Paniagua | |
| 2003/0153974 A1 | 8/2003 | Spenser | |
| 2003/0199971 A1 * | 10/2003 | Tower et al. | 623/1.24 |
| 2004/0019374 A1 * | 1/2004 | Hojeibane et al. | 623/1.13 |

(Continued)

Primary Examiner—Bruce Snow
Assistant Examiner—Cheryl Miller
(74) Attorney, Agent, or Firm—Jones Day

(57) ABSTRACT

Methods and systems for minimally invasive replacement of a valve. The system includes a collapsible valve and anchoring structure, devices and methods for expanding the valve anchoring structure, adhesive means to seal the valve to the surrounding tissue, a catheter-based valve sizing and delivery system, native valve removal means, and a temporary valve and filter assembly to facilitate removal of debris material. The valve assembly comprises a valve and anchoring structure for the valve, dimensioned to fit substantially within the valve sinus.

17 Claims, 43 Drawing Sheets

U.S. PATENT DOCUMENTS

2004/0210306 A1* 10/2004 Quijano et al. ............ 623/2.17
2004/0260389 A1* 12/2004 Case et al. ................. 623/1.24
2005/0240262 A1* 10/2005 White ....................... 623/2.12

* cited by examiner

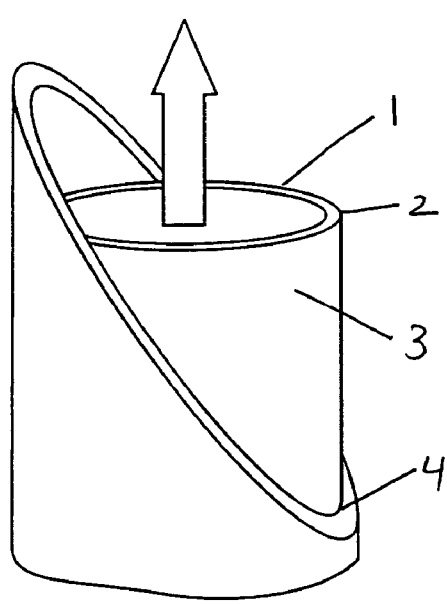
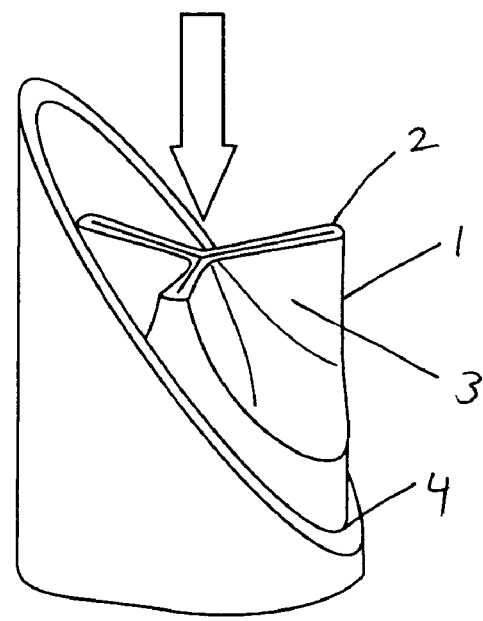
FIG. 1A    FIG. 1B
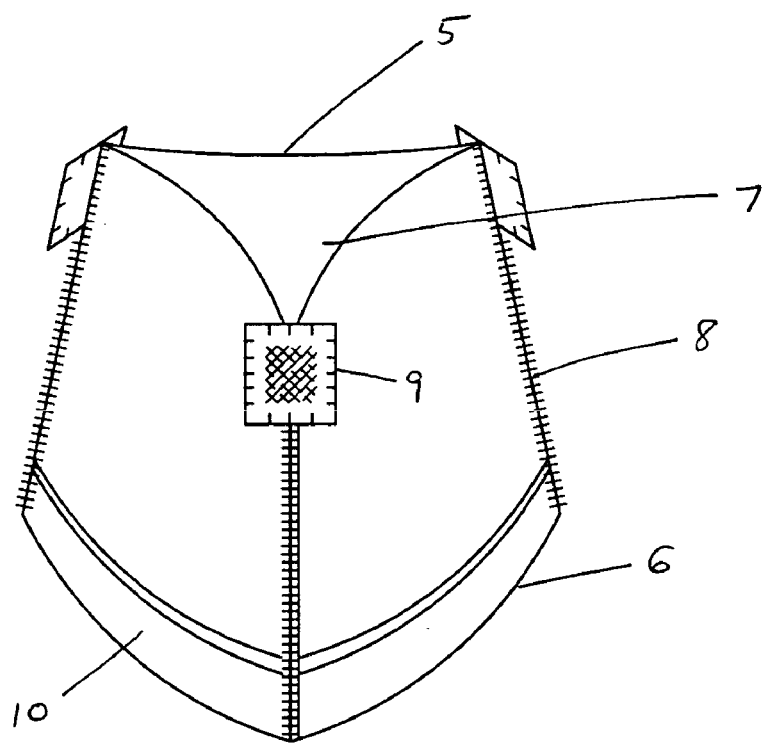
FIG. 2

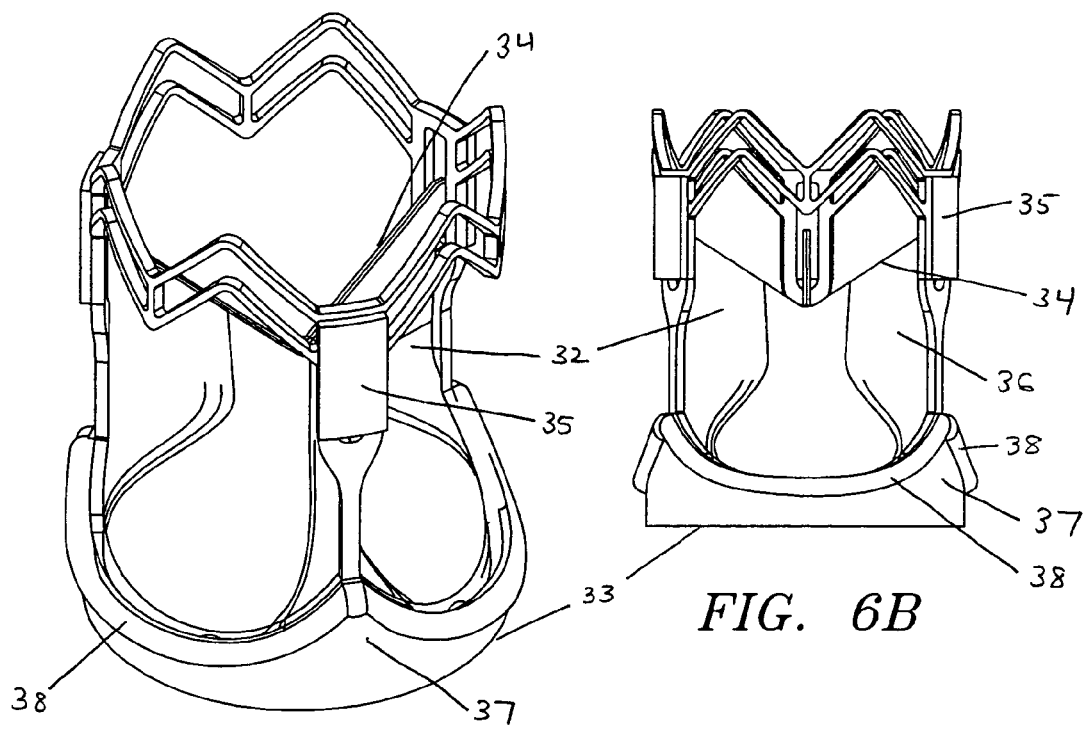
FIG. 6A
FIG. 6B
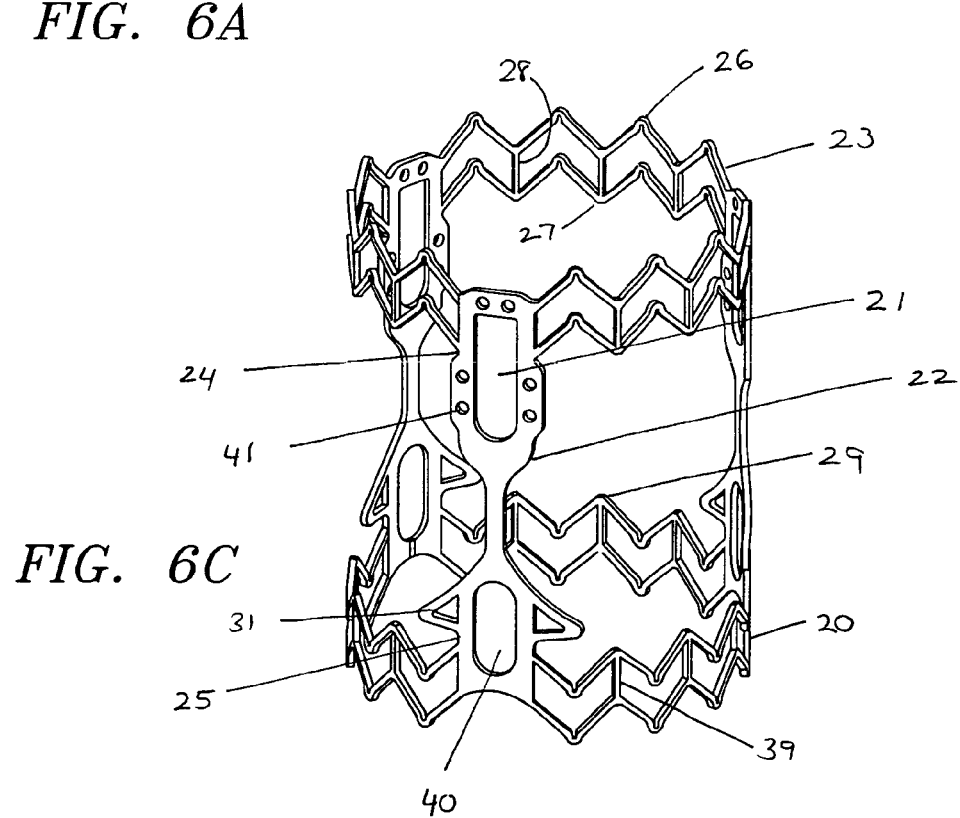
FIG. 6C

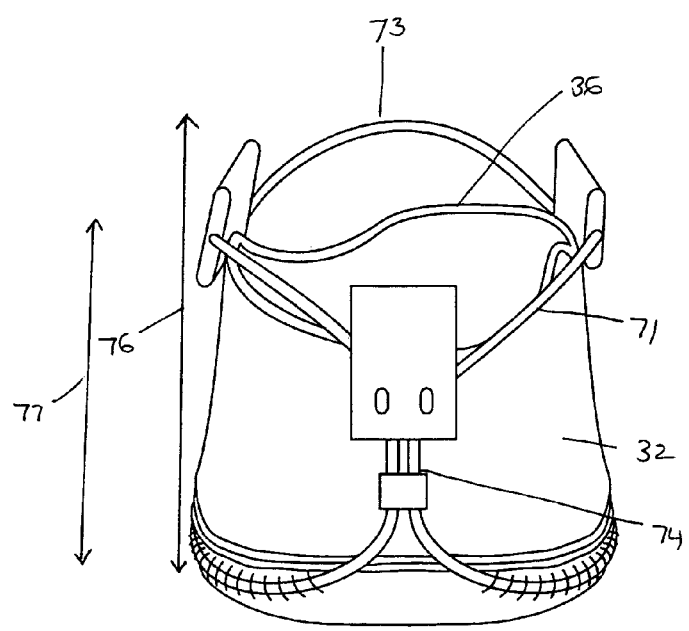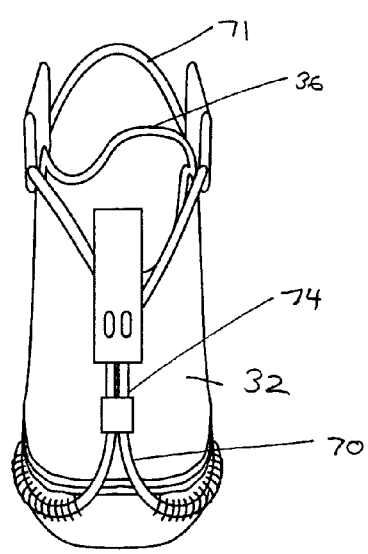
*FIG.16A*    *FIG.16B*

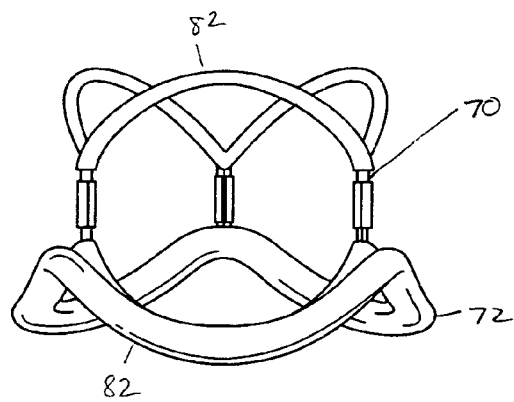
FIG. 21A
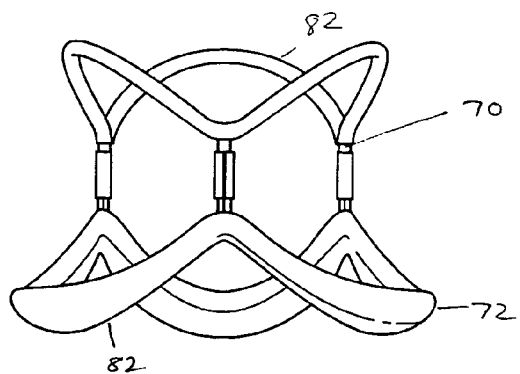
FIG. 21B
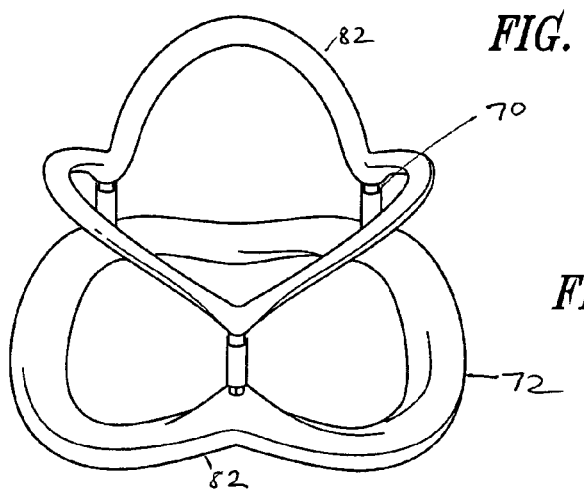
FIG. 21C
FIG. 21D
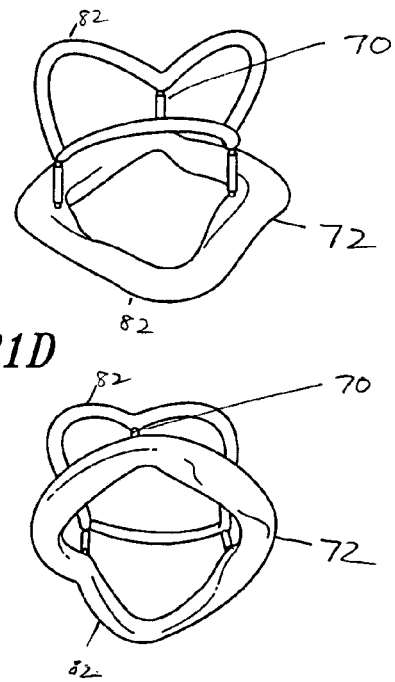
FIG. 21E
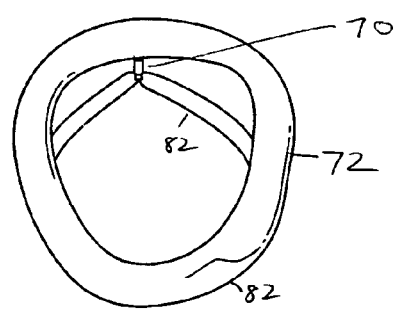
FIG. 21F
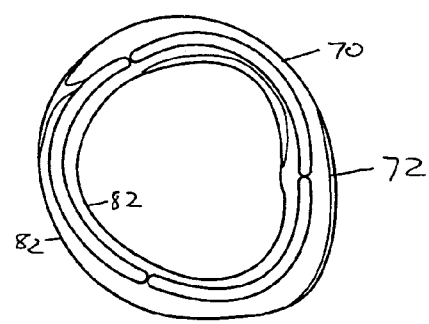
FIG. 21G

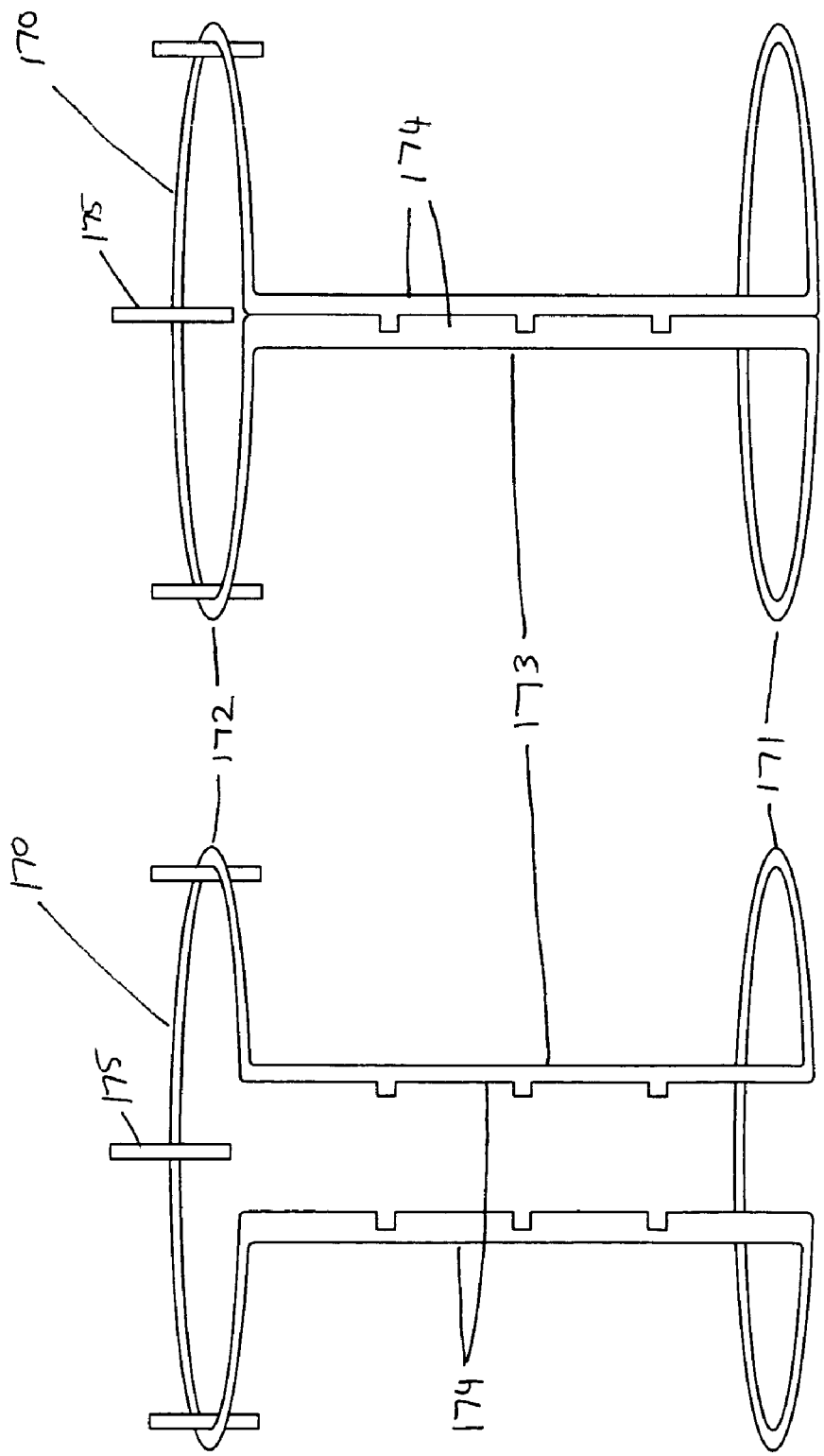

MINIMALLY INVASIVE VALVE REPLACEMENT SYSTEM

FIELD OF THE INVENTION

The present invention relates to devices and systems for the replacement of physiological valves.

BACKGROUND OF THE INVENTION

The transport of vital fluids in the human body is largely regulated by valves. Physiological valves are designed to prevent the backflow of bodily fluids, such as blood, lymph, urine, bile, etc., thereby keeping the body's fluid dynamics unidirectional for proper homeostasis. For example, venous valves maintain the upward flow of blood, particularly from the lower extremities, back toward the heart, while lymphatic valves prevent the backflow of lymph within the lymph vessels, particularly those of the limbs.

Because of their common function, valves share certain anatomical features despite variations in relative size. The cardiac valves are among the largest valves in the body with diameters that may exceed 30 mm, while valves of the smaller veins may have diameters no larger than a fraction of a millimeter. Regardless of their size, however, many physiological valves are situated in specialized anatomical structures known as sinuses. Valve sinuses can be described as dilations or bulges in the vessel wall that houses the valve. The geometry of the sinus has a function in the operation and fluid dynamics of the valve. One function is to guide fluid flow so as to create eddy currents that prevent the valve leaflets from adhering to the wall of the vessel at the peak of flow velocity, such as during systole. Another function of the sinus geometry is to generate currents that facilitate the precise closing of the leaflets at the beginning of backflow pressure. The sinus geometry is also important in reducing the stress exerted by differential fluid flow pressure on the valve leaflets or cusps as they open and close.

Thus, for example, the eddy currents occurring within the sinuses of Valsalva in the natural aortic root have been shown to be important in creating smooth, gradual and gentle closure of the aortic valve at the end of systole. Blood is permitted to travel along the curved contour of the sinus and onto the valve leaflets to effect their closure, thereby reducing the pressure that would otherwise be exerted by direct fluid flow onto the valve leaflets. The sinuses of Valsalva also contain the coronary ostia, which are outflow openings of the arteries that feed the heart muscle. When valve sinuses contain such outflow openings, they serve the additional purpose of providing blood flow to such vessels throughout the cardiac cycle.

When valves exhibit abnormal anatomy and function as a result of valve disease or injury, the unidirectional flow of the physiological fluid they are designed to regulate is disrupted, resulting in increased hydrostatic pressure. For example, venous valvular dysfunction leads to blood flowing back and pooling in the lower legs, resulting in pain, swelling and edema, changes in skin color, and skin ulcerations that can be extremely difficult to treat. Lymphatic valve insufficiency can result in lymphedema with tissue fibrosis and gross distention of the affected body part. Cardiac valvular disease may lead to pulmonary hypertension and edema, atrial fibrillation, and right heart failure in the case of mitral and tricuspid valve stenosis; or pulmonary congestion, left ventricular contractile impairment and congestive heart failure in the case of mitral regurgitation and aortic stenosis. Regardless of their etiology, all valvular diseases result in either stenosis, in which the valve does not open properly, impeding fluid flow across it and causing a rise in fluid pressure, or insufficiency/regurgitation, in which the valve does not close properly and the fluid leaks back across the valve, creating backflow. Some valves are afflicted with both stenosis and insufficiency, in which case the valve neither opens fully nor closes completely.

Because of the potential severity of the clinical consequences of valve disease, valve replacement surgery is becoming a widely used medical procedure, described and illustrated in numerous books and articles. When replacement of a valve is necessary, the diseased or abnormal valve is typically cut out and replaced with either a mechanical or tissue valve. A conventional heart valve replacement surgery involves accessing the heart in a patient's thoracic cavity through a longitudinal incision in the chest. For example, a median sternotomy requires cutting through the sternum and forcing the two opposite halves of the rib cage to be spread apart, allowing access to the thoracic cavity and the heart within. The patient is then placed on cardiopulmonary bypass, which involves stopping the heart to permit access to the internal chambers. Such open heart surgery is particularly invasive and involves a lengthy and difficult recovery period. Reducing or eliminating the time a patient spends in surgery is thus a goal of foremost clinical priority.

One strategy for reducing the time spent in surgery is to eliminate or reduce the need for suturing a replacement valve into position. Toward this end, valve assemblies that allow implantation with minimal or no sutures would be greatly advantageous. Furthermore, while devices have been developed for the endovascular implantation of replacement valves, including collapsing, delivering, and then expanding the valve, such devices do not configure the valve in a manner that takes advantage of the natural compartments formed by the valve sinuses for optimal fluid dynamics and valve performance. In addition, to the extent that such devices employ a support structure in conjunction with a tissue valve, such valve constructs are configured such that the tissue leaflets of the support valve come into contact with the support structure, either during the collapsed or expanded state, or both. Such contact is capable of contributing undesired stress on the valve leaflet. Moreover, such support structures are not configured to properly support a tissue valve having a scalloped inflow annulus such as that disclosed in the U.S. patent application Ser. No. 09/772,526 which is incorporated by reference herein in its entirety.

Accordingly, there is a need for a valve replacement system comprising a collapsible and expandable valve assembly that is capable of being secured into position with minimal or no suturing; facilitating an anatomically optimal position of the valve; maintaining an open pathway for other vessel openings of vessels that may be located in the valvular sinuses; and minimizing or reducing stress to the tissue valve leaflets. The valves of the present invention may comprise a plurality of joined leaflets with a corresponding number of commissural tabs. Generally, however, the desired valve will contain two to four leaflets and commissural tabs. Examples of other suitable valves are disclosed in U.S. patent application Ser. Nos. 09/772,526, 09/853,463, 09/924,970, 10/121,208, 10/122,035, 10/153,286, 10/153, 290, the disclosures of all of which are incorporated by reference in their entirety herein.

SUMMARY OF THE INVENTION

The present invention provides systems and devices for the replacement of physiological valves. In one embodiment of the present invention, the replacement valve assemblies are adapted to fit substantially within the valve sinuses. Because the devices and procedures provided by the present invention eliminate or reduce the need for suturing, time spent in surgery is significantly decreased, and the risks associated with surgery are minimized. Further, the devices of the present invention are suitable for delivery by cannula or catheter.

In one preferred embodiment of the present invention a valve anchoring structure is provided that is dimensioned to be placed substantially within the valve sinus. In this embodiment, the valve anchoring structure extends substantially across the length of the valve sinus region.

In another preferred embodiment of the present invention a valve assembly is provided, comprising a valve and anchoring structure, in which the valve comprises a body having a proximal end and a distal end, an inlet at the proximal end, and an outlet at the distal end. The inlet comprises an inflow annulus, preferably with either a scalloped or straight edge. The outlet comprises a plurality of tabs that are supported by the anchoring means at the distal end. In preferred embodiments of the invention, the plurality of tabs are spaced evenly around the circumference of the valve.

In yet another embodiment of the present invention, a valve assembly is provided in which there is minimal or no contact between the valve and anchoring structure.

In still another embodiment of the present invention, a valve assembly is provided in which the valve is capable of achieving full opening and full closure without contacting the anchoring structure.

In yet another embodiment of the present invention, a valve assembly is provided in which the vertical components of the anchoring structure are limited to the commissural posts between sinus cavities, thereby minimizing contact between mechanical components and fluid, as well as providing flow to vessels located in the valve sinus.

In still another embodiment of the present invention, a valve is provided that firmly attaches to the valve sinus, obviating the need for suturing to secure the valve placement.

In a further embodiment of the present invention, a valve assembly is provided in which the anchoring structure may be collapsed to at least fifty percent of its maximum diameter.

In still a further embodiment of the present invention, an expansion and contraction device is provided to facilitate implantation of the valve and anchoring structure.

In another embodiment, the present invention provides adhesive means for securing the valve assembly in a valve sinus.

In yet another embodiment of the present invention, a valve sizing apparatus is provided for the noninvasive determination of native valve size.

The present invention also provides cutting means to remove the native diseased valve. One aspect of the cutting means comprises a plurality of jaw elements, each jaw element having a sharp end enabling the jaw element to cut through at least a portion of the native valve. Another aspect of the cutting means comprises a plurality of electrode elements, wherein radiofrequency energy is delivered to each electrode element enabling the electrode element to cut through at least a portion of the native valve. A further aspect of the cutting means comprises a plurality of ultrasound transducer elements, wherein ultrasound energy is delivered to each transducer element enabling the transducer element to cut through at least a portion of the native valve.

In yet another embodiment, the present invention provides a temporary two-way valve and distal protection filter assembly.

BRIEF DESCRIPTION OF THE DRAWINGS

FIG. 1 shows an exemplary valve during operation. FIG. 1A shows the valve in the open position during peak flow. FIG. 1B shows the valve in closed position to prevent backflow of the fluid across the valve.

FIG. 2 shows a preferred embodiment of the valve of the present invention. This valve features commissural tabs and a scalloped inflow annulus.

FIGS. 6A and B are schematics of a valve assembly comprising a valve and an anchoring structure in which the anchoring structure features an additional cloth ring along the valve inflow edge that serves as a gasket. FIG. 6C shows a valve anchoring structure according to one preferred embodiment of the present invention featuring a two-ring inflow rim.

FIG. 16A shows the valve assembly comprising a valve and elliptical segment anchoring structure in expanded form. FIG. 16B shows the same in compressed form

FIGS. 21A–G show different views of an elliptical segment anchoring structure further comprising cloth covering including a gasket cloth cuff at the inflow rim.

FIGS. 29A and B show an anchoring structure comprising an inflow and outflow ring connected by vertical posts that join to form a single vertical element upon compression.

DETAILED DESCRIPTION OF THE PREFERRED EMBODIMENTS

The present invention relates to valve replacement systems and devices. As illustrated in FIG. 1, a valve (1) comprises a distal or outflow end (2), leaflets (3) and a proximal or inflow end (4). A typical valve functions similar to a collapsible tube in that it opens widely during systole or in response to muscular contraction, to enable unobstructed forward flow across the valvular orifice (FIG. 1A). In contrast, at the end of systole or contraction, as illustrated in FIG. 1B, as forward flow decelerates, the walls of the tube are forced centrally between the sites of attachment to the vessel wall and the valve closes completely.

Replacement Valves

Figure 3A:
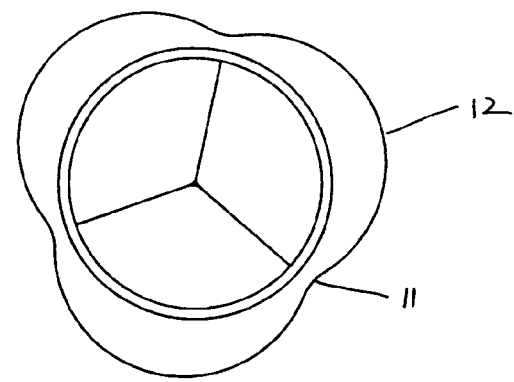
FIGS. 3A, B and C are representations of a typical valve sinus. These figures illustrate the anatomy of the sinus cavities, commissural posts, leaflets and inflow/outflow annuli.
Figure 3B:
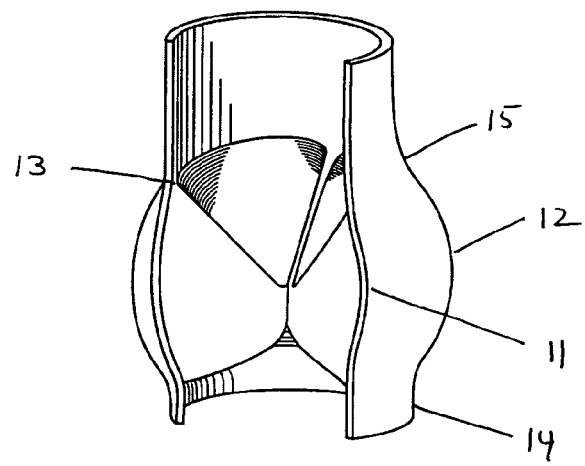
Figure 3C:
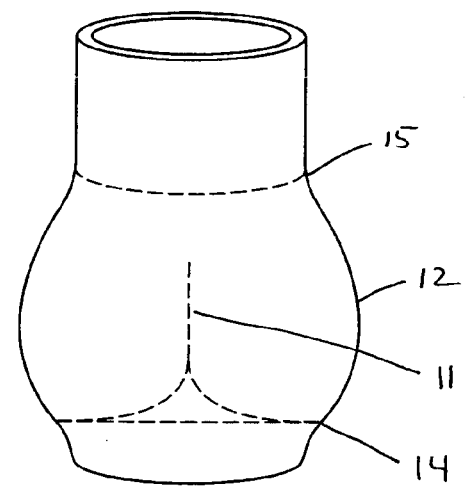

A preferred valve (5) for use with the systems and devices of the present invention is illustrated in FIG. 2 and is comprised of a body having a proximal end or inflow ring (6) and a distal end or outflow ring (7). The body is comprised of multiple leaflets of valve tissue joined by seams (8), wherein each seam is formed by a junction of two leaflets. A commissural tab region (9) extends from each seam at the distal end of the valve body. The proximal end (6) has an inflow ring with a peripheral edge that can be scalloped or straight. The inflow ring (6) of the valve can further comprise a reinforcement structure (10) that can be stitched to it. In preferred embodiments of the invention, the inflow edge of the valve is scalloped. The valve replacement systems and devices of the present invention are not limited, however, to the specific valve illustrated in FIG. 2. An important consideration in the design of valve replacement systems and devices that has received insufficient attention in previous approaches is the architecture of valve sinus. Valve sinuses are dilations of the vessel wall that surround the natural valve leaflets. Typically, each natural valve leaflet has a separate sinus bulge or cavity that allows for maximal opening of the leaflet at peak flow without permitting contact between the leaflet and the vessel wall. Thus, for example, a two-leaflet valve is surrounded by two sinus bulges, a three-leaflet valve by three, and a four-leaflet valve by four sinus cavities. The individual sinus bulges or cavities are separated by vertical fibrous structures known as commissural posts. These commissural posts define longitudinal structures with lesser outward curvature than the sinus cavities, as can be seen in FIG. 3. FIGS. 3A and B illustrate the reduced curvature of the commissural posts (11) compared with the curvature of the sinus cavities (12). FIG. 3C shows a view from outside the vessel of a commissural post (11) between two sinus cavities (12), while FIG. 3A shows a cross sectional view from the top of a closed valve within a valve sinus. The areas between the bulges define the commissural posts (11) and as can be clearly seen in FIG. 3B, the commissural posts serve as the sites of attachment for the valve leaflets to the vessel wall (13).

FIGS. 3B and C also show the narrowing diameter of the sinus region at both its inflow end (14) and outflow end (15) to form the inflow and outflow annuli of the sinus region. Thus, the valve sinuses form a natural compartment to support the operation of the valve by preventing contact between the leaflets and the vessel wall, which, in turn, may lead to adherence of the leaflets and/or result in detrimental wear and tear of the leaflets. The valve sinuses are also designed to share the stress conditions imposed on the valve leaflets during closure when fluid pressure on the closed leaflets is greatest. The valve sinuses further create favorable fluid dynamics through currents that soften an otherwise abrupt closure of the leaflets under conditions of high backflow pressure. Lastly, the sinuses ensure constant flow to any vessels located within the sinus cavities.

Figure 4:
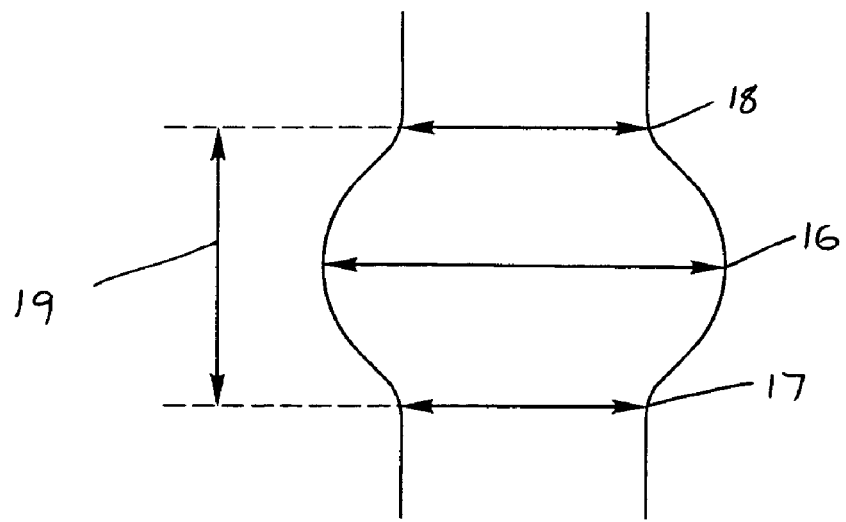
FIG. 4 is a schematic representation of the geometry and relative dimensions of the valve sinus region.

As shown in FIG. 4, the valve sinus region is characterized by certain relative dimensions which remain constant regardless of the actual size of the sinuses. Generally, the diameter of the sinus is at its largest at the center of the cavities or bulges (16), while there is pronounced narrowing of the sinus region at both the inflow annulus (17) and outflow annulus (18). Furthermore, the height of the sinus (19), i.e. the distance between the inflow and outflow annuli remains proportional to its overall dimensions. It is thus apparent that the sinus region forms an anatomical compartment with certain constant features that are uniquely adapted to house a valve. The systems and devices of the present invention are designed to utilize these anatomical features of the native sinus region for optimal replacement valve function and position.

Figure 5:
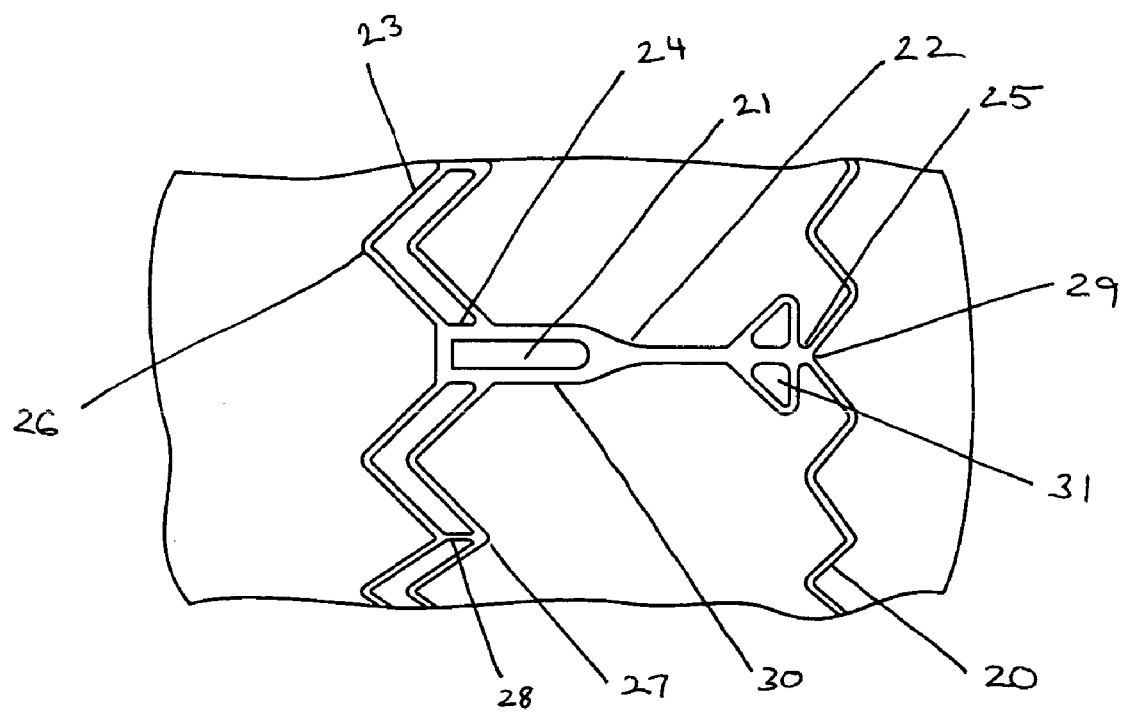
FIG. 5 shows a valve anchoring structure, in accordance with a preferred embodiment of the present invention, that is lodged inside a vessel.

Accordingly, in one preferred embodiment of the present invention, the replacement valve assembly comprises a collapsible and expandable anchoring structure adapted to support a valve distally along the commissural tab region and proximally along the inflow annulus. FIG. 5 shows a preferred anchoring structure adapted to support a valve such as that illustrated in FIG. 2. As seen in FIG. 5, the preferred anchoring structure has a generally tubular configuration within which the valve is secured. The valve is secured at its proximal (inflow) annulus by attachment to the inflow rim (20) of the anchoring structure and at its distal end via the commissural tabs that are threaded through the axially extending slots (21), which are formed in the support posts (22) that extend longitudinally from the inflow rim (20) to the outflow rim (23) of the anchoring structure. Thus, the distal ends (24) of the support posts contact the outflow rim (23) of the anchoring structure, whereas the proximal ends (25) of the support posts contact the inflow rim (20) of the anchoring structure.

In FIG. 5 the outflow rim (23) of the anchoring structure is depicted as comprising a plurality of rings that extend between the support posts (22) generally at or above the axially extending slots (21) that reside therein. The plurality of rings of the outflow rim (23) are configured in an undulating or zigzag pattern forming peaks (26) and valleys (27), wherein the individual rings remain substantially parallel to one another. The plurality of rings of the outflow rim comprise a vertical connector element (28) positioned at the center of the valleys (27) formed by the undulating or zigzag pattern. This vertical connector element (28) is designed to stabilize the anchoring structure and to prevent distortion of the valve during compression and expansion of the anchoring structure comprising the valve. The vertical element (28) extends longitudinally in the axial direction of the cylindrical anchoring structure. In a preferred embodiment, the outflow rim (23) of the anchoring structure comprises two rings. In a preferred implementation of this embodiment shown in FIG. 5, the inflow rim (20) of the support structure comprises a single ring that extends between the support posts (22).

Both the inflow (20) and outflow (23) rims of the anchoring structure are formed with an undulating or zigzag configuration, although the inflow rim (20) may have a shorter wavelength (circumferential dimension from peak to peak) and a lesser wave height (axial dimension from peak to peak) than the outflow rim (23). The wavelengths and wave heights of the inflow (20) and outflow (23) rims are selected to ensure uniform compression and expansion of the anchoring structure without distortion. The wavelength of the inflow rim (20) is further selected to support the geometry of the scalloped inflow annulus of a preferred valve of the present invention. Notably, as shown in FIG. 5, the undulating or zigzag pattern that forms the inflow rim (20) of the anchoring structure is configured such that the proximal ends (25) of the vertical support posts (22) are connected to the peaks (29) of the inflow rim (20). Similarly, the undulating or zigzag pattern that forms the outflow rim (23) of the anchoring structure is configured such that the distal ends (24) of the support posts (22) are connected to the valleys (27) of the outflow rim (23). Locating the distal ends (24) of the support posts at the valleys (27) of the outflow rim (23) will prevent the longitudinal extension of outflow rim (23) in the direction of the valve secured within the lumen of the anchoring structure upon compression of the valve assembly, thereby eliminating any contact between valve and anchoring structure. Likewise, locating the proximal ends (25) of the support posts at the peaks (29) of the inflow rim (20) will prevent longitudinal extension of the inflow rim (20) in the direction of the valve tissue. Thus, compression of the valve and anchoring structure does not lead to distortion of or injury to the valve.

FIG. 5 further shows that the support posts (22) are configured generally in the shape of paddle with the axial slot (21) extending internally within the blade (30) of the paddle. The blade (30) of the paddle is oriented toward the outflow rim (23) of the anchoring structure and connects to the outflow rim (23) at a valley (27) of the undulating or zigzag pattern of the outflow rim (23). An important function of the support posts (22) is the stabilization of the valve in general, and in particular the prevention of any longitudinal extension at points of valve attachment to preclude valve stretching or distortion upon compression of the device. The blades (30) of the paddle-shaped support posts (22) are designed to accommodate the commissural tabs of the valve. The support posts (22) further comprise triangular shaped elements (31) extending on each side of the proximal end (25) of the support post. The triangular shaped elements (31) are designed to serve as attachments sites for the sewing cuff gasket and may be designed in different shapes without losing their function.

The number of support posts (22) in this preferred embodiment can range from two to four, depending on the number of commissural posts present in the valve sinus. Thus, in a preferred embodiment, the anchoring structure comprises three support posts for a three-leaflet valve with a sinus that features three natural commissural posts. The support posts (22) of the anchoring structure are configured to coincide with the natural commissural posts of the sinus.

FIGS. 6A and B show the preferred embodiment of FIG. 5 having a valve secured internally. The valve (32) is secured at its proximal (inflow) annulus (33) by attachment to the inflow rim (20) of the anchoring structure and at its outflow or distal end (34) via the commissural tabs (35) that are threaded through the axially extending slots (21), which are formed in the support posts (22) that extend longitudinally from the inflow rim (20) to the outflow rim (23) of the anchoring structure. Notably, as can be seen in FIGS. 6A and B, in this preferred embodiment the outflow rim (23) of the anchoring structure is configured to be longitudinally displaced from the distal outflow annulus (34) of the valve leaflets (36) that reside within the lumen of the tubular anchoring structure, thereby avoiding any contact between the valve leaflets (36) and the anchoring structure.

As shown in FIGS. 6A and B, the inflow rim (20) of the anchoring structure can be secured to the proximal inflow annulus (33) of the valve via a suitable fabric that may be wrapped around the circumferential juncture at the inflow end (33) and stitched into position to form a sewing cuff (37). The fabric may be made of any suitable material including but not limited to woven polyester, such as polyethylene tereptphalate, polytetrafluoroethylene (PTFE), or other biocompatible material. Thus, the valve (32) is secured inside the anchoring structure by sewing a fabric ring (37) around the inflow rim (20) of the anchoring structure so as to create a sealing surface around the outer perimeter of valve's inflow annulus (33). In a preferred embodiment, the fabric ring (37) comprises two sewing cuff rings as shown in FIGS. 6A and B, with the second sewing cuff ring (38) having a larger diameter than the inflow annulus of the native valve sinus to ensure the firm lodging of the anchoring structure against the inflow annulus of the native valve sinus, thereby creating a tight, gasket-like seal.

The positioning of the valve (32) internally to the preferred anchoring structure with only the fabric of the commissural mounting tabs (35) of the valve (32) contacting the support posts (22) at the distal outflow annulus of the valve (34), while the proximal inflow annulus (33) of the valve is separated from the inflow rim (20) of the anchoring structure by the sewing cloth (37), ensures that no part of the valve (32) is contacted by the anchoring structure during operation of the valve (32), thereby eliminating wear on the valve (32) that may be occasioned by contact with mechanical elements.

In FIGS. 6A, B and C the outflow rim (23) of the anchoring structure is depicted as comprising a plurality of rings that extend between the support posts (22) generally at or above the axially extending slots (21) that reside at their distal ends (24). The plurality of rings of the outflow rim (23) are configured in an undulating or zigzag pattern forming peaks (26) and valleys (27), wherein the individual rings remain substantially parallel to one another. The plurality of rings of the outflow rim comprise a vertical connector element (28) positioned at the center of the valleys (27) formed by the undulating or zigzag pattern. This vertical connector element (28) is designed to stabilize the anchoring structure and to prevent distortion of the valve during compression and expansion of the anchoring structure containing the valve within. The vertical element (28) extends longitudinally in the axial direction of the cylindrical anchoring structure. In a preferred embodiment, the outflow rim of the anchoring structure comprises two rings.

FIG. 6C shows another implementation of a preferred anchoring structure of the present invention. In contrast to the implementation shown in FIG. 5, wherein the inflow rim (20) of the anchoring structure comprises a single ring that extends between the support posts (22), the implementation shown in FIG. 6C features an inflow rim (20) comprising two rings that are substantially parallel to each other and are connected by a vertical connector element (39) positioned at the center of the peaks (29) formed by the undulating or zigzag pattern. This vertical connector element (39) is designed to stabilize the anchoring structure and to prevent distortion of the valve during compression and expansion of the anchoring structure comprising the valve. The vertical element (39) extends longitudinally in the axial direction of the cylindrical anchoring structure. FIG. 6C also shows that the distal end (24) of the support post (22) may further comprise suture bores (41) to facilitate the placement of additional sutures for the securing the valve to the anchoring structure.

Because the wavelengths and wave heights of the inflow (20) and outflow rims (23) are selected to ensure uniform compression and expansion of the anchoring structure without distortion, a different wavelength and height may be chosen for the inflow ring (20) of an implementation of a preferred embodiment of an anchoring structure featuring an inflow rim (20) with two substantially parallel undulating rings as shown in FIG. 6C. Thus, the inflow rim (20) depicted in FIG. 6C may have substantially the same wavelength and height as the outflow rim (23). Similarly, the support posts (22) may be modified to comprise a widened proximal end (25) with an axial slot (40) extending longitudinally from the inflow rim (20) toward the distal end (24) of the support posts (22) and centrally through the triangular shaped elements (31). The widening of the proximal end (25) of the support posts (22) protects the triangular shaped elements (31) from distortion by the different collapsed profile of the inflow rim (20) with larger wavelength and height and ensures that no part of the valve (32) will be contacted by the anchoring structure during compression.

Figure 7:
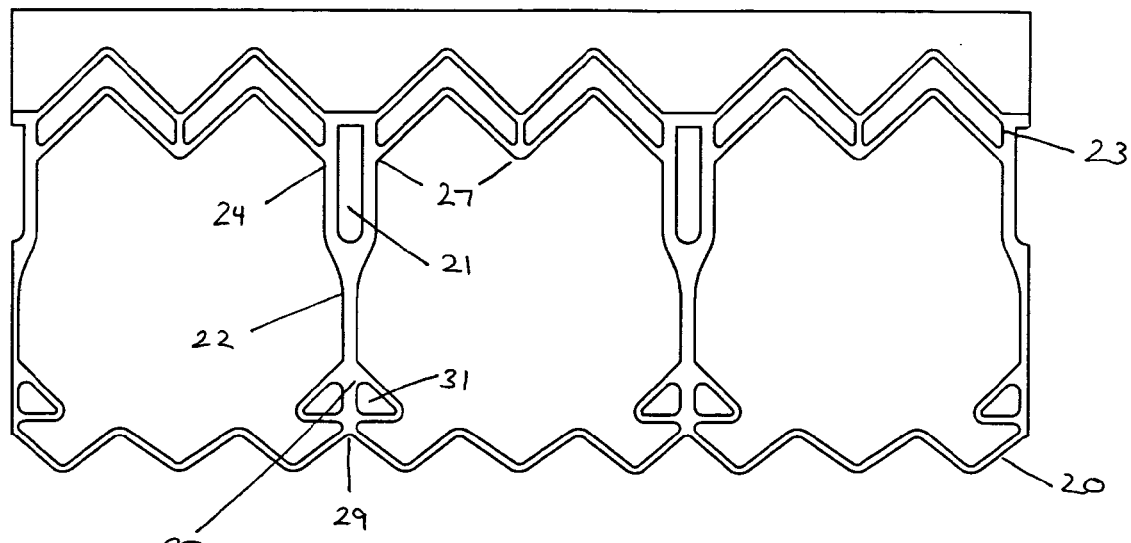
FIG. 7 is a diagrammatic representation of a flat pattern of a preferred embodiment of an anchoring structure in the expanded state.
Figure 8:
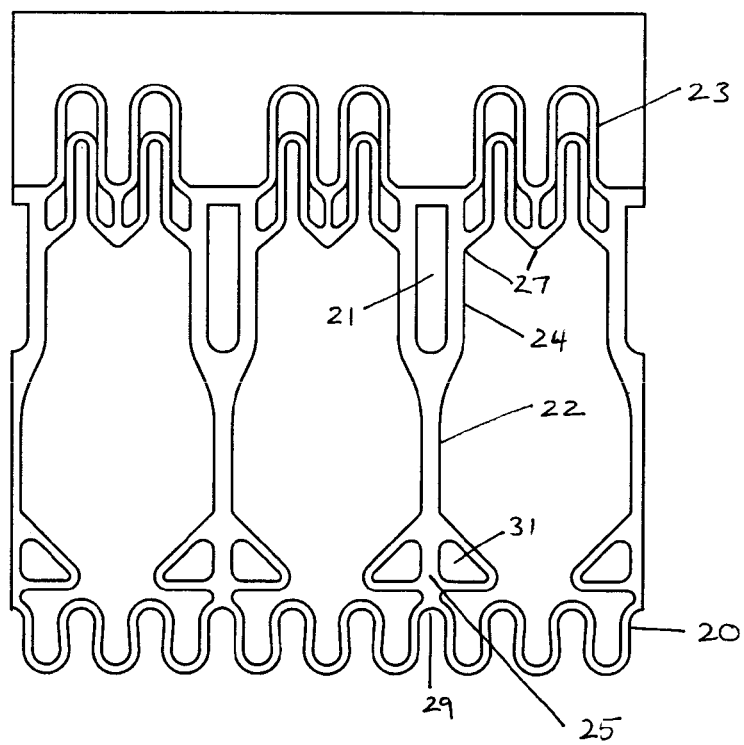
FIG. 8 is a diagrammatic representation of a flat pattern of a preferred embodiment of an anchoring structure in the compressed state.

FIGS. 7 and 8 show the expansion (FIG. 7) and compression (FIG. 8) profile of a preferred anchoring structure of the present invention. In a preferred embodiment of the present invention, the anchoring structure is collapsible to at least 50% of its expanded diameter. As shown in FIGS. 7 and 8, the undulating or zigzag pattern that forms the inflow rim (20) of the anchoring structure is configured such that the proximal ends (25) of the vertical support posts (22) are connected to the peaks (29) of the inflow rim (20). Similarly, the undulating or zigzag pattern that forms the outflow rim

(23) of the anchoring structure is configured such that the support posts (22) are connected to the valleys (27) of the outflow rim (23). Locating the distal ends (24) of the support posts (22) at the valleys (27) of the outflow rim (23) will prevent the longitudinal extension of outflow rim (23) in the direction of the valve upon compression of the device, thereby eliminating any contact between valve and anchoring structure. Similarly, locating the proximal ends (25) of the support posts (22) at the peaks (29) of the inflow rim (20) prevents structural interference between the proximal ends (25) of the support posts (22), in particular the triangular shaped elements (31) designed to support the scalloped inflow annulus of the replacement valve, and the undulating pattern of the inflow rim (20), as well as longitudinal extension of the inflow rim (20) in the direction of the valve tissue. Thus, compression of the valve and anchoring structure does not lead to distortion of or injury to the valve.

FIG. 8 shows that the support posts (22) connect to the outflow rim (23) at a valley (27) of the undulating or zigzag pattern and that during compression, the support posts stabilize the anchoring structure by preventing any longitudinal extension at points of valve attachment, that is at the proximal (25) and distal (24) ends of the support posts. The commissural mounting tabs of the valve are attached to the anchoring structure by extending through the axial slots (40) of the support posts to the exterior of the anchoring structure, while the inflow annulus of the valve is connected to the inflow rim (20) of the anchoring structure via a fabric ring. This arrangement allows firm attachment of the distal or outflow end of valve to the anchoring structure and ensures the proper positioning of the valve, with the outflow end being supported such that the leaflets are allowed to open and close with the movement of fluid across the lumen of the valve. It should be noted that the particular shapes of the individual elements of the structures disclosed herein may be modified by a person of skill in the art to achieve the advantages described without departing from the scope of the present invention.

The number of support posts (22) in this preferred embodiment can range from two to four, depending on the number of commissural posts present in the valve sinus. Thus, in a preferred embodiment, the anchoring structure comprises three support posts (22) for a three-leaflet valve with a sinus that features three natural commissural posts. The support posts (22) of the anchoring structure are configured to coincide with the natural commissural posts of the sinus.

An advantage of this arrangement is the additional option for the surgeon of suturing the valve assembly into place, wherein the anchoring structure provides the surgeon with additional guidance as to the proper anatomical positioning of the valve inside the native valve sinuses. Since the anchoring structure is dimensioned to fit precisely into the valve sinus cavities, the surgeon's positioning task is simplified to a visual determination of the location of the commissural posts of the native sinuses and their alignment with the support posts (22) of the anchoring structure of the valve. Thus, the present preferred embodiment takes advantage of the natural features of the valve sinus for the rapid orientation and attachment of the valve assembly. The ability of the anchoring structure to emulate the architecture of the valve sinus thus significantly reduces the surgeon's time spent on suturing the valve into position, should he so desire.

The geometry of the preferred embodiment of a valve anchoring structure further naturally positions it across the entire longitudinal extension of the native valve sinus, lodging the anchoring structure firmly against the vessel walls. Proximally, the inflow rim (20) of the anchoring structure naturally fits into the native valve sinus at a position near the inflow narrowing (annulus) of the native valve sinus against which it is designed to rest, while distally, the outflow rim (23) of the anchoring structure fits into the sinus at a position near the outflow narrowing (annulus) of the sinus against which it is designed to rest.

Between the proximal and distal ends of the anchoring structure the only longitudinal mechanical elements of the anchoring structure are the support posts (22) which are confined to the native commissural posts between the sinuses, leaving the sinus cavities free to create the native fluid currents that support leaflet closure and valve operation in general. A further advantage of this preferred embodiment of the present invention is the ability of the anchoring structure to emulate the natural compartment formed by the sinus for anchoring the valve. Thus, the anchoring structure is able to extend completely across the sinuses without placing mechanical elements into the path of fluid flow and without obstructing flow to any vessel openings that may be present in the valve sinuses.

In a preferred implementation of the present embodiment, the anchoring structure exerts radial force against the vessel wall so as to produce a compression fit. This may be accomplished by oversizing the anchoring structure such that it permanently seeks to expand to its original size. Thus, both the inflow (20) and outflow (23) rims are designed to push radially against the sinus walls near the inflow and outflow annuli of the sinus. The undulating or zigzag pattern formed by the inflow (20) and outflow (23) rings further serves to provide tire-like traction against the sinus wall for anchoring. Thus, the combination of compression fit, traction and sewing cuff rings (37 and 38) of the anchoring structure provides a firm anchor for the replacement valve and an optimal configuration in the native valve sinus.

In preferred embodiments of the present invention, the anchoring structure comprises a material that is expandable from a compressed configuration illustrated in FIG. 8 into the configuration depicted in FIG. 7. The anchoring structure may be non-self expanding, i.e. capable of being expanded from a compressed state using mechanical means, such as a balloon inflated from within the radial center of the anchoring structure, or using the expansion and compression devices disclosed herein. The anchoring structure comprises vertical tab support posts (22) which are designed to prevent inelastic deformation when the anchoring structure is collapsed prior to implantation.

Figure 9:
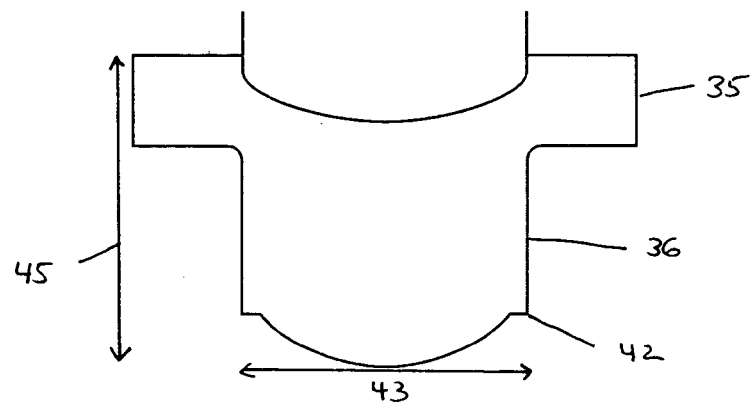
FIG. 9 shows a flat valve leaflet of a preferred valve to which the anchoring structure dimensions can be fitted.

FIG. 9 shows a representative flat valve leaflet (36) before it is sewn together with a desired number of additional leaflets (36) to form a three-dimensional replacement valve. The flat pattern of the leaflet (36) can be used to dimension the anchoring structure shown in FIG. 10 such that the commissural tabs (35) of the valve (36) will coincide with the axial slots (21) at the distal ends (24) of the support posts (22) and the proximal edges (42) at which the leaflets will be stitched or otherwise attached to each other to form the inflow annulus of the valve can be attached to the proximal ends (25) of the support posts (22) of the anchoring structure via the triangular shaped elements (31).

Figure 10:
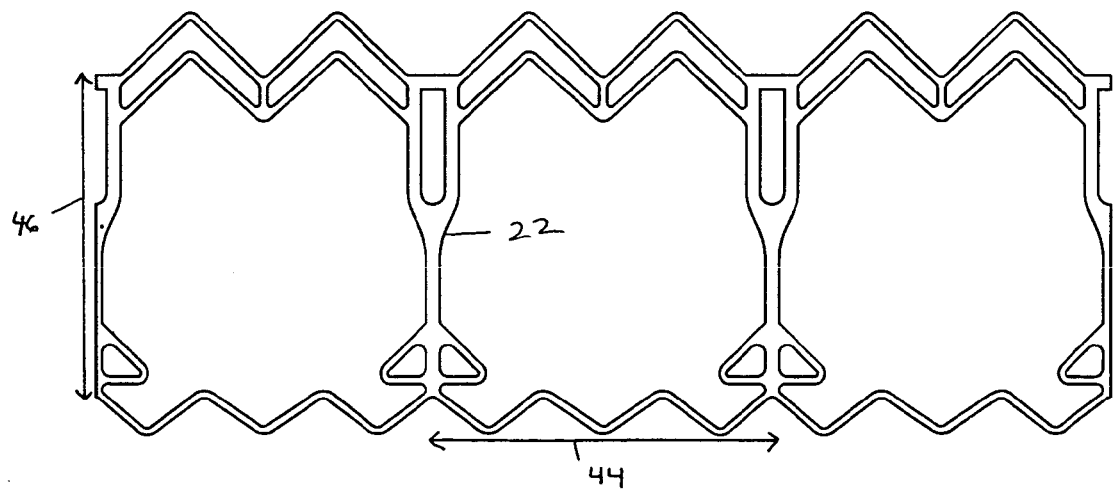
FIG. 10 illustrates the relative dimensions of a preferred embodiment of an anchoring structure of the present invention.

FIGS. 9 and 10 also show how an anchoring structure and valve may be scaled to fit different sizes of valve sinuses while retaining the proportional dimensions of the valve sinus. For example, if the width (43) of the leaflet (36) shown in FIG. 9 is chosen for a certain valve size, then the distance (44) between support posts (22) of the anchoring structure shown in FIG. 10 will be determined accordingly. Likewise, the height (45) of the leaflet (36) in FIG. 9 will determine the length (46) of the support posts (22) of the anchoring structure in FIG. 10. In this manner, a person of skill in the art can dimension both the valve and anchoring structure to fit any size of valve sinus.

Figures 11, 12:
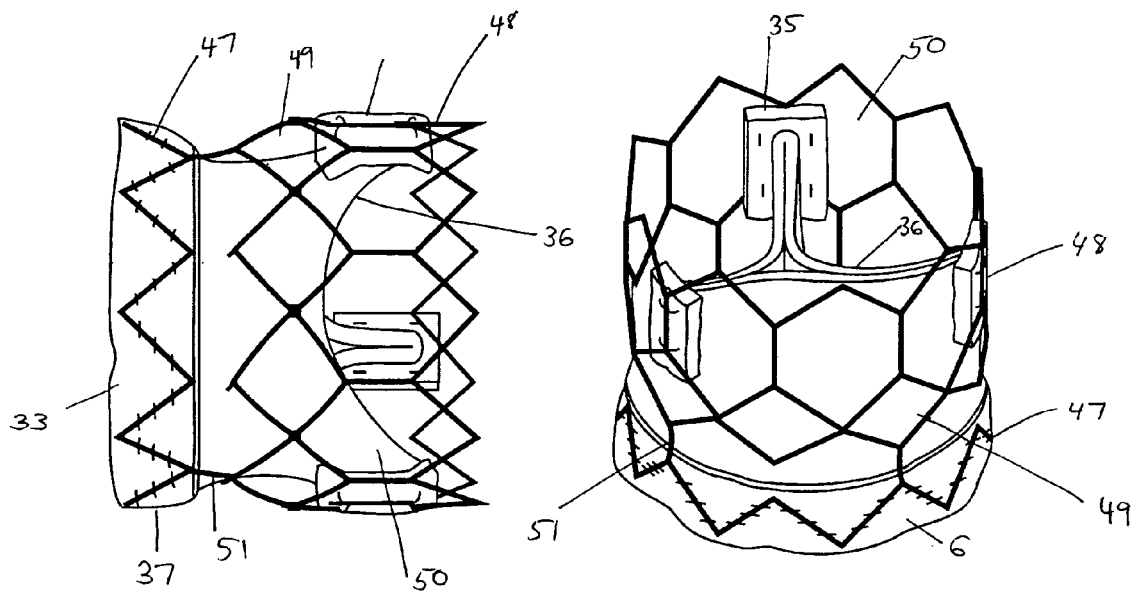
FIG. 11 shows a flared anchoring structure dimensioned to lodge inside the sinus cavities.
FIG. 12 shows a different view of the flared anchoring structure.

Another preferred embodiment of the present invention, illustrated in FIGS. 11 and 12, comprises a valve supported by a flared anchoring structure. The flared anchoring structure preferably comprises flared-out sections located at both the inflow (47) and outflow rims (48) to anchor it firmly against the narrowed inflow and outflow annuli of the valve sinuses. The flared distal end (48) of the anchoring structure is adapted to support the tab regions of the valve while the flared proximal end (47) supports the valve inflow annulus (33). The flared-out feature prevents contact between the valve tissue and the anchoring structure if the outflow rim (48) is positioned below the upper edges of the valve leaflets (36) in the open position, while also allowing the anchoring structure to secure itself in a sinus cavity of the vascular passageway. In this embodiment, the outflow rim (48) of the anchoring structure is comprised of diamond (49) and hexagon (50) shaped structures which facilitate collapsibility and dynamic compliance. The commissural tabs (35) of the valve (32) can be stitched directly to the hexagon shaped elements (50) of the outflow ring, rather than being secured via slots. The flared inflow rim (47) of the anchoring structure preferably comprises a single ring in the form of an undulating or zigzag pattern to which the valve's fabric ring (37) can be sewn. The inflow ring (47) of the anchoring structure is connected to the outflow rim (48) through vertical elements (51) that are positioned to coincide with the commissural posts of the native sinus region. Thus, the exemplary embodiment of FIGS. 11 and 12 comprises three vertical connecting elements (51) for a three-leaflet valve (32). However, it should be understood that the number of vertical connecting elements (51) is meant to be adapted to the number of native commissural posts present in the particular sinus region. The area between vertical connector elements (51) is thus left free of any structural elements for the accommodation of vessel openings that may be present in the particular valve sinus.

Figure 13:
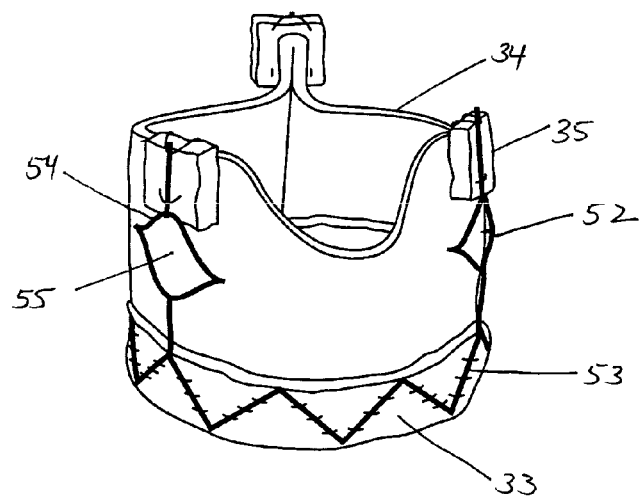
FIG. 13 shows a preferred embodiment of an anchoring structure lacking an outflow ring, and having support posts dimensioned to lodge in the sinus commissural posts, providing cantilevered support for the valve outflow end.

In another preferred embodiment, as illustrated in FIG. 13, a valve is supported by an anchoring structure comprising a plurality of posts (52) with a single ring (53) at the inflow rim. The ring (53) is configured in an undulating or zigzag pattern. In this exemplary embodiment the plurality of posts (52) number three for a three-leaflet valve sinus region. The three posts (52) extend in the distal direction from the single ring (53) located at the inflow end of the anchoring structure. The proximal end (33) of the valve is attached to the ring (53) portion of the anchoring structure so that the ring (53) provides support to the inflow annulus (33) of the valve. The inflow ring (53) comprises an undulating or zigzag pattern for tire-like traction against the vessel wall. The anchoring structure portion surrounding the proximal end (33) of the valve is preferably flared in an outward direction to improve anchoring forces against the vascular wall.

The three posts (52) extend from the proximal end (33) to the distal end (34) of the valve and provide cantilevered support to the tab regions (35) of the valve at the distal end (34). The three posts (52) are designed to be sufficiently flexible so that they may deflect inwardly in a controlled motion at back flow pressures to optimize the fatigue life of the anchoring structure. The posts (52) comprise a distal end (54) for the attachment of the valve commissural tabs (35). Below the distal end (54), the posts (52) comprise a diamond-shaped element (55) for enhanced structural stability and valve support. As with the previous embodiments of the present invention, the design according to the present embodiment creates open space between the proximal (33) and distal ends of the valve (34). This also ensures that there is no direct contact between the valve and the anchoring structure and that vessel openings located within the particular sinus remain unencumbered. Again, as in the preceding embodiments, the support posts (52) are configured to spatially coincide with the commissural posts of the valve sinuses for ease of positioning and anatomical optimization.

Figure 14:
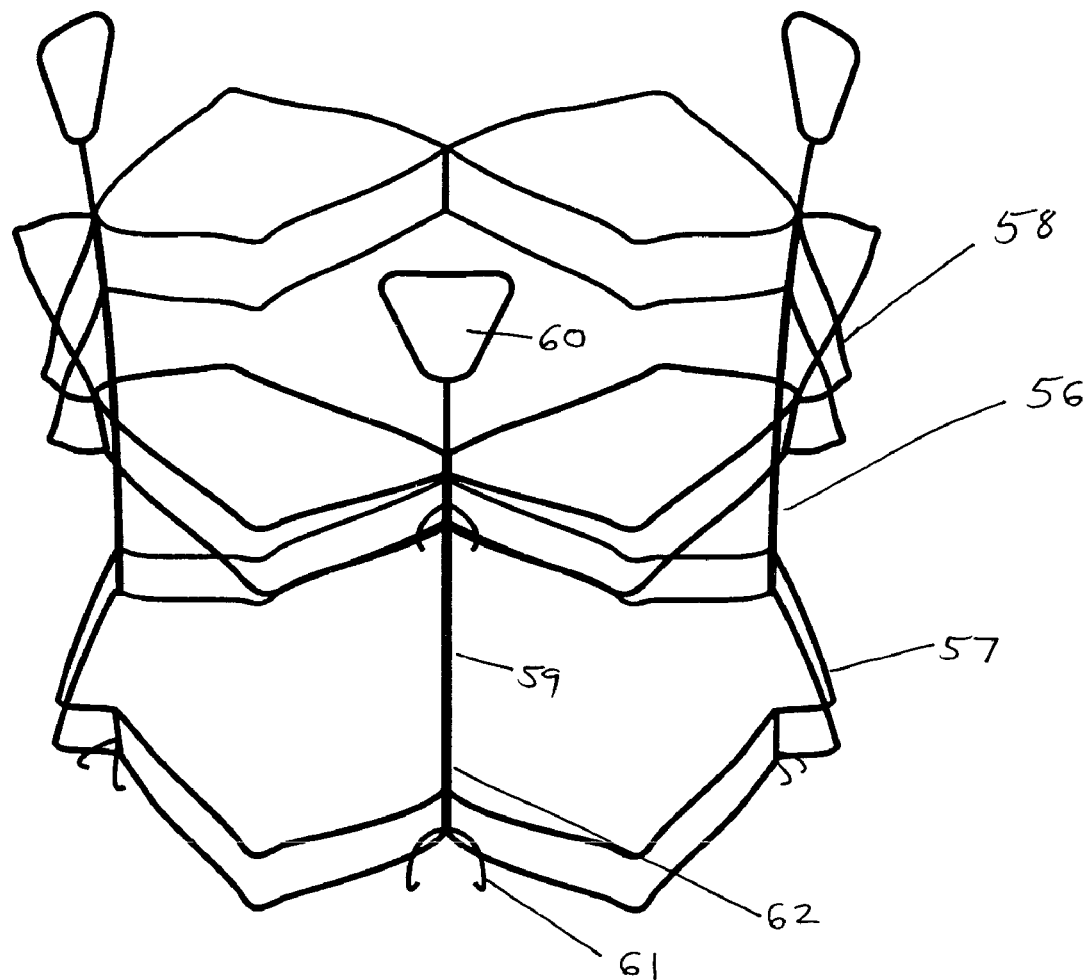
FIG. 14 shows a preferred embodiment of an anchoring structure with flared in- and outflow ends and support posts for lodging in the commissural posts with attachment windows capable of deflecting inward at back flow pressure.
Figure 15A:
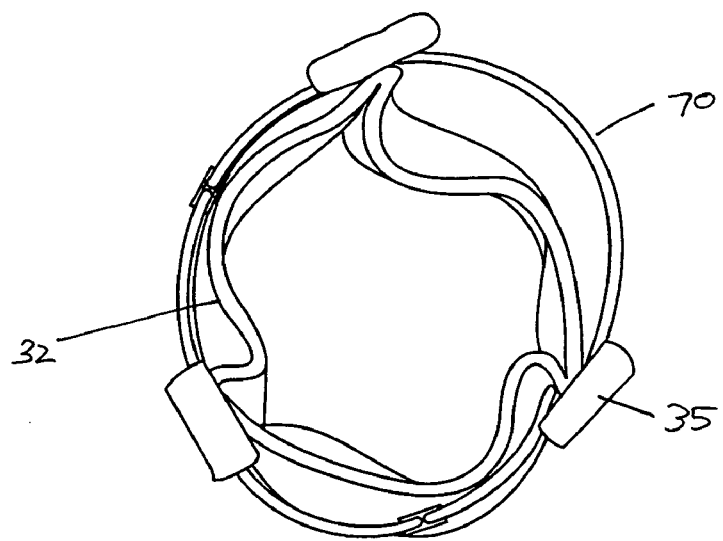
FIG. 15A shows a top view of a preferred embodiment of a valve assembly comprising a valve and an anchoring structure made of elliptical segments joined together.
Figure 15B:
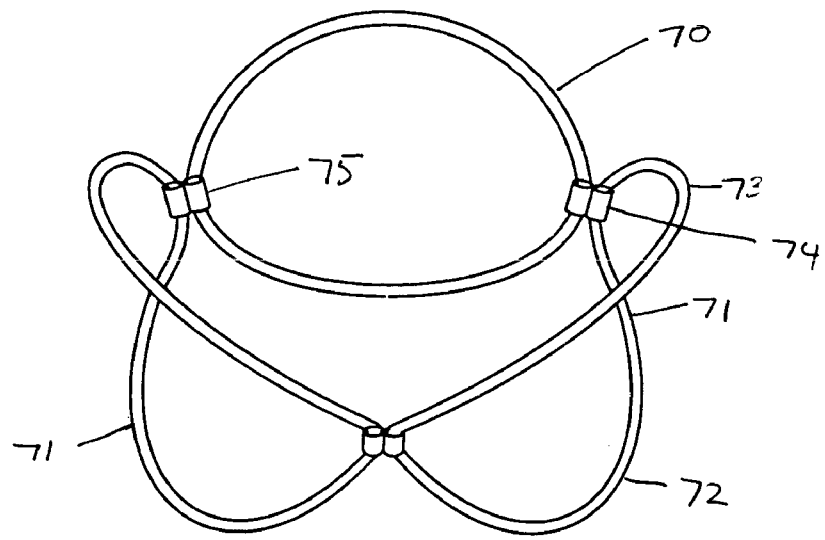
FIG. 15B shows a lateral view of the preferred anchoring structure without valve.

The anchoring structure embodiment illustrated in FIG. 14 comprises a valve supported by a multi-operational anchoring structure (56). The multi-operational anchoring structure (56) comprises a proximal end (57), a distal end (58), posts (59) extending from the proximal end (57) to the distal end (58), and a tab attachment window (60) attached to each post (59) at the distal end (58). The tab attachment windows (60) in the present embodiment have a triangular geometry that is designed to create an optimal interference fit between the anchoring structure and the commissural tabs The post (59) and tab attachment window (60) construction of the present embodiment allows inward deflection of the post at back flow pressure, thus providing cantilevered support to the valve and greater dynamic compliance with the sinus region. Both the proximal (57) and distal (58) ends of the anchoring structure are flared out to better secure the valve in the valvular sinus region. The proximal end or inflow rim (57) of the anchoring structure also preferably possesses barbs or hooks (61) at the proximal end (62) of the post (59) for better attachment to the vascular wall and/or the valve's inflow annulus. In this embodiment, the flared inflow rim (57) is depicted as featuring two undulating rings that are substantially parallel to one another, while the flared outflow rim features three undulating rings.

Yet another preferred embodiment of a valve anchoring device according to the present invention is illustrated in FIGS. 15–21. In this preferred embodiment, an elliptical segment (70) anchoring structure is used to support the valve (32) as shown in FIG. 15A. As shown in FIG. 15B, the elliptical segment anchoring structure (70) comprises a plurality of elliptical segments (71) that are joined together, either integrally, mechanically, or by adhesive means. Each elliptical segment (71) is flared outward at the proximal (72) and distal ends (73) of the anchoring structure and curved inward at the junctures (74) with the other segments (71) assuming the shape of a potato chip. When joined together side by side, the elliptical segments (71) form a tubular structure that is flared outward at both the inflow (72) and outflow (73) ends. The junctures (74) of the elliptical segments (71) are located at the center of a substantially straight area of the elliptical segments (71) that defines the longitudinal support post elements (75) of the elliptical segment anchoring structure (70) and also provides a gap location (75) near which the valve tabs (35) can be secured. The tab regions (35) extending from the seams of the valve can be attached to the anchoring structure using any suitable means, including, sewing, stapling, wedging or adhesive means. The tab regions (35) are preferably attached to the gaps (75) formed above the junctures (74) between the elliptical segments (71). The inflow (72) and outflow (73) rims of the anchoring structure are formed by the corresponding regions of the elliptical segments (71) that reside below and above the junctures (74). The inflow annulus of the valve can be secured at the inflow rim (72) via stitching to the inflow annulus fabric which also serves as a sealing gasket.

As shown in FIG. 16A, the vertical axes (76) of the elliptical segments (71) are dimensioned to exceed the axial length (77) of the valve (32), thereby eliminating valve leaflet (36) contact with the outflow rim (73) of the anchoring structure. FIG. 16B shows how both the valve (32) and anchoring structure (70) of the present embodiment can be compressed radially to facilitate implantation. The concave configurations of the elliptical segments (71) effectively form a radial spring that is capable of being radially collapsed under pressure for deployment and then expanded when positioned at the implant site. One advantageous feature of the instant design is that the region of juncture (74) between the elliptical segments (71) does not become extended upon compression of the anchoring structure. The valve (32) and anchoring structure (70) of the present embodiment can also be compression fit within a valve sinus cavity to exert radial force against the sinus walls.

Figure 17:
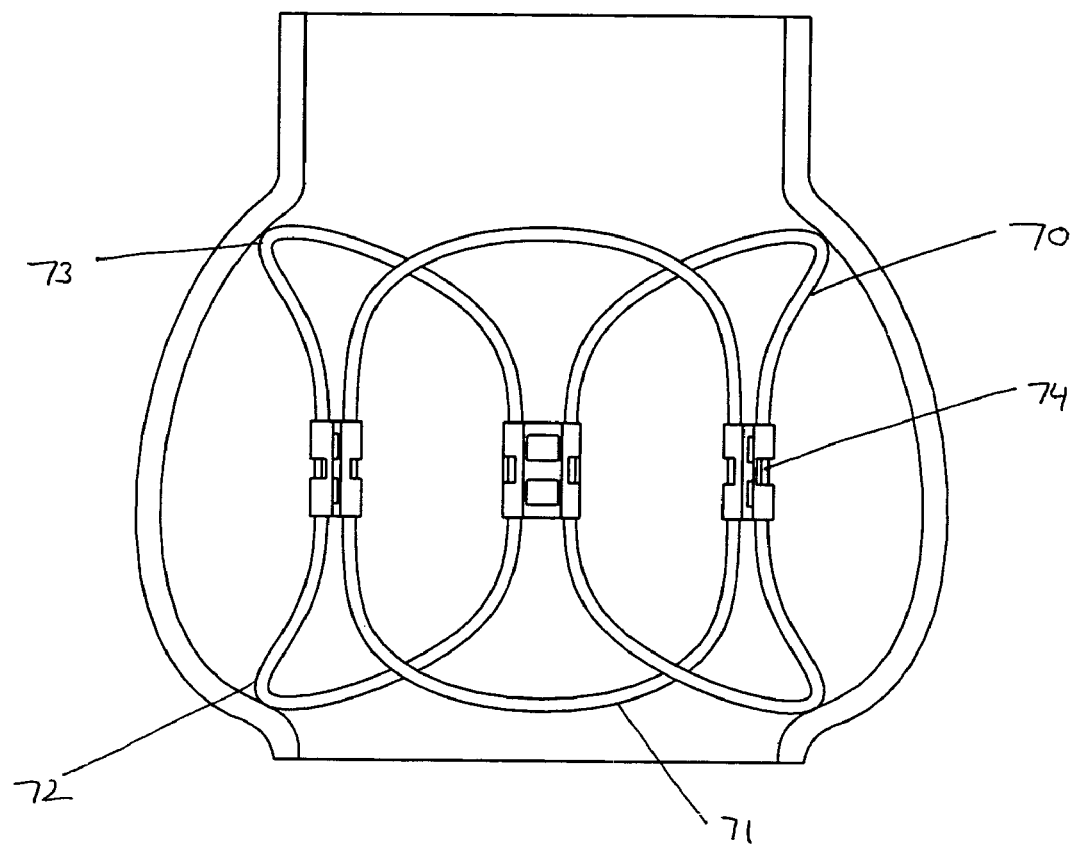
FIG. 17 shows the lodging of an elliptical anchoring structure inside the valve sinus cavities.

As shown in FIG. 17, the anchoring structure (70) is preferably dimensioned to be lodged substantially within a valve sinus, with the regions of juncture (74) between the elliptical segments (71) being configured to reside at the location of the native commissural posts. The elliptical segment anchoring structure (70) is designed to expand at the proximal end (72) during peak flow and at the distal end (73) during peak backflow pressure, thereby maintaining pressure against the vascular wall. As a result, the valve and anchoring structure (70) of the present embodiment will remain secure in the valve sinus without sutures. A metal wire frame made from a metal that exhibits a high modulus of elasticity and that is biocompatible is preferred, such as Nitinol, as such materials exhibiting superior compressibility allow the anchoring structure to be self-expandable.

Figure 18A:
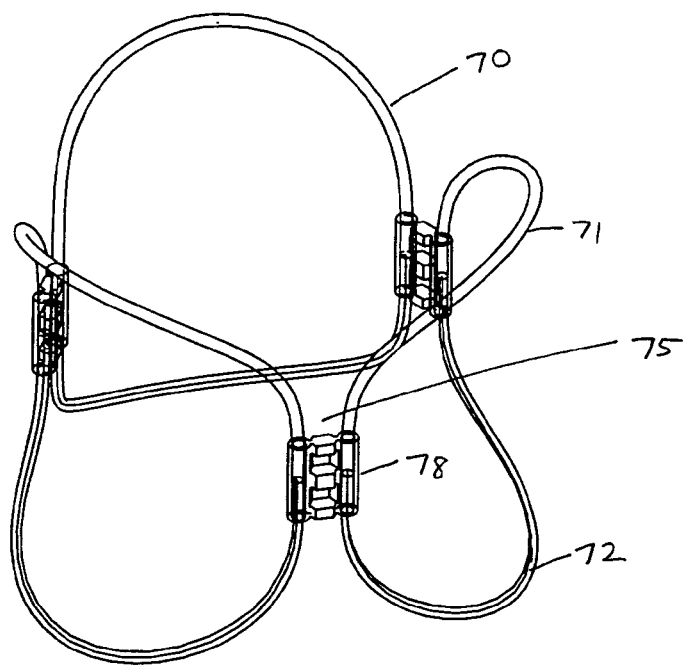
FIG. 18A shows how the elliptical segments of the anchoring structure may be joined by a double crimp.
Figure 18B:
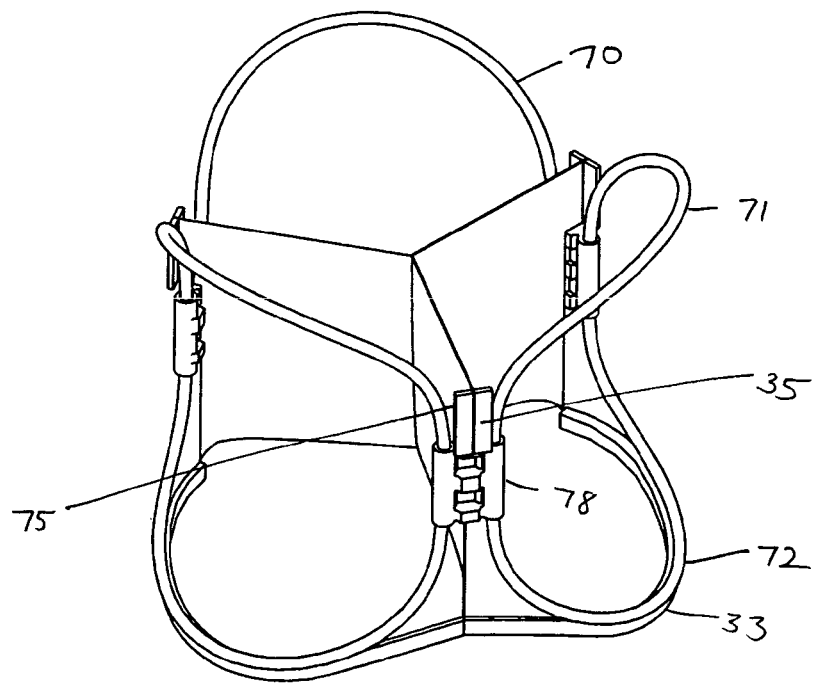
FIG. 18B shows how the valve is positioned inside the anchoring structure.

A further preferred embodiment of a valve anchoring structure according to the present invention is illustrated in FIGS. 18A and B. In the present embodiment, an elliptical segment anchoring structure (70) is presented in which the elliptical segments (71) are joined together by a specialized double crimp (78). FIG. 18B shows that the valve tabs (35) can be secured near the double crimp (78) that joins the elliptical segments (71). The tab regions (35) are preferably attached to the gaps (75) between the elliptical segments (71). The inflow annulus of the valve (33) can be secured at the inflow rim (72) via stitching to the inflow annulus fabric which also serves as a sealing gasket.

Figure 19A:
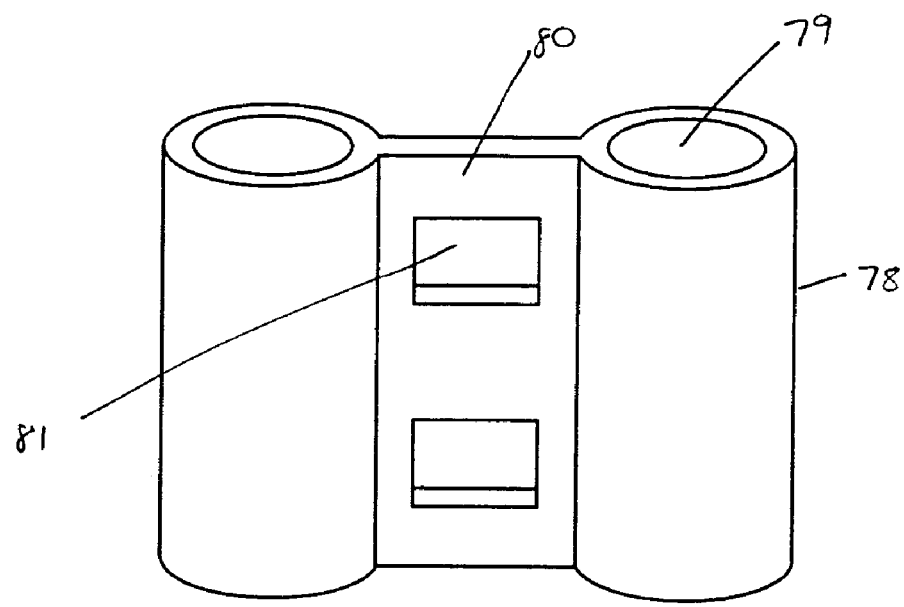
FIG. 19A shows a double crimp uniquely designed to flexibly join the elliptical segments.
Figure 19B:
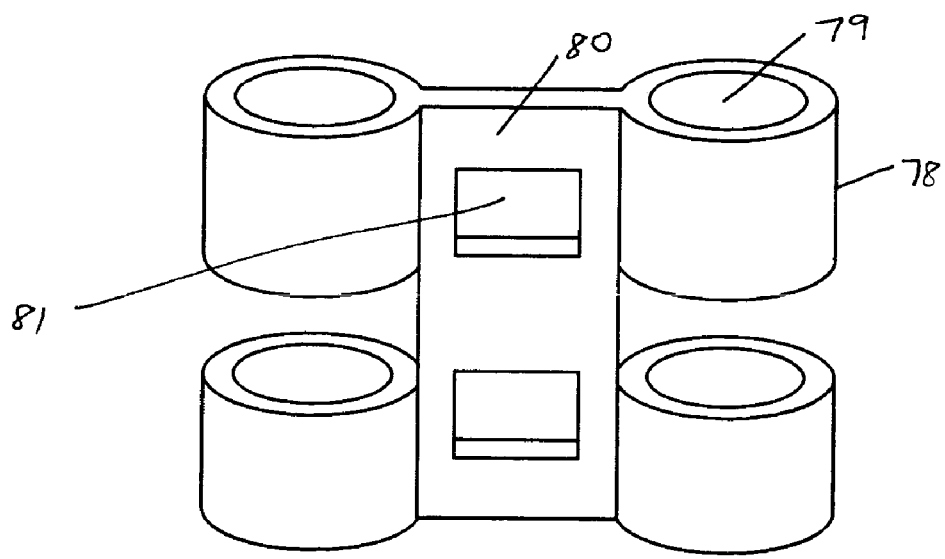
FIG. 19B shows a modified double crimp.

FIGS. 19A and B illustrate the double crimp (78) used to join the elliptical segments (71). As shown in FIGS. 19A and B, the double crimp (78) comprises two hollow tubes (79), one for each elliptical segment (71) to be inserted. The hollow tubes (79) of the double crimp (78) are designed to allow for better motion of the individual elliptical segments (71) and to minimize material stresses during expansion and compression of the anchoring structure. The double crimp (78) further comprises a central portion (80) joining the two hollow tubes (79). This central portion (80) comprises one or more holes (81) to facilitate the attachment of the valve commissural tabs to the anchoring structure and to reduce the mass of the double crimp (78). Thus, the double crimp (78) also serves as an attachment site for the valve and further acts as a stop against backflow pressure on the valve leaflets.

Figure 20A:
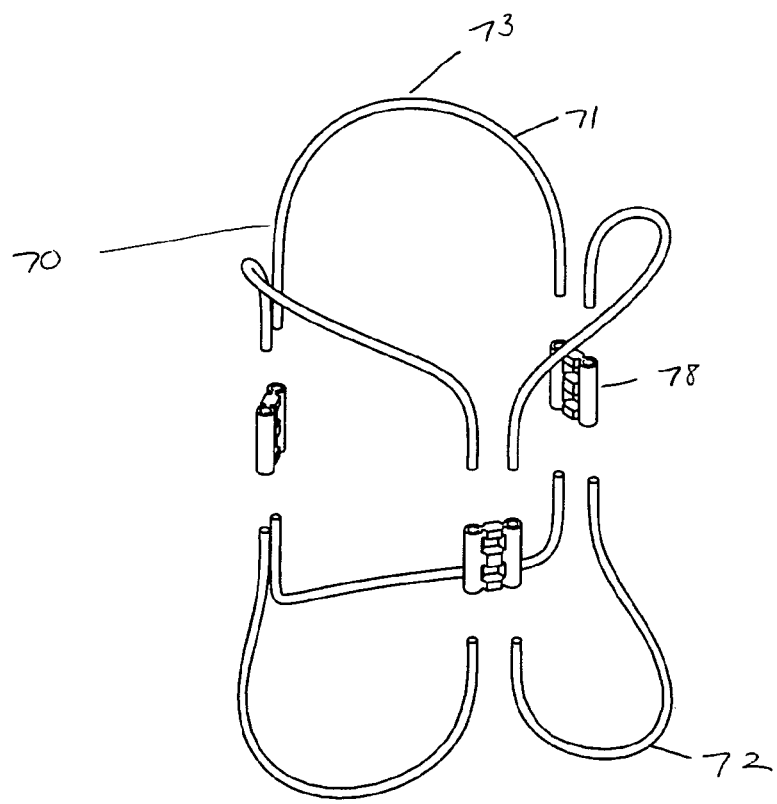
FIG. 20A shows how the elliptical segments may be assembled into the double crimp.
Figure 20B:
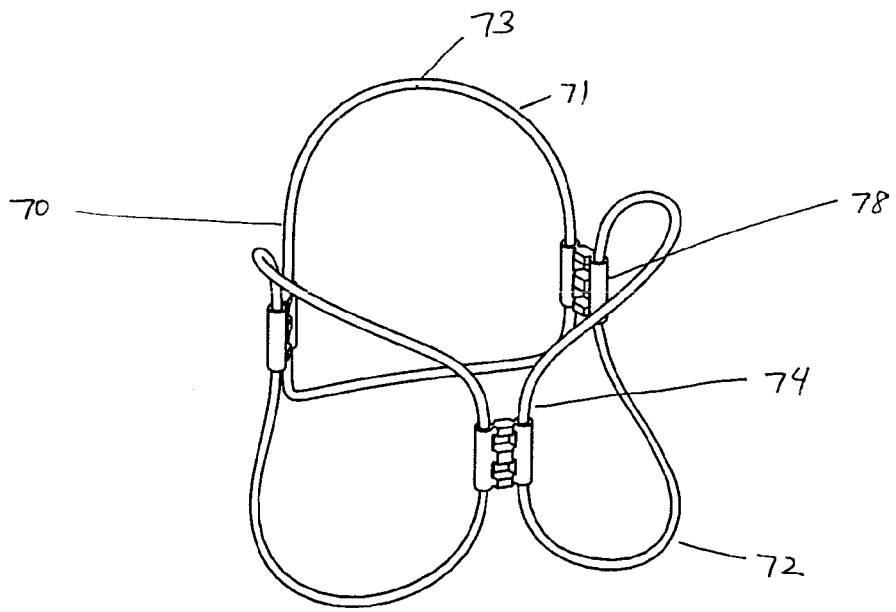
FIG. 20B shows the final assembly.

FIG. 20A shows the insertion of the elliptical segments (71) of the preferred anchoring structure embodiment (70) into the double crimp (78). As with the previous embodiments, the present embodiment is dimensioned to be lodged substantially within the valve sinuses, with the joined regions (74) of the elliptical segments in FIG. 20B configured to align with the commissural posts of the sinus and the flared inflow (72) and outflow ends (73) of the anchoring structure configured to rest against the sinus cavities.

FIGS. 21A through G show how the elliptical segment anchoring structure (70) may additionally be covered with cloth (82), particularly at the inflow end (72) to provide traction and a gasket-like seal. Thus, this preferred embodiment of the present invention is dimensioned to follow the sinus architecture and to lodge into the sinus cavities and against the inflow and outflow annuli of the sinuses for optimal securing and positioning of the replacement valve.

Figure 22A:
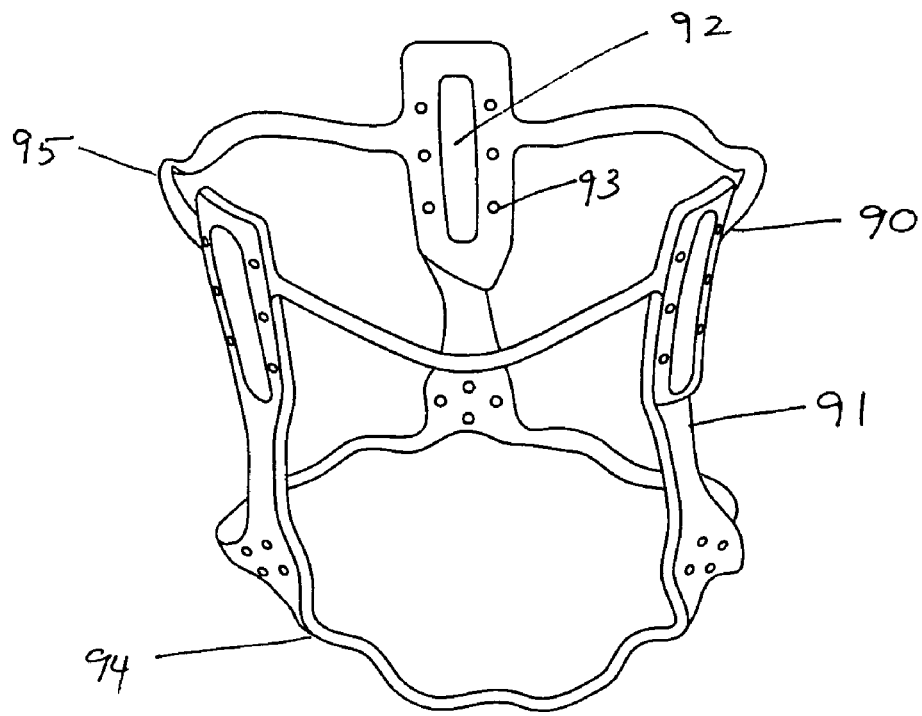
FIGS. 22A and B show different views of an elliptical segment anchoring structure made from a single piece of tubing.
Figure 22B:
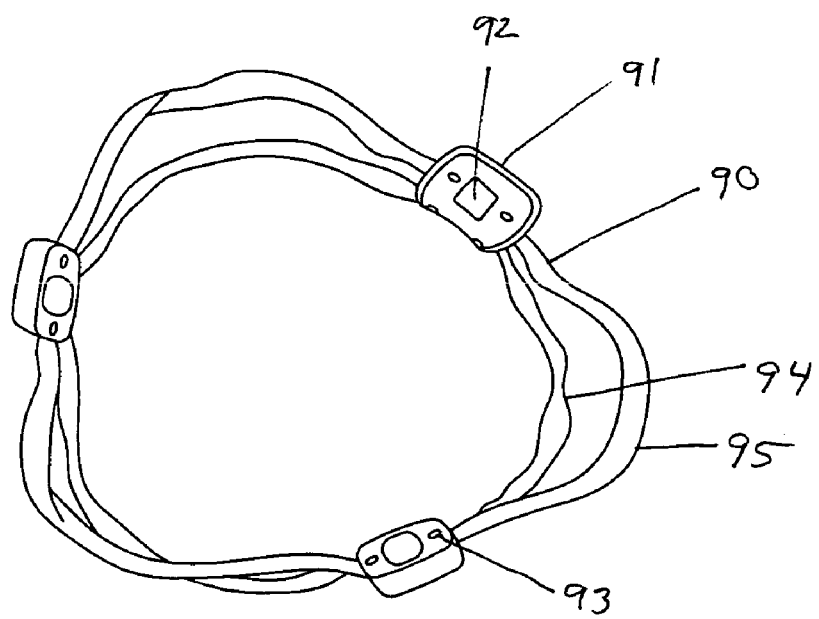

FIGS. 22A and B illustrate a further preferred embodiment the present invention. This figure shows an elliptical segment anchoring structure (90) made from one piece of tubing. As illustrated, the support posts (91) that form the slots (92) for the valve tabs include a series of small holes (93) on either side of the slot (92) to facilitate suture or mechanical attachment of the commissural tabs of the valve. Again, this anchoring structure (90) is dimensioned to fit substantially within the valve sinuses with the support posts (91) being configured to reside in the commissural posts between the individual sinus cavities. The present embodiment also exerts axial force particularly at the flared inflow (94) and outflow rims (95) against the sinus walls to anchor the valve.

Figure 23A:
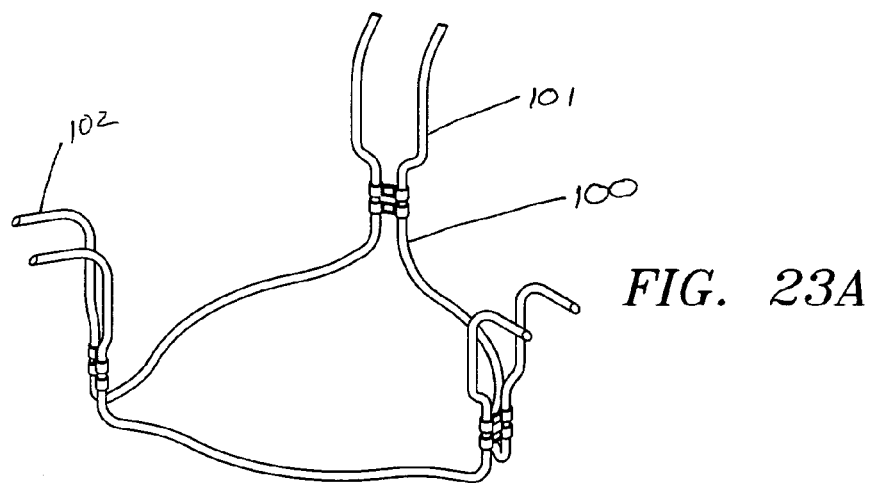
FIGS. 23A through D show an elliptical segment anchoring structure in which the upper segments have been removed and the ends of the junctions are formed into prongs.
Figure 23B:
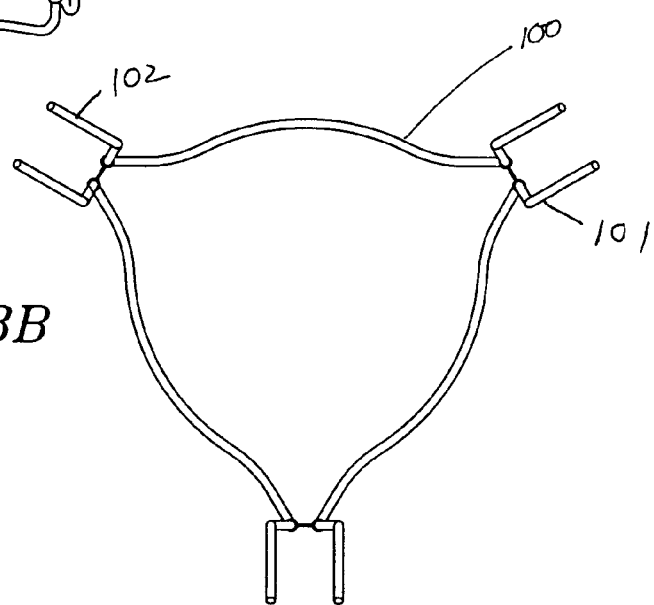
Figure 23C:
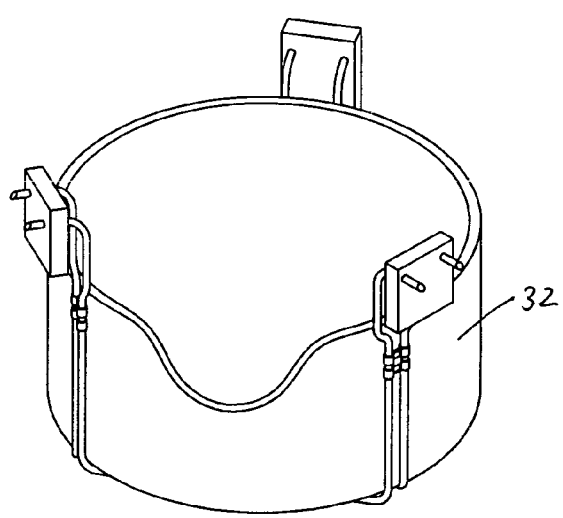
Figure 23D:
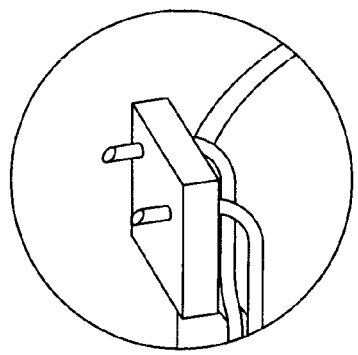

Yet another embodiment of a valve and anchoring structure according to the present invention is illustrated in FIGS. 23A through D. In the present embodiment, a claw anchoring structure (100) is shown in FIG. 23A. This embodiment corresponds to an elliptical segment embodiment wherein the upper portions of each elliptical segment have been removed. The ends of the junctures (101) of the remaining elliptical segments are shaped into prongs or claws (102). Thus, the claw anchoring structure (100) comprises a flexible spring frame having a plurality of barbs (102), located distally just beyond where the valve leaflet tab regions meet the anchoring structure. The claw anchoring structure (100) preferably comprises at least one barb (102) for each valve leaflet tab included in the valve. The barbs (102) are designed to anchor the valve (32) and anchoring structure (100) to the vascular wall.

Figure 24:
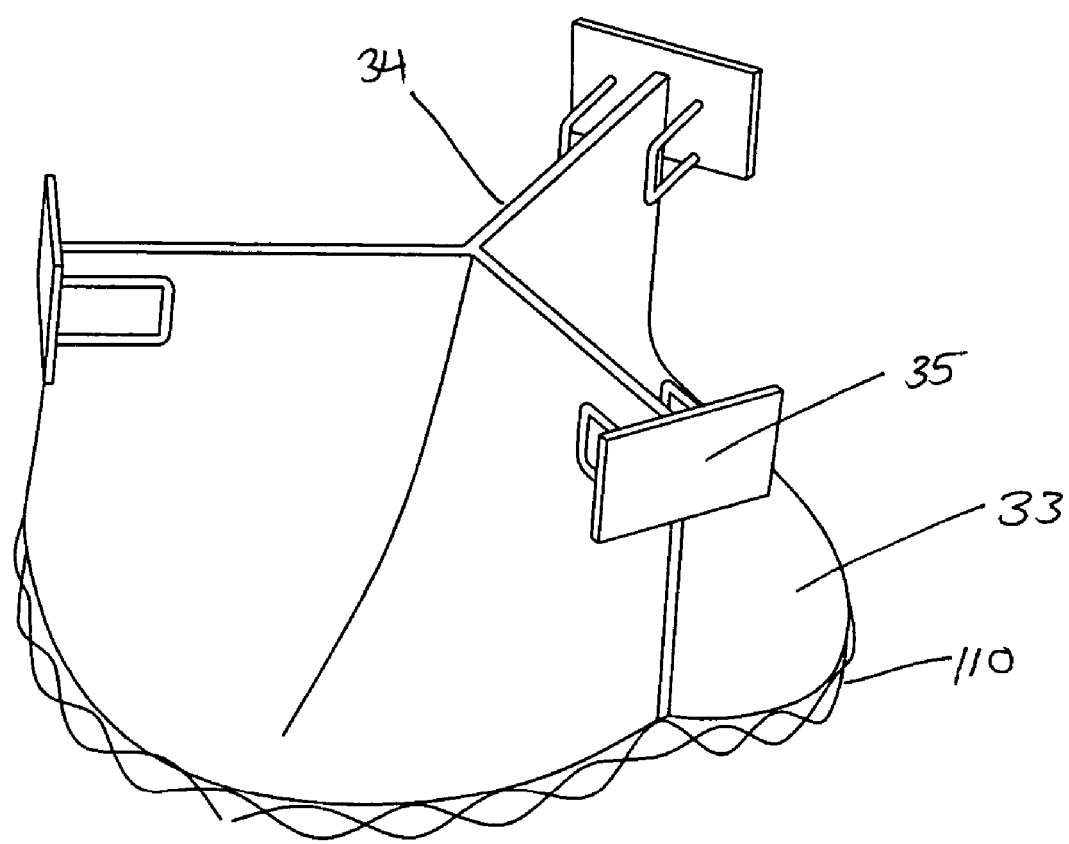
FIG. 24 shows a preferred valve assembly of the present invention with an anchoring structure comprising a ring incorporated into the valve inflow rim.

In another preferred embodiment of the invention, an anchoring structure is provided that lacks vertical support posts. As shown in FIG. 24, the representative anchoring structure configuration comprises an inflow ring (110) that is adapted to being secured to the inflow annulus of the valve (33) via stitching to the reinforced fabric sewing ring in a manner similar to the prior representative implementations. The undulating or sinusoidal pattern of the ring (110) facilitates radial collapse and expansion and exerts radial force against the vessel wall. The anchoring structure does not support the outflow annulus (34) of the valve. Rather, the valve's commissural tabs (35) are attached to the sinus walls via mechanical means, such as sutures, staples, or wire.

Figure 25A:
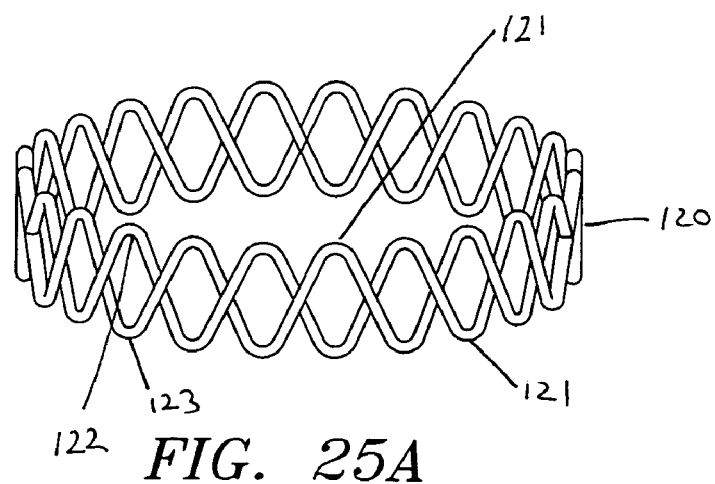
FIG. 25A shows an anchoring structure comprising two undulating rings with inverse wave patterns.

Another representative embodiment of an anchoring structure is shown in FIG. 25A. The present embodiment comprises a dual-ring anchoring structure (120). The dual ring (120) of the present embodiment may, as in the previous embodiment, be secured to the inflow annulus of the valve via stitching to the reinforced fabric sewing ring. The undulating or sinusoidal pattern of the individual rings (121) is configured such that the peaks (122) of one ring (121) coincide with the valleys (123) of the other ring and vice versa, thereby forming a sine-cosine pattern. This pattern facilitates radial collapse and expansion and exerts radial force against the vessel wall. As in the previous embodiment, the dual ring anchoring structure (120) does not support the outflow annulus of the valve. Rather, the valve's commissural tabs are attached to the native sinus walls via mechanical means, such as sutures, staples, or wire, or additionally by the adhesive means disclosed herein.

Figure 25B:
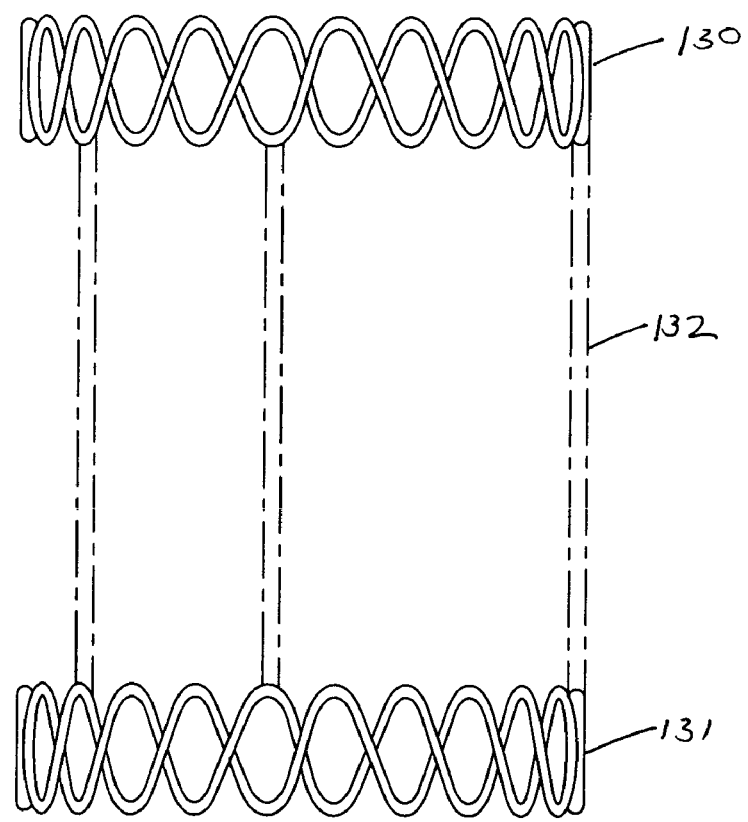
FIG. 25B shows an anchoring structure comprising two such rings connected by vertical elements.

FIG. 25B shows another dual ring embodiment of the present invention. This anchoring structure is comprised of an upper (distal) dual ring (130) and a lower (proximal) dual ring (131). The lower dual ring (131) is connected to the proximal end of the valve at the inflow annulus while the upper dual ring (130) is connected to the distal end of the valve at the outflow annulus. The valve may be connected to the rings (130, 131) via sutures, clips or any other suitable means for attachment. The valve and the attached proximal (131) and distal (130) rings can be collapsed and inserted via a catheter. Once the valve has reached its desired location in the vascular passageway, the two rings (130, 131) are expanded to secure the valve in the vascular passageway. As in the previous embodiment, each dual ring (130, 131) comprises a wire frame with a circular cross-section and a sinusoidal pattern. The sinusoidal pattern may be of a sine-cosine shape with a varied frequency and amplitude. One or more longitudinal rods (132) may be used to connect the two dual rings (130, 131) and maintain longitudinal separation and radial orientation. The rods (132) may be removable so that once the valve is implanted in the vascular passageway they can be removed.

Figure 26:
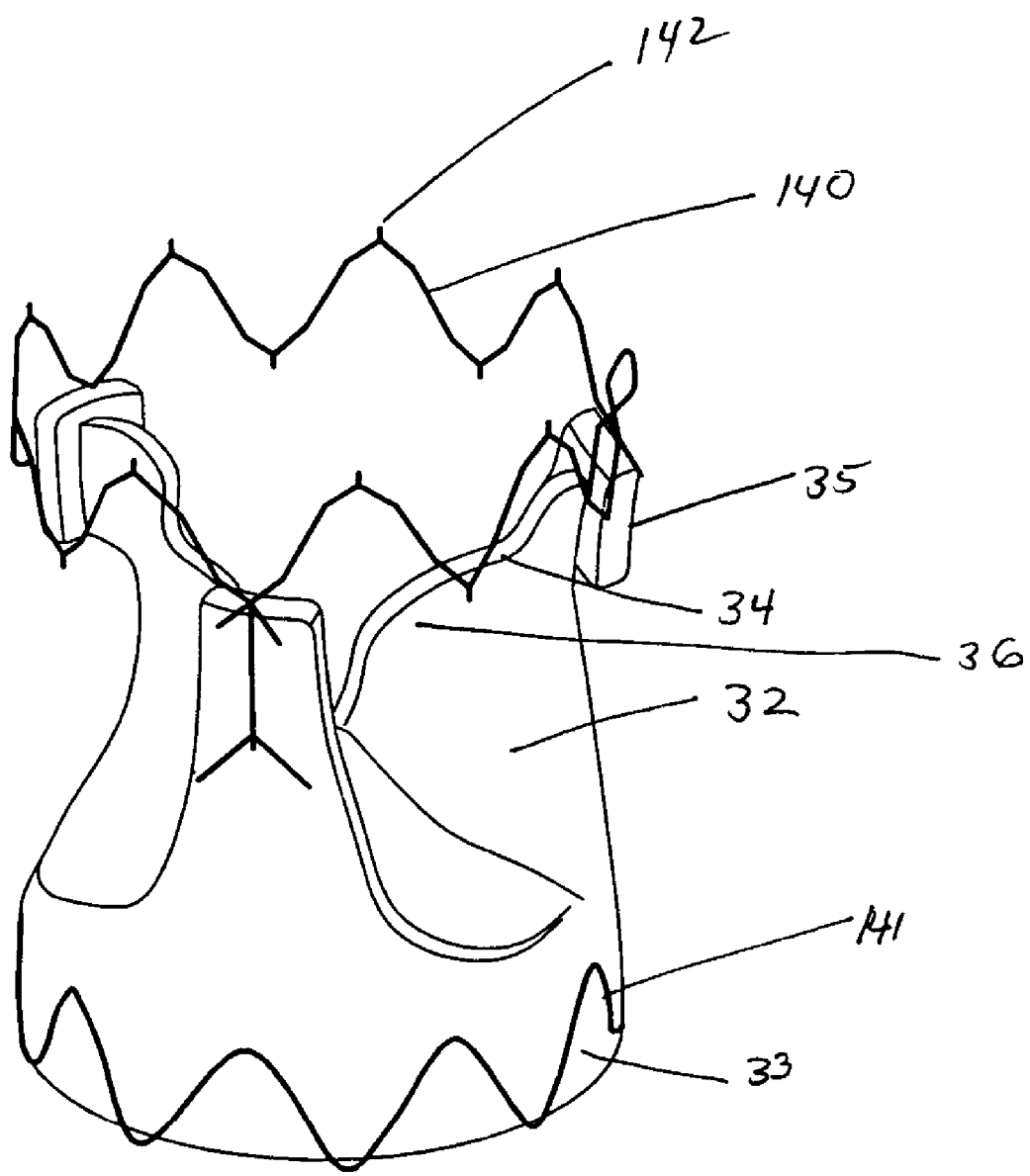
FIG. 26 shows a valve assembly comprising an anchoring structure in which the inflow ring and outflow ring are structurally unconnected.

In another preferred embodiment, illustrated in FIG. 26, an upper single ring (140) with an undulating or zigzag pattern provides support to the tab regions (35) of the valve (32) at the distal end (34) of the valve whereas a lower single ring (141) configured in an undulating or sinusoidal pattern provides support to the inflow annulus (33) at the proximal end of the valve (32). The inflow ring (141) is stitched to the sewing fabric wrapped around the circumference of the inflow annulus of the valve, as described previously. The outflow ring (140) of the anchoring structure generally resides above the leaflets (36) to avoid leaflet contact. To improve traction, the inflow or outflow rings may comprise attachment barbs (142). The structural dissociation between the rings (140, 141) provides improved dynamic compliance while retaining the benefits of a two ring design.

Figure 27A:
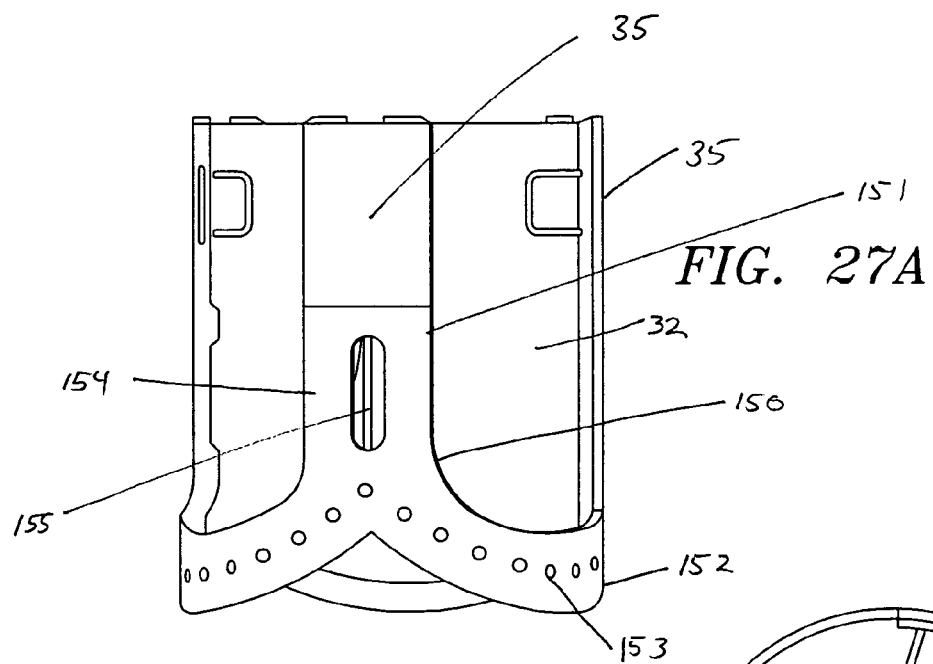
FIG. 27A-C show a tubular anchoring structure.
Figure 27B:
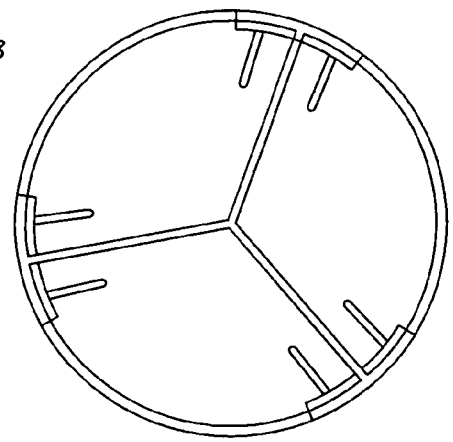
Figure 27C:
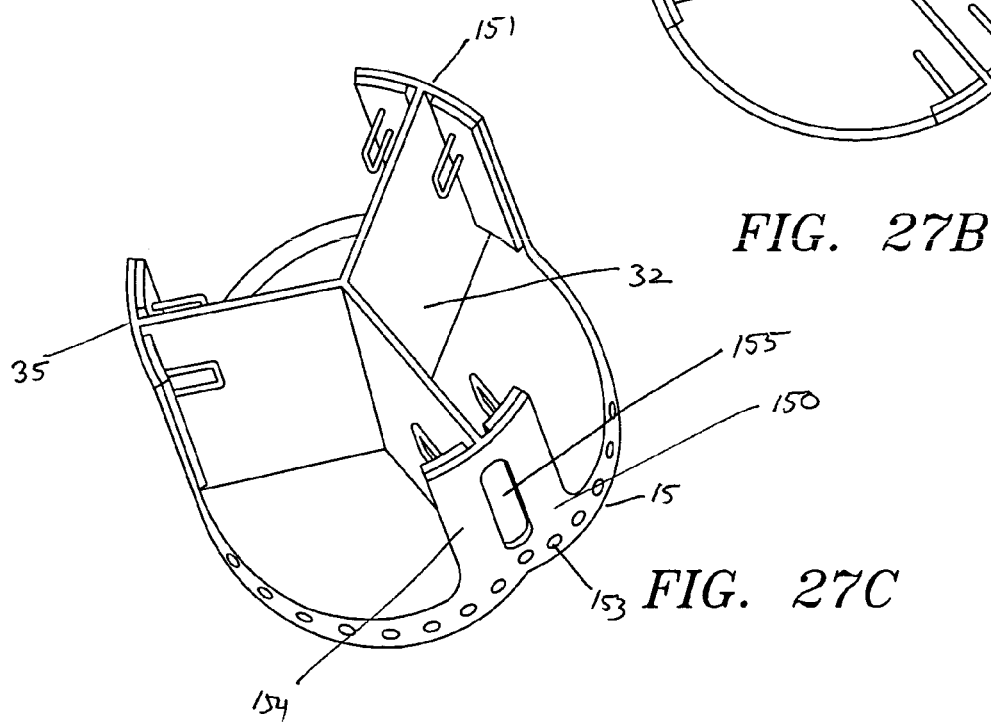
Figure 28B:
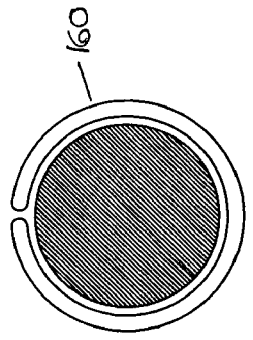
FIGS. 28A–D show an anchoring structure comprising an inflow ring and an outflow ring connected by vertical posts that slide across one another upon compression.
Figure 28D:
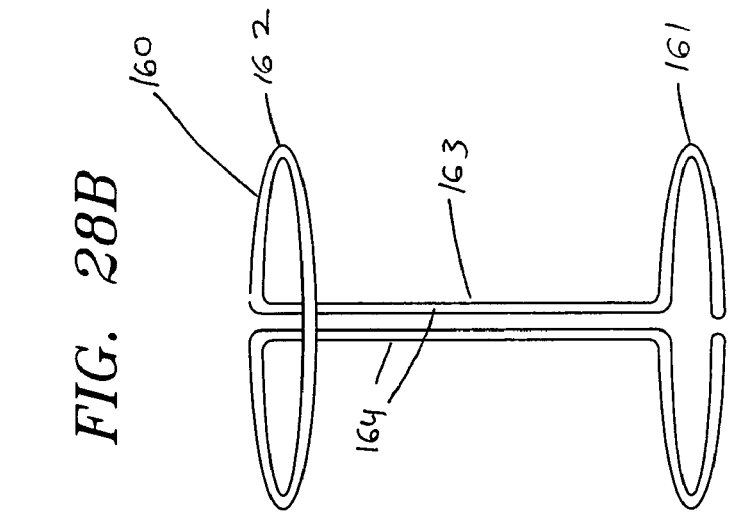
Figure 28A:
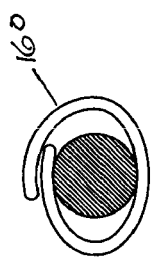
Figure 28C:
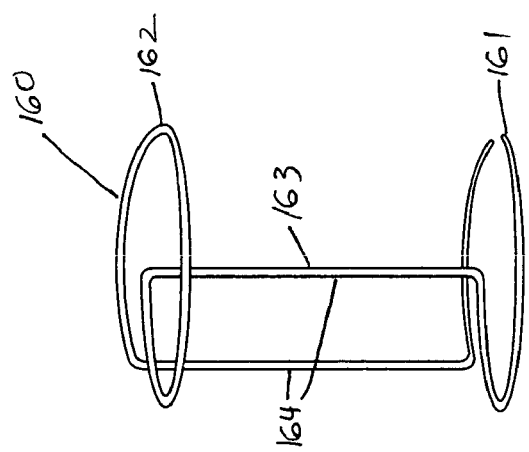

Yet another embodiment of a valve and anchoring structure according to the present invention is illustrated in FIGS. 27A through C. In the valve anchoring structure according to the present embodiment shown in FIGS. 27A and C, the valve (32) is supported by a tubular anchoring structure (150). The tubular anchoring structure (150) is preferably made of metal or plastic. The tubular anchoring structure (150) is also preferably designed to be expandable. For example, the anchoring structure may be designed to be self-expandable, balloon-expandable, or mechanically-expandable. The tab regions (35) of the valve (32) are preferably attached to the distal end (151) of the tubular anchoring structure (150) using staples, sutures, wire fasteners, or any other suitable means. The inflow rim (152) of the tubular anchoring structure may comprise a plurality of suture bores (153) to facilitate attachment of the valve (32). The tubular anchoring structure (150) also comprises vertical support posts (154) with axial slots (155) for the insertion of the valve tabs (35). The vertical support posts (154) extend to the distal end (151) of the tubular anchoring structure (150). In a preferred implementation of the of the present embodiment, the means of attachment, or an alternative means, is used to also attach the tab regions (35) of the valve (32) to the vascular wall thereby securing the valve (32) and tubular anchoring structure (150) in the valve sinuses. Such fastening means can also be optionally used at the inflow annulus to provide additional anchoring.

Another embodiment of a valve and anchoring structure according to the present invention is illustrated in FIG. 28. In the present embodiment, a dual-ring anchoring structure (160) is shown, as seen in FIGS. 28C and D, with an inflow ring (161) and an outflow ring (162) connected by a vertical element (163) comprised of two posts (164). The anchoring structure (160) is designed to be circumferentially collapsible as can be seen in FIGS. 28A and B. As shown in FIGS. 28C and D, the anchoring structure (160) is collapsed by sliding the two posts (164) that are adjacent to each other in the expanded state (FIG. 28D) past each other to decrease the circumference of the upper outflow (162) and lower inflow (161) rings (FIG. 28C). Thus, prior to implantation the anchoring structure (160) is collapsed and, once the valve is properly positioned in the valve sinuses, the anchoring structure freely self-expands to its original dimensions. The self-expanding behavior of the present embodiment is due to Nitinol's relatively high modulus of elasticity, which imparts superior spring-like properties to the anchoring structure. Alternatively, if the anchoring structure is constructed of a non-self expanding material, it may be mechanically collapsed and expanded using the devices disclosed herein.

Another embodiment of a valve and anchoring structure according to the present invention is illustrated in FIGS. 29A and B. In the present embodiment, a dual-ring anchoring structure (170) is shown, with an inflow ring (171) and an outflow ring (172) connected by a vertical element (173) comprised of two posts (174). The inflow rim may further comprise tissue mounting posts (175). The anchoring structure (170) is designed to be circumferentially collapsible. FIG. 29A shows how the posts (174) are separated in the expanded state and FIG. 29B shows how the posts (174) form a single vertical element (173) in the collapsed state. Thus, prior to implantation the anchoring structure is collapsed and upon the positioning of the valve assembly in the valve sinuses, the anchoring structure (170) freely self-expands to its original dimensions. As in the previous embodiment, the self-expanding behavior of the present embodiment is a function of Nitinol's high modulus of elasticity. Alternatively, if the anchoring structure is constructed of a non-self expanding material, it may be mechanically collapsed and expanded using the devices disclosed herein.

Figure 30A:
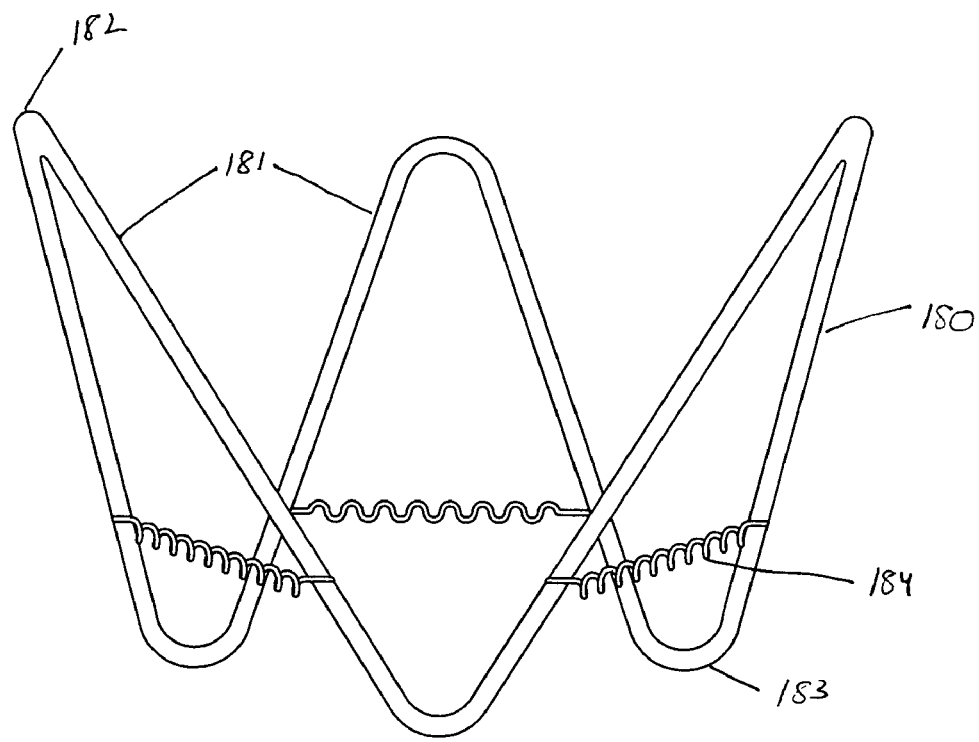
FIGS. 30A and B shows an anchoring structure comprising a three-member spring aided frame.
Figure 30B:
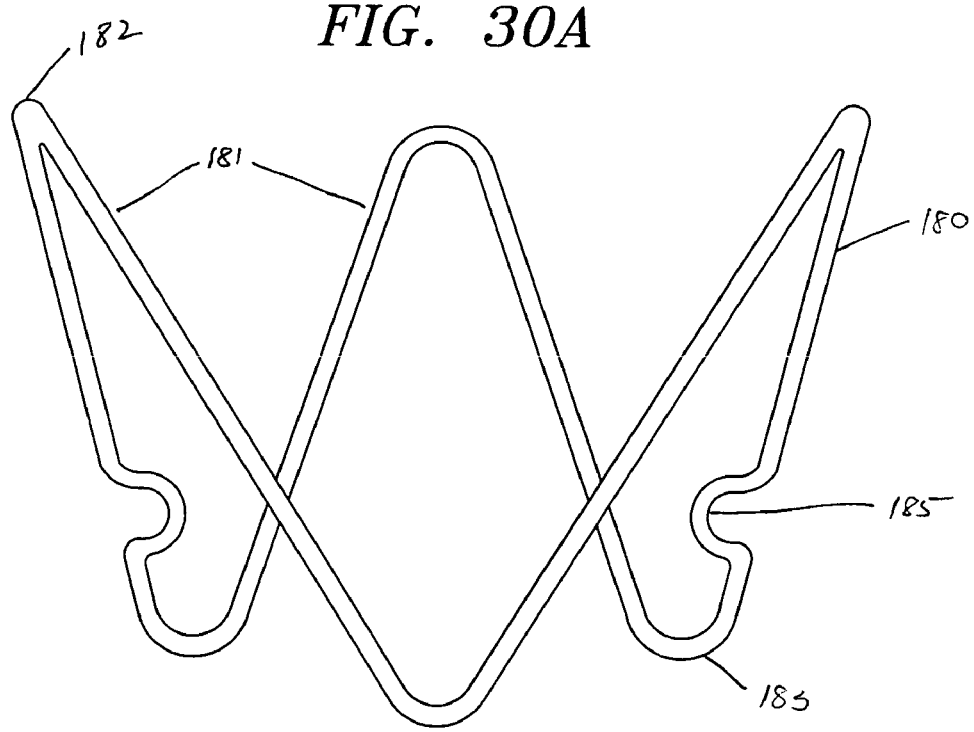

A further embodiment of a valve and anchoring structure according to the present invention is illustrated in FIGS. 30A and B. The present embodiment comprises a spring-aided anchoring structure (180). The spring aided anchoring structure (180) preferably comprises three members (181) that are radially collapsible for implantation into the valve sinuses. The members (181) comprise peaks (182) that serve as valve attachment points and valleys (183) that serve to lodge the anchoring structure at the valve sinus inflow annulus. Following implantation, the anchoring structure (180) is expanded to its original dimensions by coil springs (184) that provide an outward radial force on each member. In a preferred embodiment, shown in FIG. 30B, the spring aided anchoring structure (180) comprises at least one anchoring section (185) for selectively securing the anchoring structure (180) in the valve sinus at the inflow annulus. Although the present embodiment illustrates three members (181) and three coil springs (184), it should be appreciated that two or more members (181) with a corresponding number of coil springs (184) may be used.

The anchoring structures of the present invention may be constructed from superelastic memory metal alloys, such as Nitinol, described in U.S. Pat. No. 6,451,025, incorporated herein by reference. Nitinol belongs to a family of intermetallic materials which contain a nearly equal mixture of nickel and titanium. Other elements can be added to adjust or modify the material properties. Nitinol exhibits both shape memory and superelastic properties. The shape memory effect of Nitinol allows for the restoration of the original shape of a plastically deformed structure by heating it. This is a result of the crystalline phase change known as thermoelastic martensitic transformation. Thus, below the transformation temperature, Nitinol is martensitic, i.e. easily deformable. Heating the material converts the material to its high strength, austenitic condition. Accordingly, prior to implantation, the valve assembly is chilled in sterile ice water. Upon cooling, the Nitinol anchoring structure enters its martensite phase. Once in this phase, the structure is malleable and can maintain a plastically deformed crushed configuration. When the crushed anchoring structure comprising the valve is delivered into the valve sinus, the increase in temperature results in a phase change from martensite to austenite. Through the phase change, the anchoring structure returns to its memorized shape, and thus expands back to its original size.

The anchoring structures can also be designed to use the superelasticity properties of Nitinol. With the superelastic design, the chilling procedure would not be necessary. The anchoring structure would be crushed at room temperature. The phase change to martensite would be accomplished by means of the stress generated during the crushing process. The anchoring structure would be held in the crushed configuration using force. Force is removed once the anchoring structure is delivered to the valve sinus, resulting in a phase transformation of the Nitinol from martensite to austenite. Through the phase change, the anchoring structure returns to its memorized shape and stresses and strains generated during the crushing process are removed. Alternatively, the anchoring structures of the present invention may be composed of a non-self expanding suitable material, such as biocompatible metals, including titanium, and plastics. Whether the valve assembly is designed to be self-expandable or non-self expandable, it may be compressed (and expanded, if non-self expandable) for implantation using the expansion and contraction devices disclosed herein.

Expansion and Contraction Devices

Figure 31A:
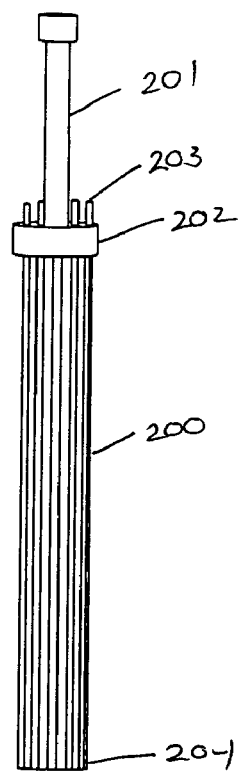
FIGS. 31A and B show a preferred embodiment of an expansion and contraction device.
Figure 31B:
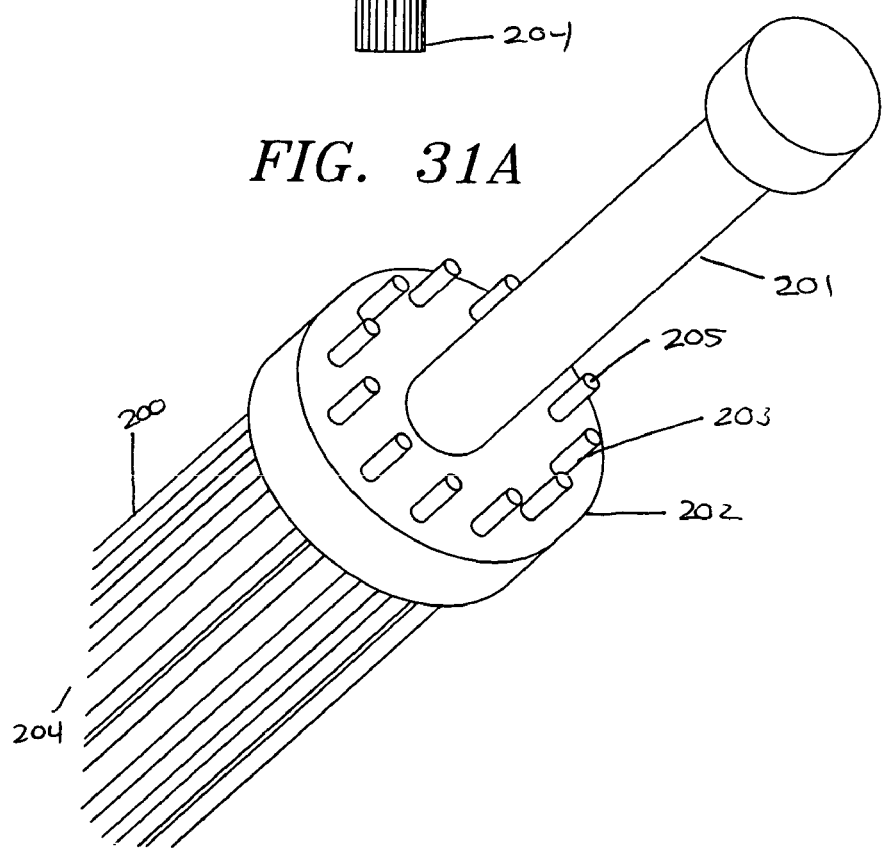
Figure 32A:
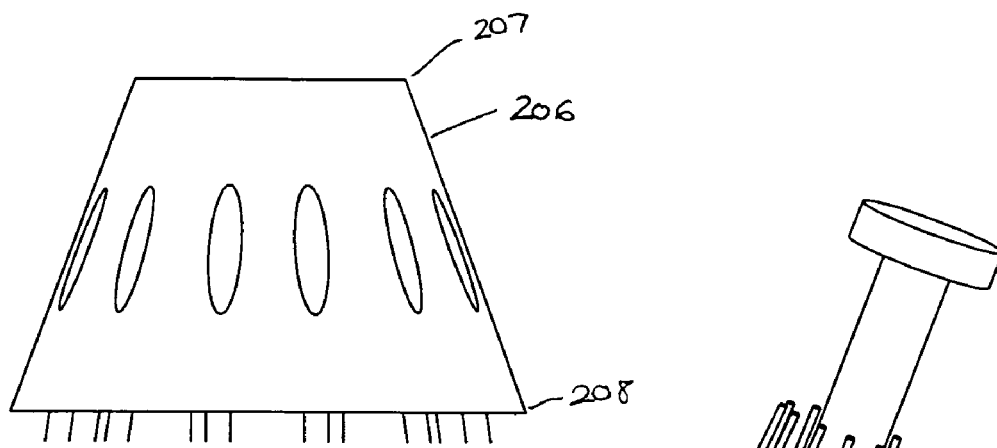
FIGS. 32A and B more particularly shows the angled wires of the device.
Figure 32B:
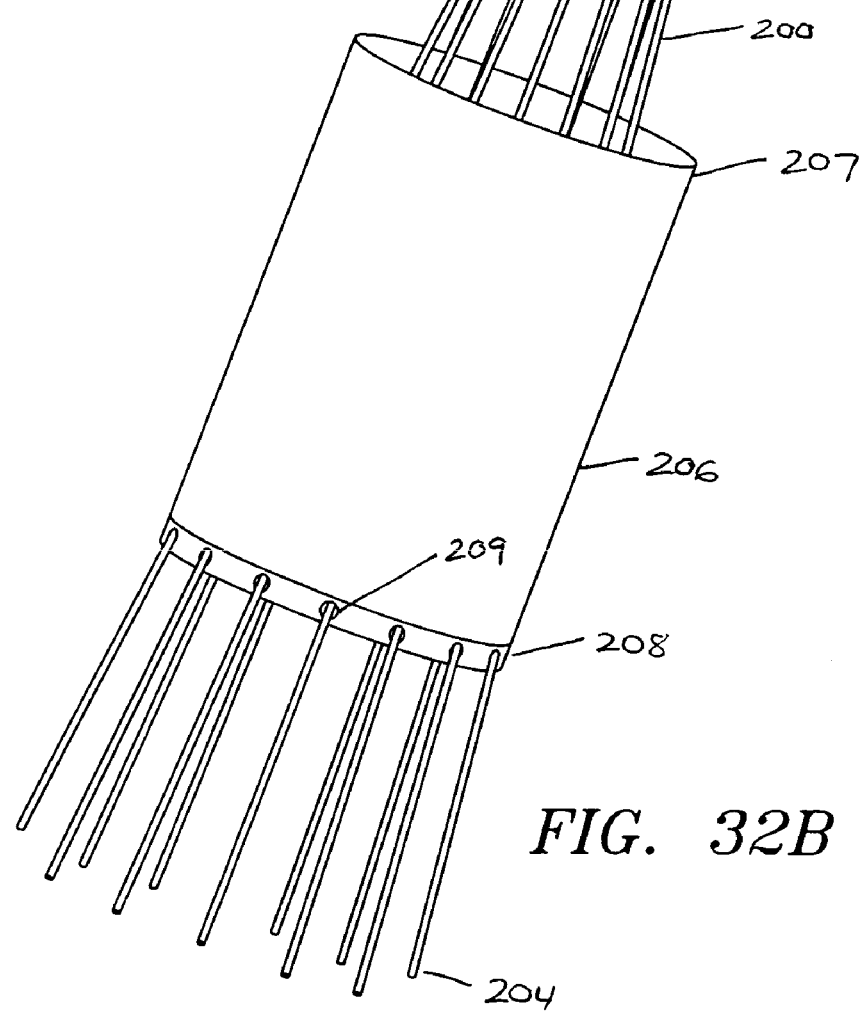
Figure 33:
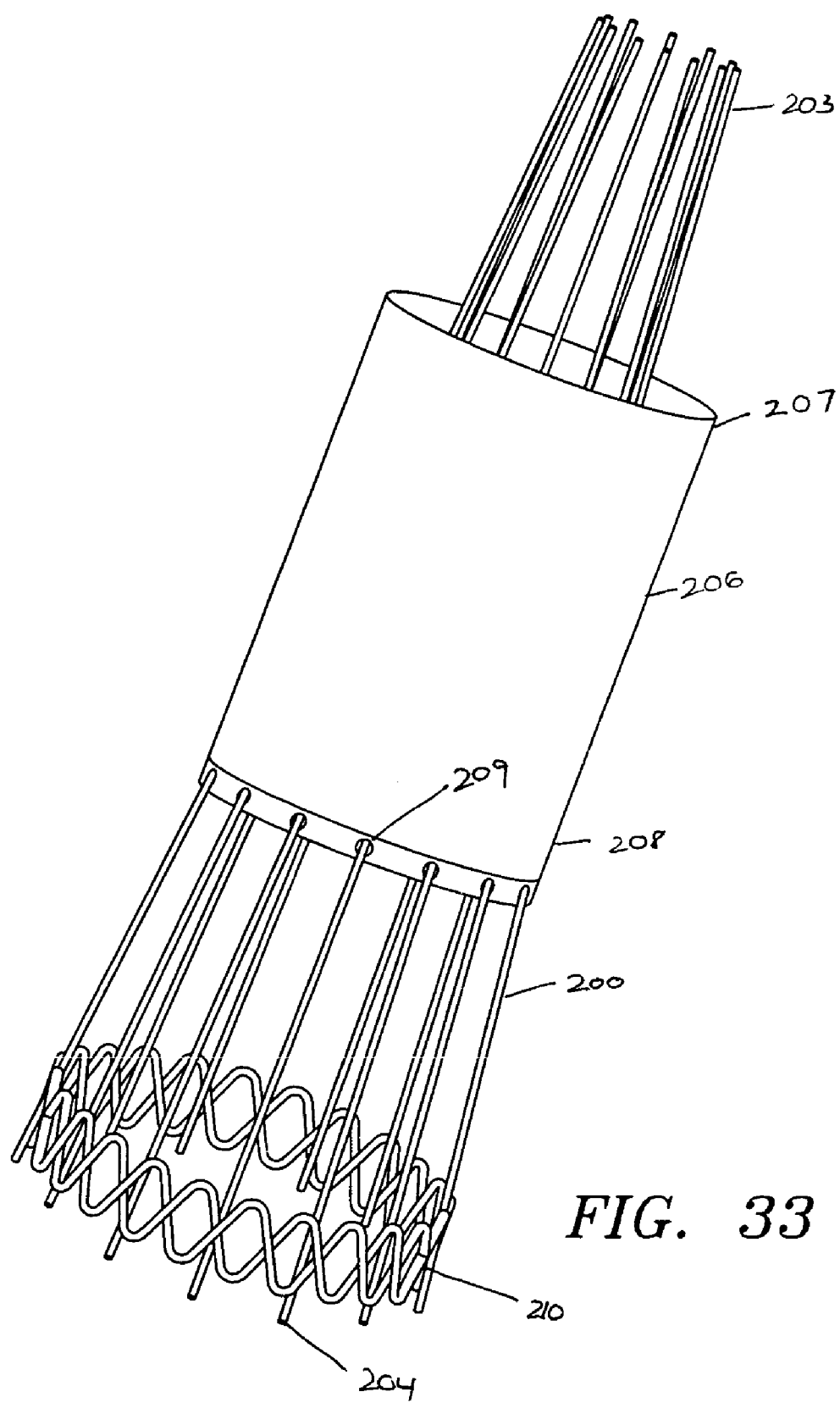
FIG. 33 shows the positioning of an anchoring structure on the expansion and contraction device.

A preferred embodiment of an expansion and contraction device for implanting the valve assemblies of the present invention is illustrated in FIGS. 31–33. As seen in FIGS. 31A and B, the device of the present embodiment comprises a group of bendable hollow tubes or wires (200), a grip handle (201), and a circular element (202) that holds the wires (200) together at their proximal ends (203). Each wire (200) comprises a proximal end (203), a distal end (204) and a hollow shaft (205) running from the proximal end (203) to the distal end (204). The wires (200) are attached to the grip handle (201) at their proximal ends (203) via the circular element (202) such that the wires form a circular pattern.

As shown in FIGS. 32A and B, the expansion and contraction device further comprises a cylinder (206) having a proximal end (207) and a distal end (208). The cylinder (206) has holes (209) drilled along its distal perimeter (208). The holes (209) in the cylinder (206) are preferably drilled at an outward angle so that by forcing the wires (200) through the angled holes (209), the distal ends (204) of the wires (200) are driven radially outward. As the wires (200) are pushed further through the outwardly angled cylinder holes (209), the further the wires (200) spread radially, thereby expanding the anchoring structure that is positioned over the wires (200). Accordingly, the angle of the cylinder holes (209) controls the relationship between the longitudinal movement of the wires (200) and their radial dilation.

As shown in FIG. 33, a representative anchoring structure (210) of the present invention is attached to the distal ends (204) of the hollow wires (200). The cylinder (206) having a proximal end (207) and a distal end (208) has holes (209) drilled along its distal perimeter (208). The holes (209) in the cylinder (206) are drilled at an outward angle so that by forcing the wires (200) through the angled holes (209), the distal ends (204) of the wires (200) are driven radially outward. As this figure shows, when the wires (200) are pushed further through the outwardly angled cylinder holes (209), they are forced to spread radially, thereby expanding the anchoring structure (210) that is positioned over the wires (200) at their distal ends (204). In a preferred embodiment, a long suture is routed from the proximal end to the distal end of the wire down its hollow shaft, looped around a segment of the anchoring structure at the distal end of the wire and then routed back to the proximal end of the wire, where it is secured. Attached to the distal ends (204) of the hollow wires, the anchoring structure (210) contracts and expands radially in response to the longitudinal motion of the wires (200). Pulling the grip handle (201) proximally contracts the anchoring structure (210) into a collapsed state for implantation whereas pushing the grip handle (201) distally expands the anchoring structure (210). When the anchoring structure (210) is positioned in a desirable location in the vessel and expanded to the desired dimensions, the sutures are severed and removed from the proximal end (203) of the wires (200) in order to disconnect the anchoring structure (210) from the device. The device of the present embodiment is removed, thereby leaving the valve assembly securely situated in the valve sinus.

Figure 34:
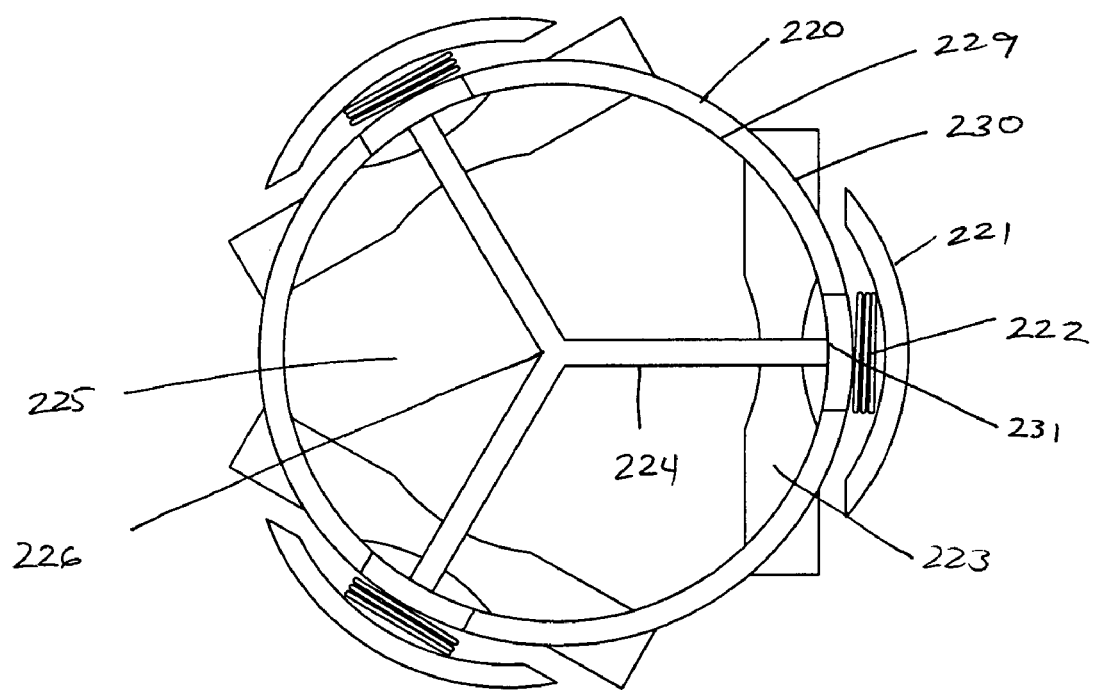
FIG. 34 shows another preferred embodiment of an expansion and contraction device featuring a wire-spindle mechanism.
Figure 35:
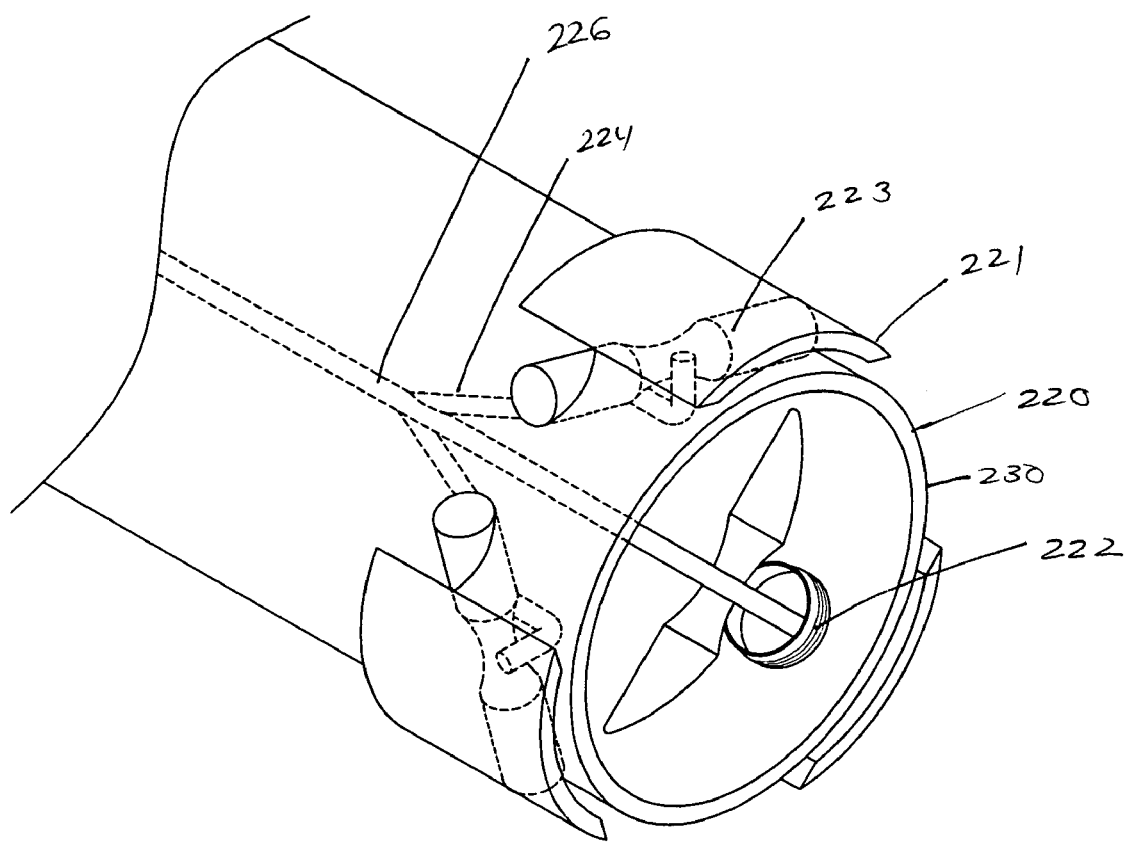
FIG. 35 shows a different perspective of the wire-spindle expansion and contraction device.

Another expansion and contraction device is illustrated in FIGS. 34 and 35. As shown in FIG. 34, the device of the present embodiment comprises a tube (220), multiple wall panels (221), springs (222) corresponding to the multiple wall panels (221), a spindle (223) and a plurality of connecting wires (224). The tube (220) comprises a hollow shaft (225) having a radial center (226), a proximal end (227), a distal end (228) as shown in FIG. 35, an interior wall (229) and an exterior wall (230), wherein a hole (231) corresponding to each wall panel (221) extends through the interior (229) and exterior wall (230) of the tube (220). In a preferred embodiment, the perimeter of the exterior wall (230) is surrounded by adjacent wall panels (221), only buffered by the springs (222) corresponding to the wall panels (221). The spindle (223) is attached to the interior wall (229) of the tube (220), preferably facing the tube's (220) radial center (226). A connecting wire (224) is attached to each wall panel (221) and routed through the spring (222) and the corresponding hole (231) in the tube wall (229, 230) to meet the other connecting wires (224), preferably at the radial center (226) of the tube (220).

As shown in FIG. 35, upon meeting at the radial center (226) of the tube (220), the wires (224) having been wrapped around the spindle (223), now run parallel to the tube's (220) longitudinal axis. By pulling the wires (224) proximally, the attached panels (221) compress the springs (222) against the tube's (220) exterior wall (230). In this compressed state, a collapsed valve assembly of the present invention can be placed over the panels (221). Once the device of the present embodiment, loaded with the valve assembly, is positioned at the desired location in the valve sinus, the tension in the wires (224) is relieved to force the wall panels (221)

outward, thereby expanding the anchoring structure and valve. The length of the uncompressed spring (222) determines the diameter to which the anchoring structure can be expanded. The anchoring structure can optionally be secured to the wall panels (221), by staples, sutures, wire fasteners, or any other suitable means, so that the valve assembly may be selectively expanded and collapsed by preferably varying the tension on the connecting wires.

Figure 36A:
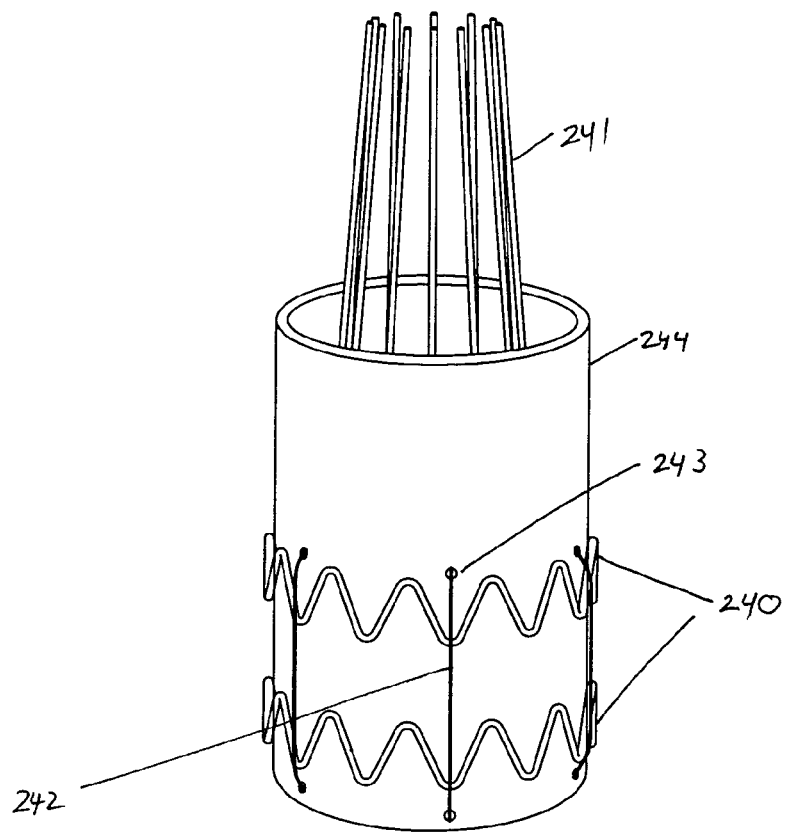
FIGS. 36A and B show another preferred embodiment of an expansion and contraction device for self-expanding valve assemblies.
Figure 36B:
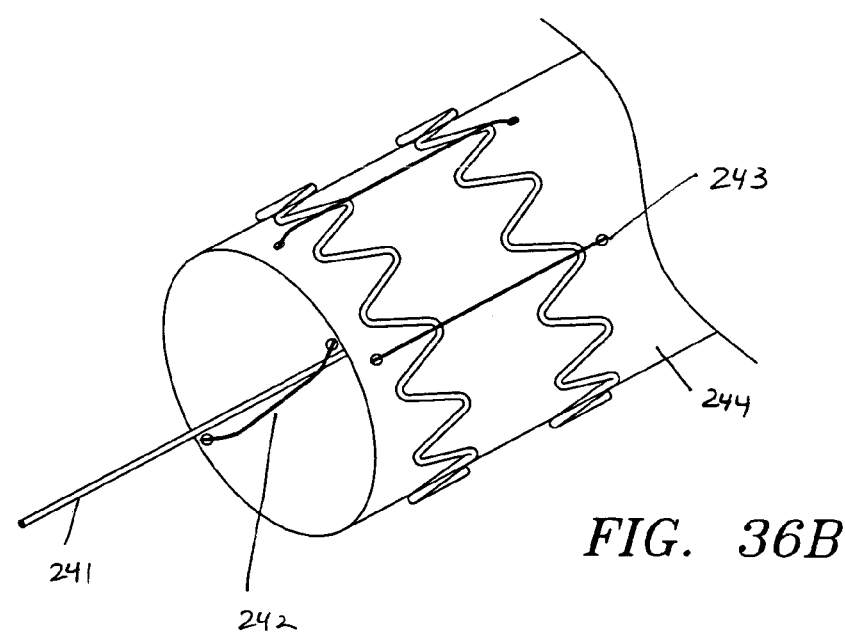

In FIGS. 36A and B, another preferred embodiment of an expansion and contraction device of the present invention is presented. In this embodiment, the anchoring structure (240) is composed of a shape memory metal or the like having a relatively high modulus of elasticity, and possessing an outward spring-like force when in a compressed state. Therefore, spring loaded wall panels are not necessary in the present embodiment. Instead, the wires (241) pass through sutures (242) that are threaded through holes (243) in the tube (244) wall and wrap around portions of the anchoring structure. Thus, the wires (241) keep the anchoring structure (240) compressed by pulling the sutures (242) around the anchoring structure (240) against the tube (244). Alternatively, the tube structure can be omitted with only the wires (241) and sutures (242) keeping the anchoring structure (240) in a compressed state. This would ensure that the valve within the anchoring structure is not contacted by any mechanical elements, such as a tube (244). Alternatively, the tube could be made from a cloth- or tissue-like material. Once the anchoring structure (240) is positioned in the desired location in the valve sinus, the wires (241) can be retracted, allowing the anchoring structure (240) to self-expand such that the tube (244) can be withdrawn, leaving the anchoring structure (240) securely lodged at the desired location of implantation. The sutures (242), which will remain wrapped about the anchoring structure (240), can be made of biodegradable material and thus will be resorbed by the body within a matter of days.

Figures 37A, 37B, 37C:
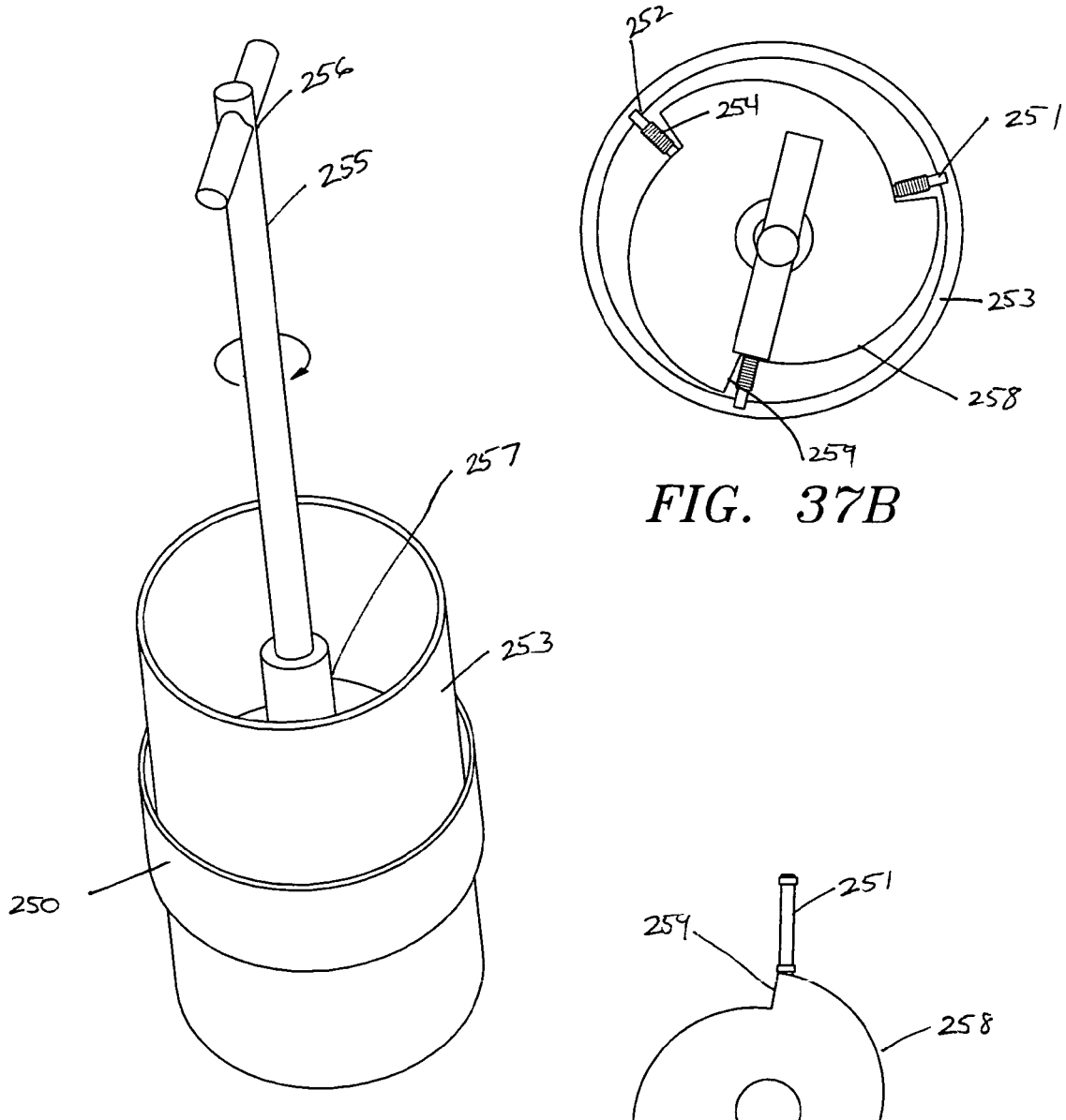
FIG. 37A shows a further preferred embodiment of an expansion and contraction device featuring a rotating plate mechanism.
FIGS. 37B and C more particularly shows the spiral-shaped rotating plate.
Figure 38A:
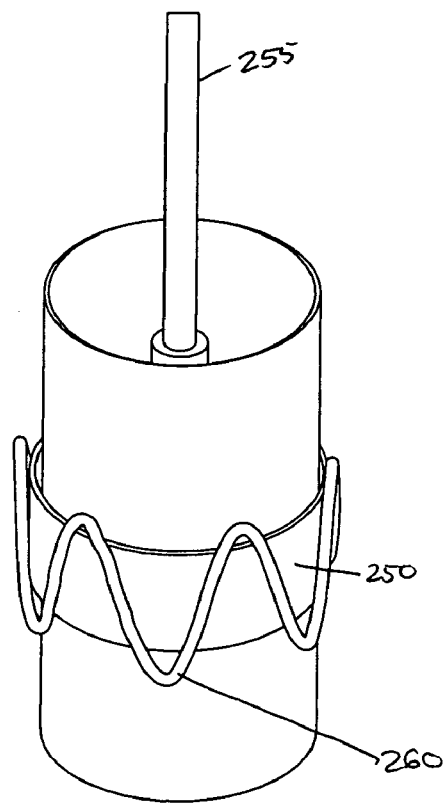
FIGS. 38A and B show the expansion and contraction device expanding an anchoring frame.
Figure 38B:
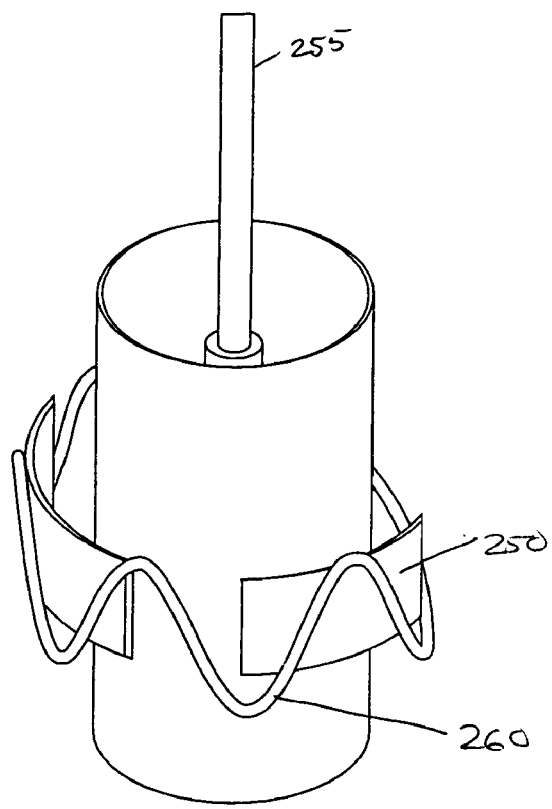

The contraction and expansion device illustrated in FIGS. 37 and 38 represents another preferred embodiment of the present invention. As illustrated in FIG. 37, each wall panel (250) is connected to a pin (251) which runs through the corresponding hole (252) in the tube (253) wall. The pin (251), protruding radially inward from the tube's interior, is preferably spring-loaded (254) toward the radial center of the tube (253). In a zero energy state, the wall panels (250) rest against the exterior wall of the tube (253) and the collapsed anchoring structure rests against the wall panels (250). Instead of wires, the present embodiment comprises a longitudinal shaft (255) running through the radial center of the tube. The shaft is comprised of a proximal end (256) and a distal end (257). The distal end (257) is connected to a central plate (258) having spiral shaped edges (259) as shown in FIGS. 37B and C. The central plate (258) is located in the tube (253), parallel to the tube's cross-section and is aligned with the spring-loaded (254) pins (251). The plate's spiral-shaped edges (259) preferably cause the distance from the plate's perimeter to the tube's radial center to vary along the plate's (258) perimeter. When the shaft (255) is rotated, the edge of the plate (259) pushes against each pin (251), thereby driving the corresponding panels (250) outward and expanding the anchoring structure, as FIG. 37C shows.

FIGS. 38A and B show how rotation of the shaft (255) pushes the wall panels (250) radially out, thereby expanding the anchoring structure (260). In a preferred embodiment, the anchoring structure (260) is sutured to the wall panels (250) to allow expansion and contraction of the anchoring structure by alternating rotation of the shaft. The sutures are preferably removable from the shaft's (255) proximal end to free the valve assembly from the device following implantation in the valve sinus.

Figure 39:
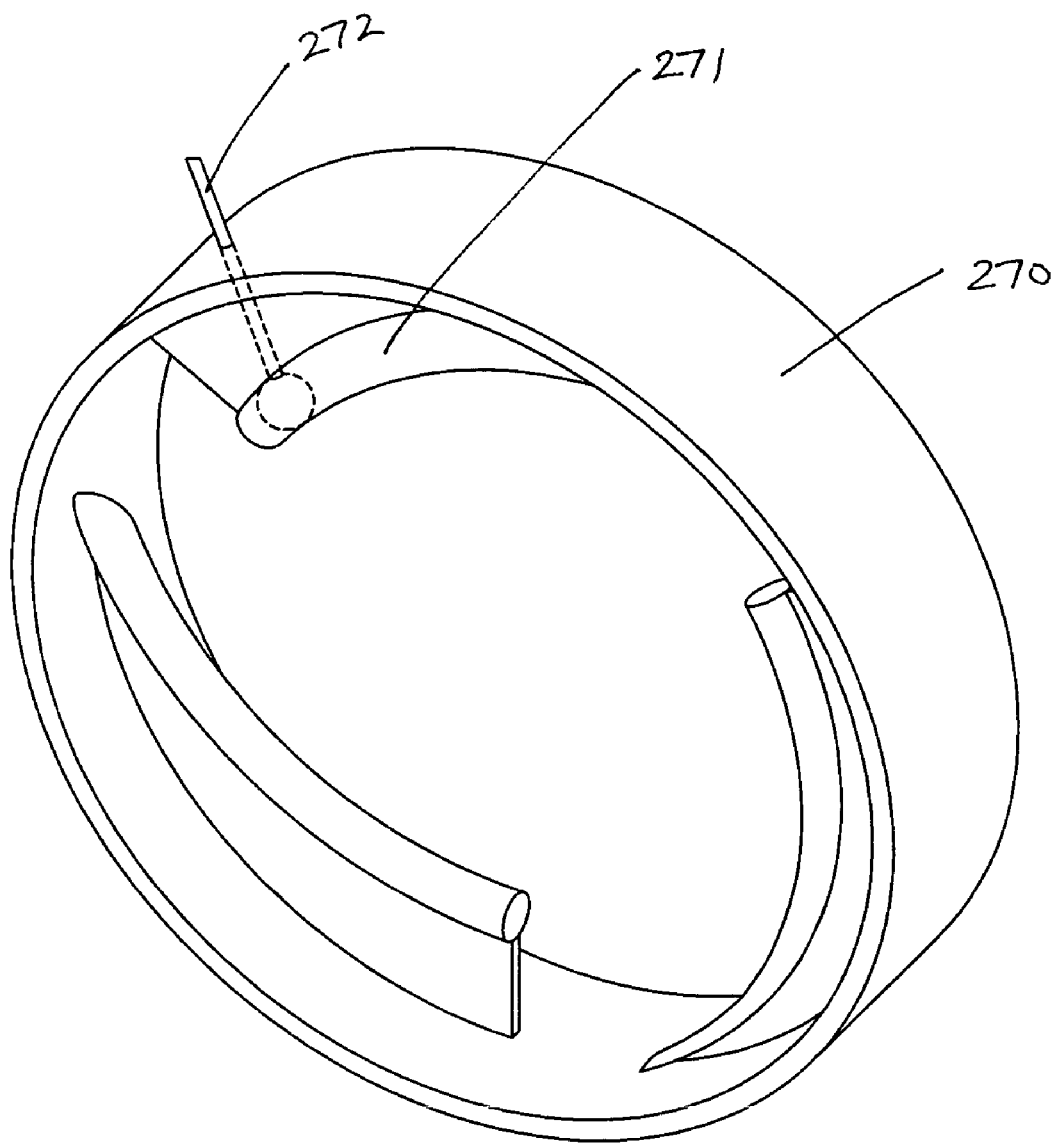
FIG. 39 shows another preferred embodiment of an expansion and contraction device featuring a groove-pin mechanism.

In still another embodiment, as illustrated in FIG. 39, an expansion and contraction device similar to the previous embodiment is presented. Instead of a device comprising a central plate with spiral-shaped edges of varying dimensions, the present preferred embodiment utilizes a circular disk (270) with pre-cut spiral-shaped grooves (271) corresponding to the spring-loaded pins (272). Preferably, the grooves (271) provide a track of varying depth for the pins (272) such that the pins (272) are forced radially outward upon rotation of the disk (270), thereby expanding the anchoring structure.

Adhesive Means for Securing Replacement Valves

In addition to the disclosed features and mechanisms for securing the valve assembly comprising a valve and anchoring structure into position, the present invention provides the use of biocompatible adhesives. A number of adhesives may be used to seal the valve assembly to the surrounding tissue in the valve sinus. The following are examples of available adhesives and methods of use:

U.S. Pat. No. 5,549,904, the entire contents of which are incorporated herein by reference, discloses a formulated biological adhesive composition comprising tissue transglutaminase and a pharmaceutically acceptable carrier, the tissue transglutaminase in an effective amount to promote adhesion upon treatment of tissue in the presence of a divalent metal ion, such as calcium or strontium. In operation, the two components are mixed to activate the sealable fixation means for securely fixing the valve assembly to tissue at a desired valve location.

U.S. Pat. No. 5,407,671, the entire contents of which are incorporated herein by reference, discloses a one-component tissue adhesive containing, in aqueous solution, fibrinogen, F XIII, a thrombin inhibitor, prothrombin factors, calcium ions and, where appropriate, a plasmin inhibitor. This adhesive can be reconstituted from a freeze-dried form with water. It can contain all active substances in pasteurized form and is then free of the risk of transmission of hepatitis and HTLV III. In operations, the one-component tissue adhesive is reconstituted from a freeze-dried form with water to activate the sealable fixation means for securely fixing the valve assembly to tissue at a desired valve location.

U.S. Pat. No. 5,739,288, the entire contents of which are incorporated herein by reference, discloses a method for utilizing a fibrin sealant which comprises: (a) contacting a desired site with a composition comprising fibrin monomer or noncrosslinked fibrin; and (b) converting the fibrin monomer or noncrosslinked fibrin to a fibrin polymer concurrently with the contacting step, thereby forming a fibrin clot. In operation, the fibrin monomer or noncrosslinked fibrin is converted to activate the sealable fixation means for securely fixing the valve assembly to tissue at a desired valve location.

U.S. Pat. No. 5,744,545, the entire contents of which are incorporated herein by reference, discloses a method for effecting the nonsurgical attachment of a first surface to a second surface, comprising the steps of: (a) providing collagen and a multifunctionally activated synthetic hydrophilic polymer; (b) mixing the collagen and synthetic polymer to initiate crosslinking between the collagen and the synthetic polymer; (c) applying the mixture of collagen and synthetic polymer to a first surface before substantial crosslinking has occurred between the collagen and the synthetic polymer; and (d) contacting the first surface with the second surface to effect adhesion between the two surfaces. Each surface can be a native tissue or implant surface. In operation, collagen and a multifunctionally activated synthetic hydrophilic polymer are mixed to activate the sealable fixation means for securely fixing the valve assembly to tissue at a desired valve location.

U.S. Pat. No. 6,113,948, the entire contents of which are incorporated herein by reference, discloses soluble microparticles comprising fibrinogen or thrombin, in free-flowing form. These microparticles can be mixed to give a dry powder, to be used as a fibrin sealant that is activated only at a tissue site upon dissolving the soluble microparticles. In operation, soluble microparticles comprising fibrinogen or thrombin are contacted with water to activate the sealable fixation means for securely fixing the valve assembly to tissue at a desired valve location.

U.S. Pat. Nos. 6,565,549, 5,387,450, 5,156,911 and 5,648,167, the entire contents of which are incorporated herein by reference, disclose a thermally activatable adhesive. A "thermally activatable" adhesive is an adhesive which exhibits an increase in "tack" or adhesion after being warmed to a temperature at or above the activation temperature of the adhesive. Preferably, the activation temperature of the thermally activatable adhesive is between about 28° C. and 60° C. More preferably, the activation temperature is between about 30° C. and 40° C. One exemplary thermally activatable adhesive is described as Example 1 in U.S. Pat. No. 5,648,167, which is incorporated by reference herein. It consists of a mixture of stearyl methacrylate (65.8 g), 2-ethylhexyl acrylate (28.2 g) and acrylic acid (6 g) monomers and a solution of catalyst BCEPC (0.2 g) in ethyl acetate (100 g) is slowly added by means of dropper funnels to ethyl acetate (50 g) heated under reflux (80 degrees C.) in a resin flask over a period of approximately 6 hours. Further ethyl acetate (50 g) is added to the mixture during the polymerization to maintain the mixture in a viscous but ungelled state. In operation, thermally activatable adhesive is heated to activate the sealable fixation means for securely fixing the valve assembly to tissue at a desired valve location.

Figure 40:
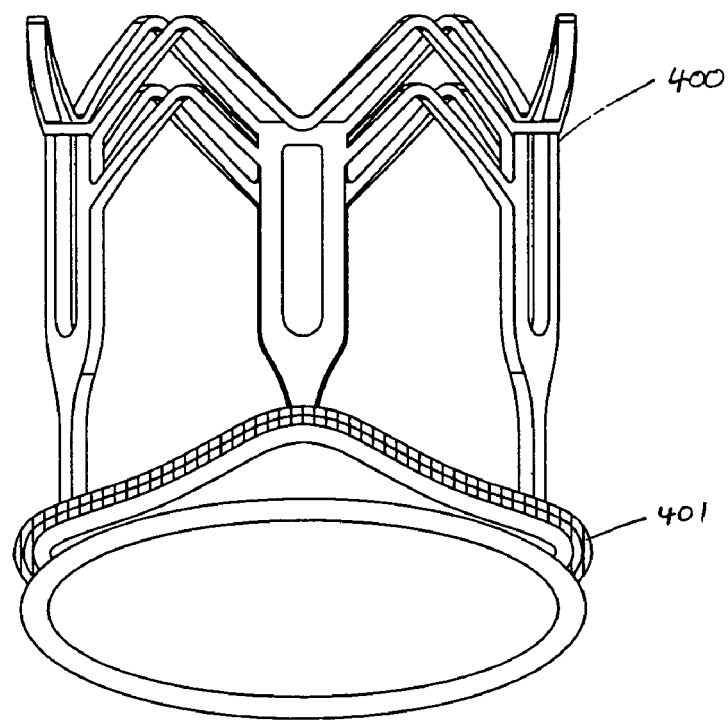
FIG. 40 shows one preferred embodiment of a valve having an outer circumferential reservoir containing a sealable fixation means for securely fixing the valve prosthesis at a desired location within a vessel or body cavity.

FIG. 40 shows a preferred embodiment, wherein an outer circumferential reservoir (401) is located at an outermost radius of a valve anchoring structure (400) when the anchoring structure (400) is in an expanded state, wherein the reservoir is filled with a sealable fixation means for securely fixing the valve assembly (400) at a desired location within a body cavity. FIG. 40 further illustrates one embodiment of the reservoir (401) comprising a sealable fixation means, wherein the sealable fixation means may comprise a one-component biological adhesive. The sealable fixation means may be activated by exposing the biological adhesive to blood or heat.

Figure 41A:
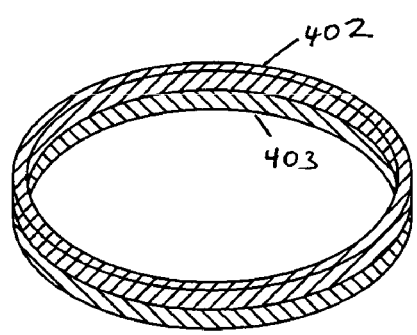
FIGS. 41A and B show another embodiment of a valve having an outer circumferential reservoir, wherein the sealable fixation means comprises a two component biological adhesive.
Figure 41B:
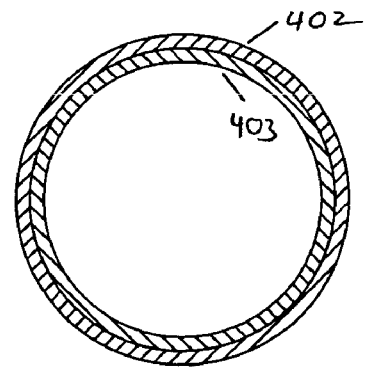

FIG. 41 illustrates another preferred embodiment wherein the sealable fixation means may comprise a two-component biological adhesive. The sealable fixation means may be activated by mixing the two components. Thus, for example, if one reservoir (402) contains microparticles that are activated by contact with water, the second reservoir (403) would contain the water for the activation of the microparticles. This figure also shows that the reservoirs may be arranged concentrically as shown in FIG. 41B or adjacent to each other as shown in FIG. 41A.

Figure 42:
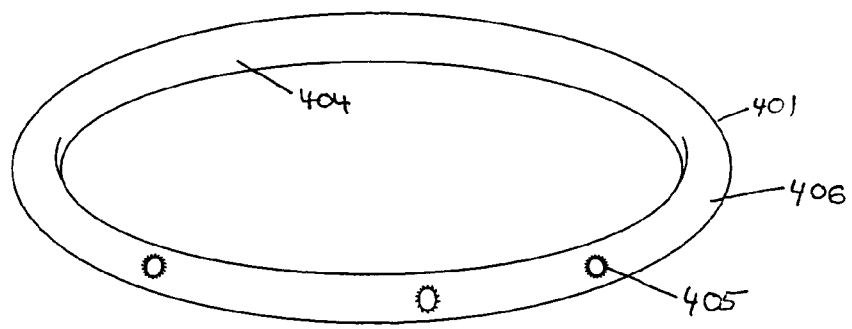
FIG. 42 illustrates a reservoir with thin spots adapted to rupture when the reservoir is under pressure, thereby releasing the contents of the reservoir.

FIG. 42 illustrates an exemplary reservoir (401) which may be attached to the valve anchoring structure by its inner wall (404) by sutures, glue, staples or some other appropriate method. FIG. 42 further illustrates a thin spot (405) on the outer wall (406) of the reservoir (401). The thin spots (405) are areas on the reservoir (401) that are adapted to rupture when placed under certain levels of pressure. The pressure is exerted on the thin spots (405) as the reservoir (401) is expanded along with the valve anchoring structure. The thin spots (405) are unable to withstand the pressure and therefore rupture releasing the contents of the reservoir (401) or reservoirs. In a preferred embodiment, the reservoir (401) is made of an elastic material that expands along with the expansion of the valve anchoring structure.

Figure 43:
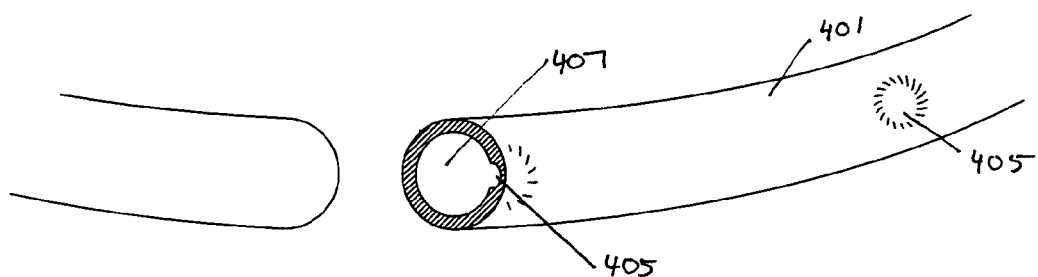
FIG. 43 is a cross-sectional view of the reservoir showing the thin spots.

FIG. 43 illustrates a cross sectional view of the reservoir (401). The reservoir (401) may contain a lumen (407) which extends along at least a portion of the circumference of the reservoir. The reservoir (401) has one or more thin spots (405) along its outermost circumference, wherein the thin spots (405) are sized and configured to rupture when the reservoir (401) is expanded to an appropriate diameter. When the anchoring structure comprising the valve is fully expanded, the pressure exerted upon the expanded thin spots (405) causes them to rupture. In still another preferred embodiment, the reservoir (401) is made of a biodegradable material adapted for erosion or rupture to release the content of the reservoir (401) and activate the sealable fixation means in a desired timeframe after implantation. In a further preferred embodiment, a circumferentially outermost portion is pressure sensitive to rupture, wherein the contents of the reservoir (401) are released when the reservoir (401) is compressed against the sinus cavities during expansion and implantation of the valve assembly.

Figure 44:
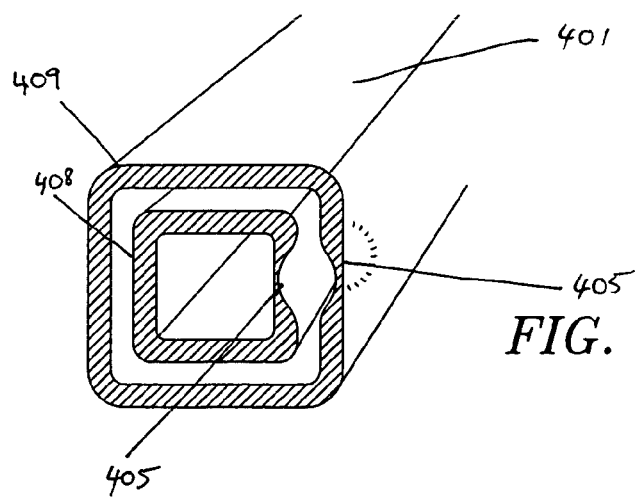
FIG. 44 is a cross-sectional view of a valve reservoir having two concentric component compartments.

FIG. 44 shows a cross-sectional view of another preferred embodiment, illustrating thin spots (405) on a reservoir having two concentric component compartments, an inner compartment (408) and an outer compartment (409). Component A in an inner compartment (408) and component B in an outer compartment (409) are to be mixed to form adhesive for sealing the valve assembly against the valve sinuses. The inner compartment (408) has a plurality of thin spots (405) along its outermost circumference, wherein the thin spots (405) are sized and configured to rupture when the reservoir (401) is expanded to an appropriate diameter. The outer compartment (409) also has a plurality of thin spots (405) along its innermost circumference. The thin spots (405) of the inner compartment (408) and the thin spots (405) of the outer compartment (409) may be located adjacent to each other. In one preferred embodiment, the space between the adjacent pair of thin spots (405) on the inner (408) and outer (409) compartment may comprise a piercing element that is activated to rupture the thin spot or the pair of adjacent spots when the reservoir is expanded to an appropriate diameter or a predetermined diameter. Other embodiments of reservoir configuration, for example, two parallel compartments circumferentially or longitudinally, and suitable activation mechanism for the sealable fixation means are also within the scope of the present invention.

The present invention further comprises methods and devices for the sizing of native valves that require replacement.

Methods and Apparatus for Valve Sizing

Figure 45A:
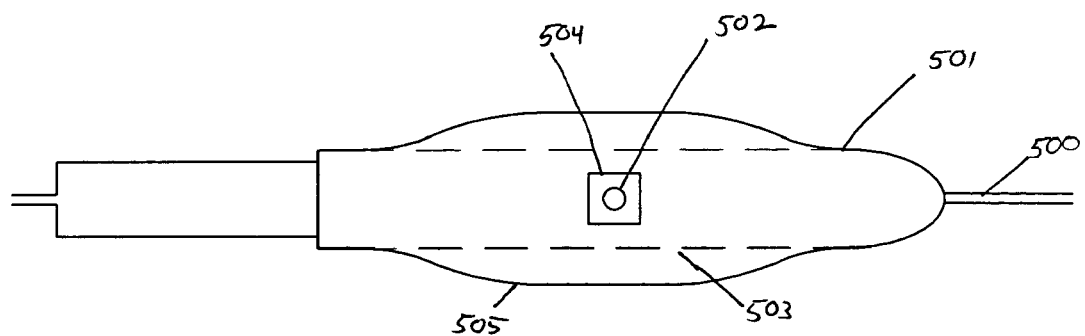
FIGS. 45A and B depict a minimally-invasive valve replacement sizer.
Figure 45B:
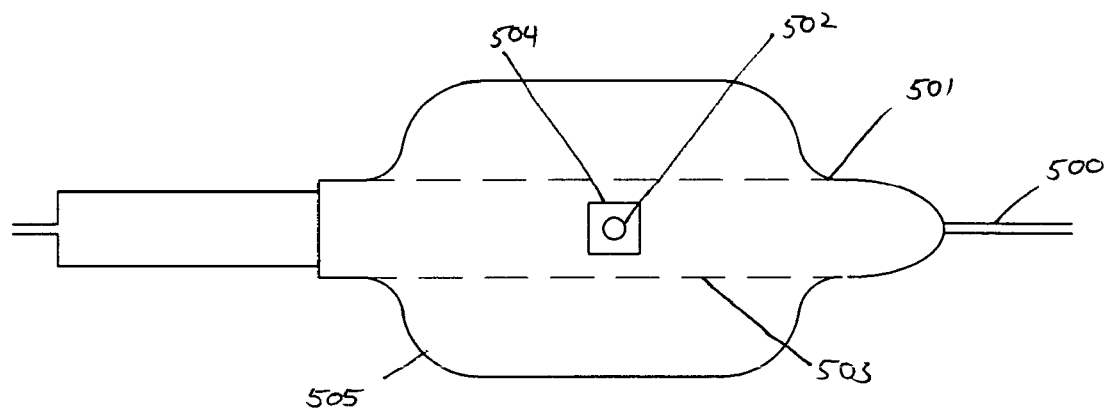

Intravascular ultrasound (IVUS) uses high-frequency sound waves that are sent with a device called a transducer. The transducer is attached to the end of a catheter, which is threaded through a vein, artery, or other vessel lumen. The sound waves bounce off of the walls of the vessel and return to the transducer as echoes. The echoes can be converted into distances by computer. A preferred minimally invasive valve replacement sizer is shown in FIGS. 45A and B. For purposes of this application, the distal end or portion refers to the area closer to the body while the proximal end or portion refers to the area closer to the user of the valve replacement sizer. The device comprises a guidewire (500), an intravascular ultrasound (IVUS) catheter (501) having a transducer (502), and a balloon dilatation catheter (503) all positioned within the central lumen of a catheter. The transducer (502) is positioned in the IVUS sizing window (504) of the balloon catheter. The guide wire (500) advances and guides the catheter (501) to the appropriate location for valve sizing. FIG. 45A shows the catheter in deflated form, whereas in FIG. 45B the balloon dilatation catheter (503) has inflated the balloon (505).

Figure 46:
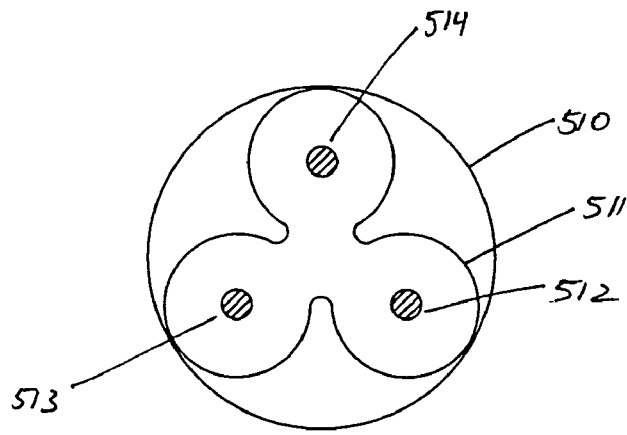
FIG. 46 is a cross-sectional view of a minimally-invasive valve replacement sizer comprising a guidewire, an intravascular ultrasound (IVUS) catheter having a transducer, and a balloon catheter, all positioned within the central lumen of the catheter.

In a preferred embodiment, shown in FIG. 46, the catheter (510) contains multiple lumens (511) in order to house a guidewire (512), an IVUS catheter (513), and a balloon dilatation catheter (514). FIG. 46 illustrates a cross sectional view. One of the separate lumens (511) contains the guidewire (512), another contains the IVUS catheter (513), and another contains the balloon dilatation catheter (514). The balloon dilatation catheter (514) has a balloon (515) attached circumferentially surrounding the balloon dilatation catheter (514) as well as a portion of the catheter (510).

Figure 47:
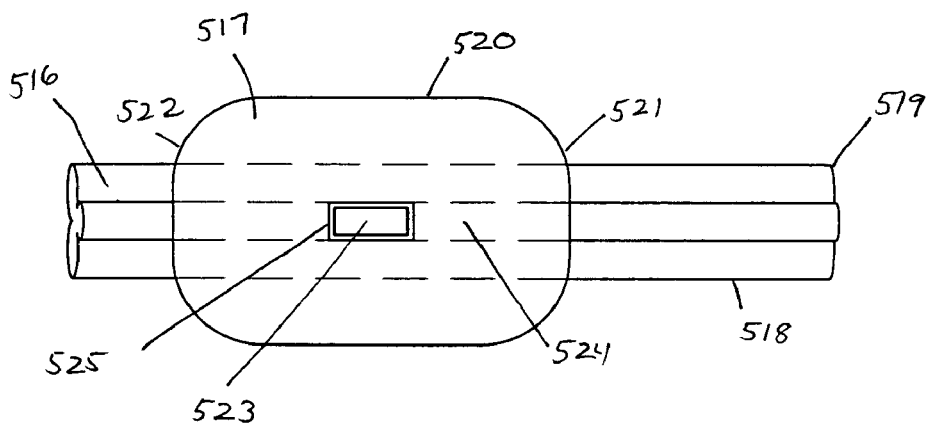
FIG. 47 shows a balloon catheter comprising a balloon that circumferentially surrounds a portion of the catheter at its distal portion.

FIG. 47 shows a balloon dilatation catheter (516) comprising a balloon (517) that circumferentially surrounds a portion of the catheter (518) proximal to its distal portion (519). More specifically, the balloon (517) comprises an outer wall (520) that circumferentially surrounds a portion of the catheter (518) near its distal portion (519). The balloon (517) also has a distal end (521) and a proximal end (522). In a preferred embodiment, within the area encompassed by the balloon, a transducer (523) is located on the IVUS catheter (524). Directly over the transducer (523) a sizing window (525) is placed on the IVUS catheter (524) to enable signals to be transmitted and received by the transducer (523) without interference. In a preferred embodiment, the sizing window (525) is simply an empty space. However, the sizing window (525) could be made from any substance which does not interfere with the signals emitted and received by the transducer (523).

Figure 48:
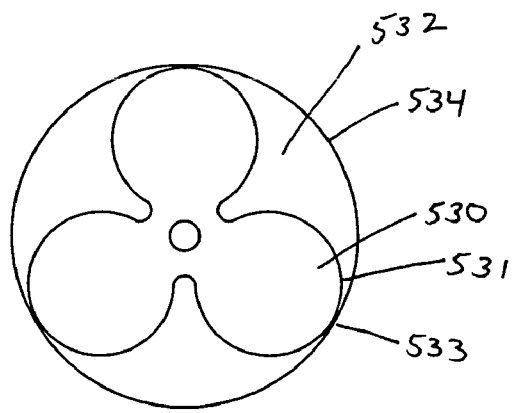
FIG. 48 shows a cross-sectional view of an inflated balloon with curves forming leaflets to enable fluid to pass.

Preferably, the balloon (517) is round but other shapes are possible and contemplated for use with the valve sizing apparatus. In particular, FIG. 48 shows a cross section of an inflated balloon (530) with curves forming leaflets (531) to enable fluid (532) to pass through the vessel while the balloon (530) is in its inflated state and the outer edges (533) of the leaflets (531) are in contact with the vessel wall (534) to measure the diameter. The balloon may further be made from compliant or non-compliant material.

Figure 49:
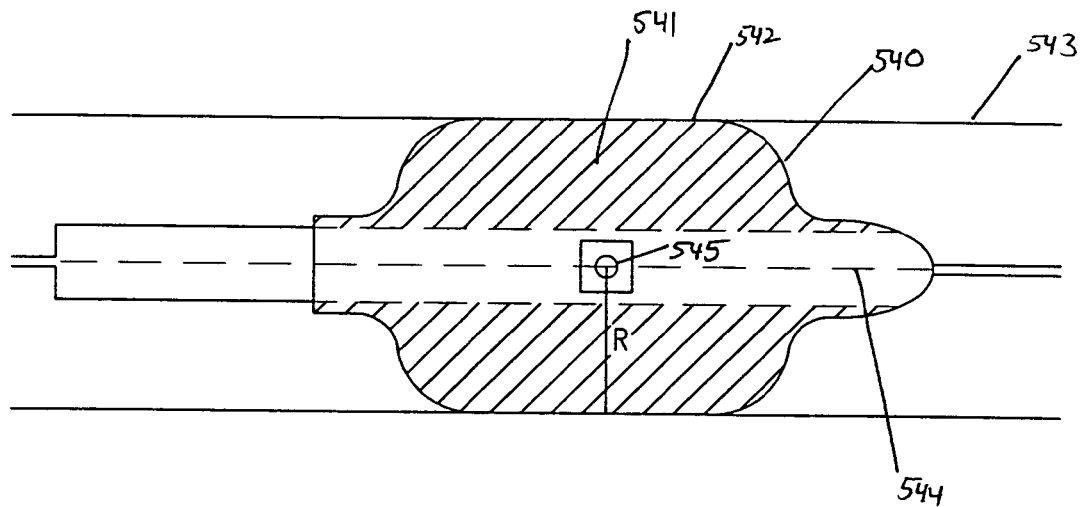
FIG. 49 shows one preferred embodiment of a minimally-invasive valve replacement sizer, wherein the balloon is inflated with saline.

FIG. 49 shows a preferred embodiment wherein the balloon (540) is inflated with saline (541). Preferably, the saline is pumped into the balloon (540) through the balloon dilatation catheter. Alternatively, the balloon (540) may be inflated with a gas or any other suitable substance. The balloon (540) is inflated to a chosen pressure by the person using the valve replacement sizer. When the balloon (540) has been inflated, the outermost portion of the outer wall (542) will be in contact with the vessel wall (543) or other lumen at the location where the replacement valve is to be placed. When the balloon (540) is completely inflated, the farthest radial points of the balloon's outer wall (542) will be equidistant to the center of the catheter (544). This distance is labeled as R. The transducer (545) may or may not be at the centermost point of the inflated balloon (540). Any deviation from the centermost point by the transducer (545) may be accounted for when calculating the diameter of the vessel lumen. However, the signal emitted by the transducer (545) preferably intersects the balloon (540) at its greatest radius.

Figure 50:
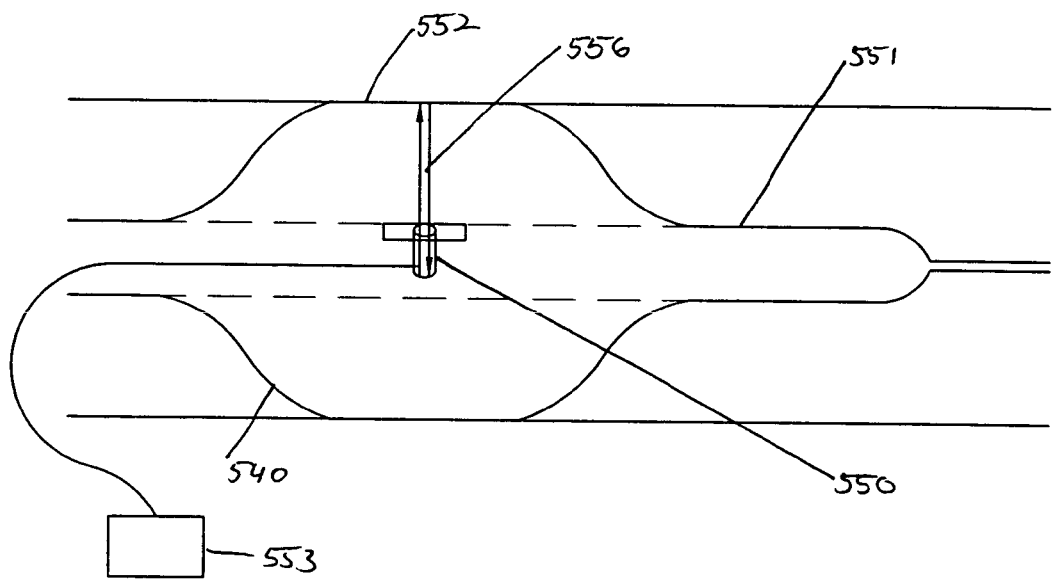
FIG. 50 shows a preferred embodiment of a minimally-invasive valve replacement sizer system, wherein the transducer emits an ultrasonic signal in a perpendicular direction to an intravascular ultrasound catheter (IVUS), which is reflected off the outer wall of the balloon and then received by the transducer and wherein the radius and diameter of the body cavity is determined by the auxiliary processor.

FIG. 50 shows a preferred embodiment, wherein a transducer (550) emits an ultrasonic signal (556) in a perpendicular direction to the IVUS catheter (551). The signal is then reflected off the outer wall (552) of the balloon (540) and received by the transducer (550). The transducer (550) then transmits the data to the auxiliary processor (553) to determine the radius and diameter of the vessel lumen. Alternatively, an infrared light may be emitted and received by the transducer (550) to determine the radius and diameter of the vessel lumen. The diameter is calculated by knowing the speed of the signal and the time it takes for the signal to be reflected off the balloon wall (552) back to the transducer (550). The known speed is multiplied by the time to determine the radius of the balloon (540). The radius may be adjusted if the transducer (550) was not located at the centermost point of the catheter.

The present invention further provides devices and methods to remove the native diseased valves prior to implantation of the replacement valve assembly. In one embodiment of the present invention, the valve removing means is provided by the replacement valve assembly. In another embodiment, the valve removing means is provided by a valve sizing device of the present invention.

Valve Assemblies with Native Valve Removing Capabiliy

The present invention further provides valve assemblies comprising native valve removing capabilities. Thus, in a preferred embodiment, a valve anchoring structure having cutting means located at the annulus base for cutting a native valve is provided. Accordingly, when passing the valve assembly comprising the valve and anchoring structure through the vessel with the anchoring structure in a collapsed state, the cutting means can be advanced against the native valve with the anchoring structure in a partially expanded state. In this manner, the anchoring structure comprising the cutting means cuts at least a portion of the native valve by deploying the cutting means, before the valve assembly is secured to the desired valve location with the anchoring structure in the expanded state.

It is one object of the present invention to provide a valve assembly of the preferred embodiment having a tissue valve and an anchoring structure, which permits implantation without surgery or with minimal surgical intervention and provides native valve removing means for removing a dysfunctional native valve, followed by valve replacement. The native valve removing means on the anchoring structure is selected from a group consisting of: a plurality of sharp edge elements, each sharp edge element having a sharp end enabling the element to cut through at least a portion of the native valve; a plurality of electrode elements, wherein radiofrequency energy is delivered to each electrode element enabling the electrode element to cut through at least a portion of the native valve, and a plurality of ultrasound transducer elements, wherein ultrasound energy is delivered to each transducer element enabling the transducer element to cut through at least a portion of the native valve.

Percutaneous implantation of a valve prosthesis is achieved according to the invention, which is characterized in that the valve anchoring structure is made from a radially collapsible and re-expandable cylindrical support means for folding and expanding together with the collapsible replacement valve for implantation in the body by means of catheterization or other minimally invasive procedure. Catheters and catheter balloon systems are well known to those of skill in the art, for example, U.S. Pat. No. 6,605,056 issued on Aug. 23, 2003.

Figure 51:
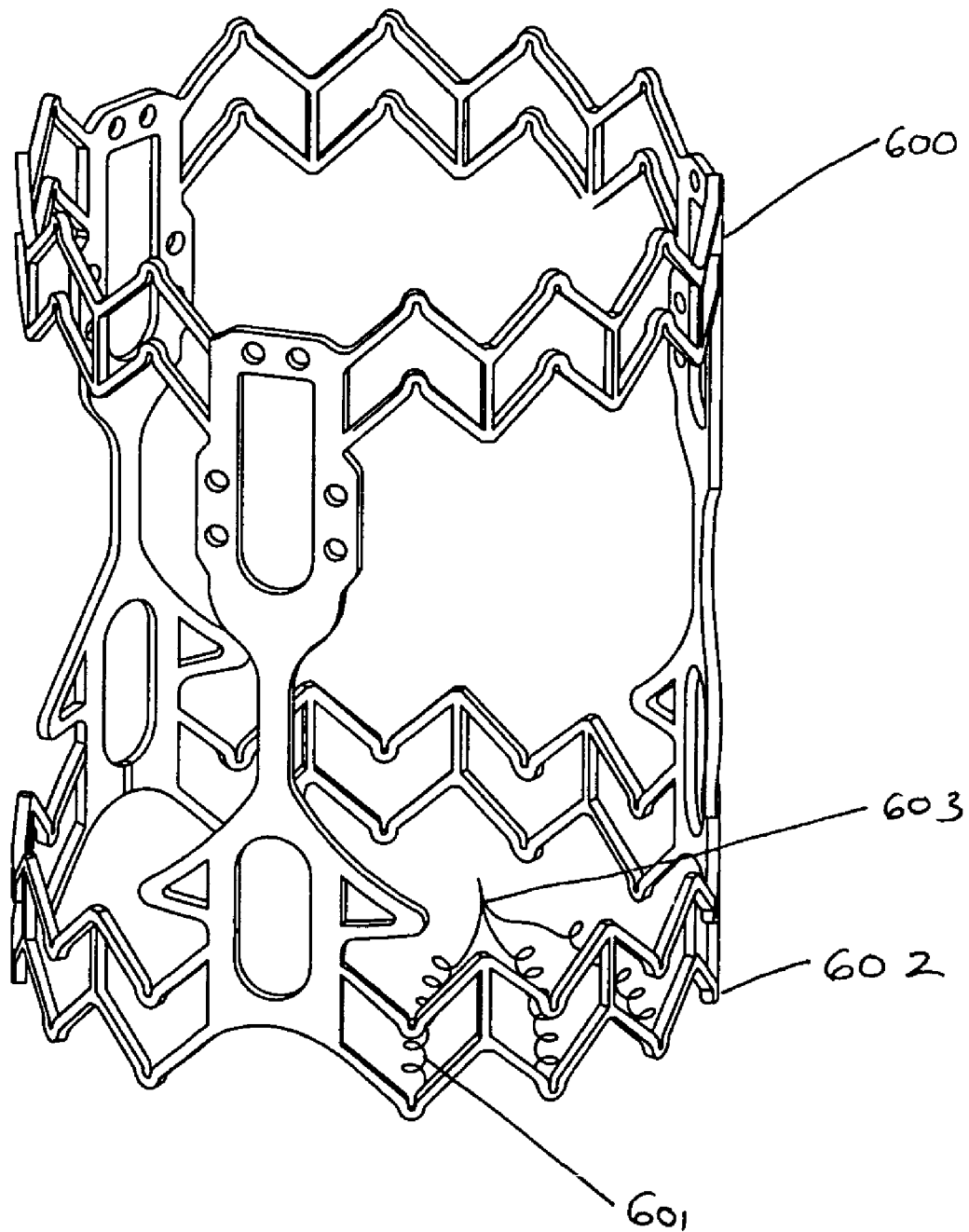
FIG. 51 shows an anchoring structure of the present invention having ultrasound cutting means.

Accordingly, in one preferred embodiment of the invention shown in FIG. 51, the anchoring structure (600) comprises at least one ultrasound transducer (601) at the distal end portion of the lower ring (602), wherein each ultrasound transducer is sized and configured with ultrasound energy as cutting means for cutting a native valve. Ultrasound energy is delivered through conductor means (603) to each transducer element (601) enabling the transducer element (601) to cut through at least a portion of the native valve. In one embodiment, the conductor (603) passes through a delivery means and is connected to an external ultrasound energy generator. The ablative ultrasound delivery means and methods are well known to one skilled in the art, for example, U.S. Pat. No. 6,241,692 issued on Jun. 5, 2001.

Figure 52:
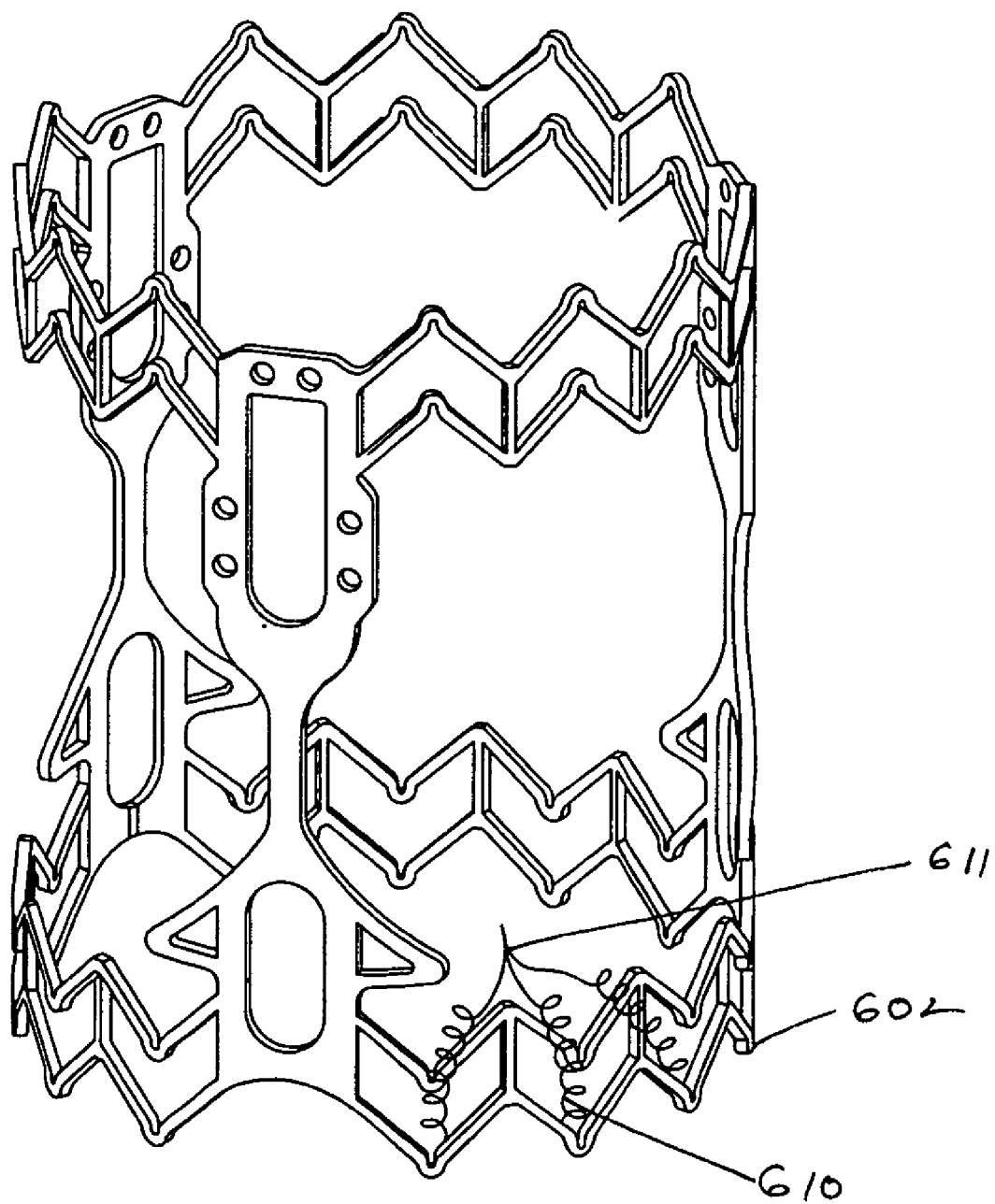
FIG. 52 shows an anchoring structure of the present invention having radiofrequency cutting means.

FIG. 52 shows another preferred embodiment of a native valve removal system comprising a valve assembly having radiofrequency cutting means. In this preferred embodiment, the anchoring structure comprises at least one radiofrequency electrode (610) at the distal end portion of the lower ring (602), wherein each radiofrequency electrode (610) is sized and configured with radiofrequency energy as cutting means for cutting a native valve. Radiofrequency energy is delivered through conductor means (611) to each electrode element(610) enabling the electrode element to cut through at least a portion of the native valve. In one embodiment, the conductor (611) passes through delivery means and is connected to an external radiofrequency energy generator. The ablative radiofrequency delivery means and methods are well known to one skilled in the art, for example, U.S. Pat. No. 6,033,402 issued on Mar. 7, 2000.

Figure 53:
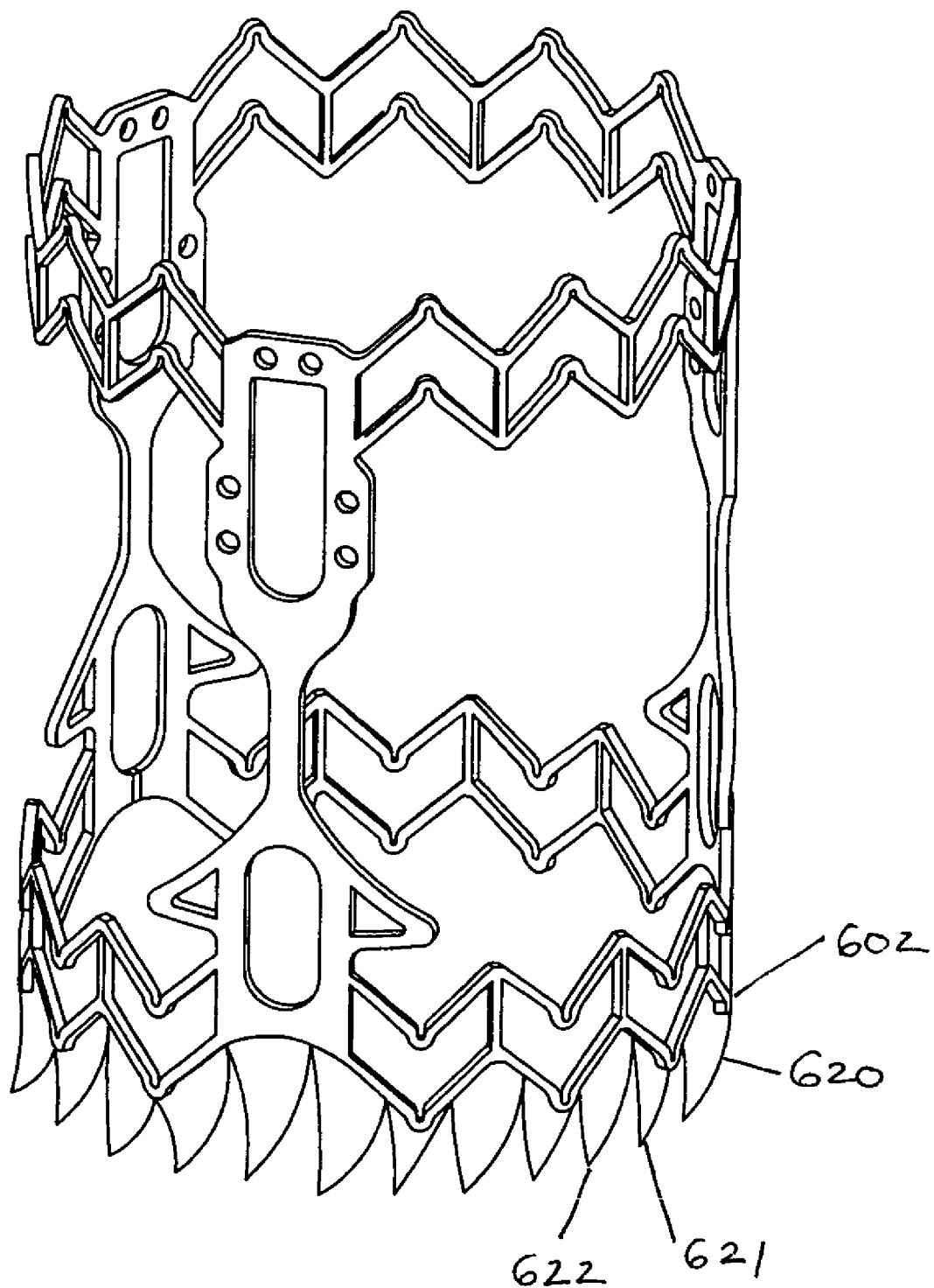
FIG. 53 shows an anchoring structure having sharp edge cutting means.

FIG. 53 shows another embodiment of an anchoring structure having sharp edge cutting means (620). In one preferred embodiment, the anchoring structure comprises a set of sharp edge cutting elements (621) at the distal end portion of the cutting means (620) of the lower ring (602) of the anchoring structure, wherein each cutting element (621) has a cutting tip (622), and wherein each cutting element (621) of the cutting means is sized and configured, optionally with radiofrequency energy, as cutting means for cutting a native valve. In one embodiment, sharp edge cutting means on the delivery apparatus is rotatable, enabling the cutting element (621) to cut through at least a portion of the native valve. Sharp edge cutting means, with optionally ablative radiofrequency delivery means and methods, are well known to one skilled in the art, for example, U.S. Pat. No. 5,980,515 issued on Nov. 9, 1999.

Figure 54:
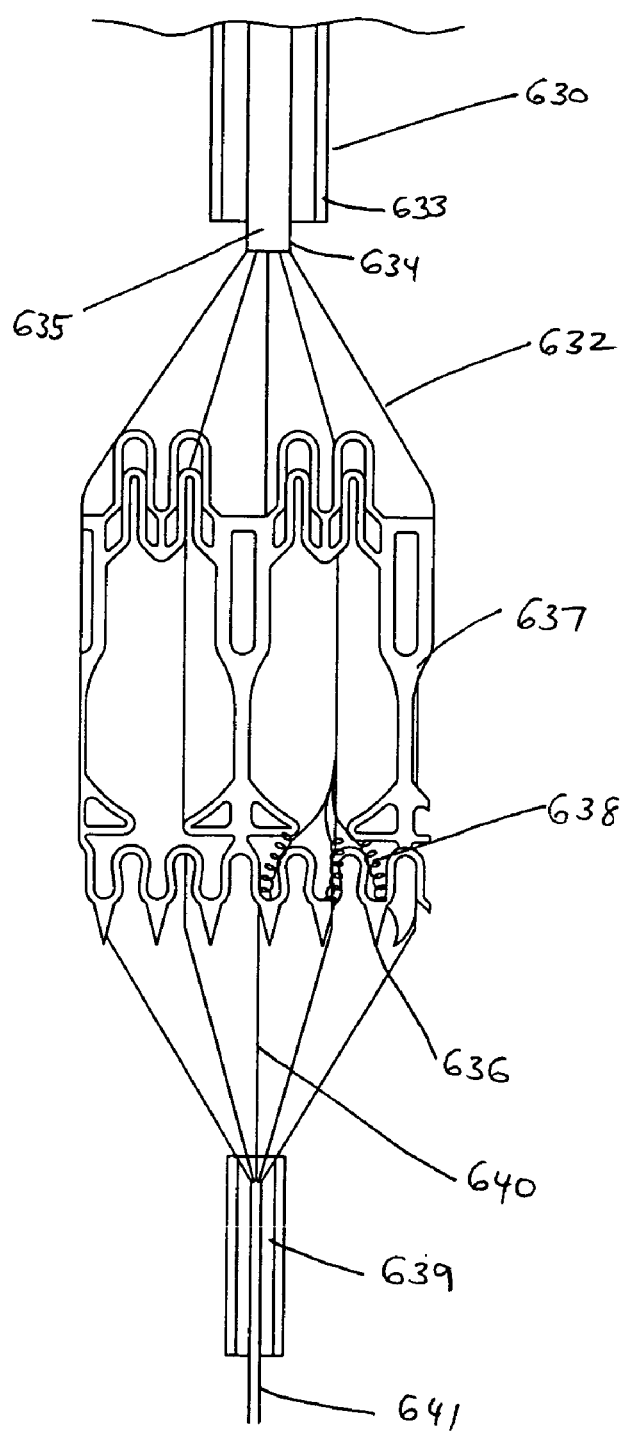
FIG. 54 is a partial view of the valve assembly with cutting means on a partially inflated balloon catheter.

FIG. 54 shows a partially inflated balloon catheter. A balloon catheter (630) is introduced in the vessel. The balloon means (632) of the balloon catheter (630) is led out of the protection cap (633) at the catheter tip (634) and is partly inflated through a fluid channel (635), which is led to the surface of the patient. In one embodiment, the balloon (632) is partially expanded and the sharp end (636) of the cutting means of the valve anchoring structure (637) is advanced to cut and remove at least a portion of the native valve. In another embodiment, the valve anchoring structure (637) comprises an ultrasound or radiofrequency cutting means (638). In one embodiment, the support structure is expanded at about 30 to 95% of full expansion for cutting the native valve. More preferably, the support structure is expanded at about 50 to 90% of the full expansion. In another embodiment, the balloon catheter (630) comprises a central channel (639) with respect to a central axial line (640) to receive a guide wire (641) which is used in a way known for viewing the introduction of the catheter through fluoroscopy.

Some aspects of the present invention provide a method of endovascularly implanting a valve through a vessel, comprising the steps of providing a collapsibly expandable valve assembly that comprises an anchoring structure according to the present invention with an annulus base and a collapsible valve connected to the anchoring structure, the collapsible valve being configured to permit blood flow in a direction and prevent blood flow in an opposite direction, the anchoring structure having cutting means located at the annulus base for cutting a native valve, passing the valve assembly through the vessel with the anchoring structure in a collapsed state, advancing the cutting means against the native valve with the anchoring structure in a partially expanded state, cutting at least a portion of the native valve by deploying the cutting means, and securing the valve assembly to the desired valve location with the anchoring structure in the expanded shape.

In operations, a method of implanting a valve assembly according to the present invention is given below: a valve assembly made of an anchoring structure of the present invention and a collapsible valve, as described above, is placed on a deflated balloon means and is compressed thereon, either manually or by use of the expansion/compression devices of the instant invention; the balloon means and the valve assembly are drawn into an insertion cover; a guide wire is inserted into a vessel through the central opening of the balloon catheter under continuous fluoroscopy; the insertion cover conveys the guide wire to a point in the channel in the immediate vicinity of the desired position of the valve assembly; the balloon means is pushed out of the protection cap and the valve assembly is positioned in the desired position if necessary by use of further imaging means to ensure accurate positioning; the balloon means is inflated partially; the valve assembly is advanced with its cutting means cutting at least a portion of the native valve; the balloon means is further inflated to position the valve at a desired site, preferably against the truncated valvular annulus; the balloon means is deflated; and the balloon means with entrapped tissue and debris inside the filter means, the guide wire, and the protection cap are drawn out and the opening in the channel, if any, wherein the valve prosthesis is inserted can be closed.

The present invention also provides for devices and methods to prevent the release of debris during removal of the native diseased valves from traveling to distant sites where such debris may cause undesirable physiological effects.

Distal Protection Assembly

As described above, removal or manipulation of diseased valves may result in dislodgment of parts of the valve or deposits formed thereon which may be carried by the fluid to other parts of the body. Thus, the present invention provides for specialized filters that capture material and debris generated during valve replacement procedures. The distal protection devices of the present invention are also effective in trapping material that may be released during other percutaneous interventional procedures, such as balloon angioplasty or stenting procedures by providing a temporary valve and filter in the same device.

Figure 55A:
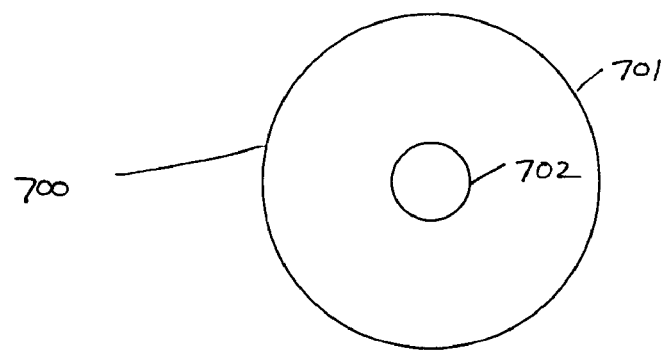
FIGS. 55A–C show a temporary two-way valve for distal protection.
Figure 55B:
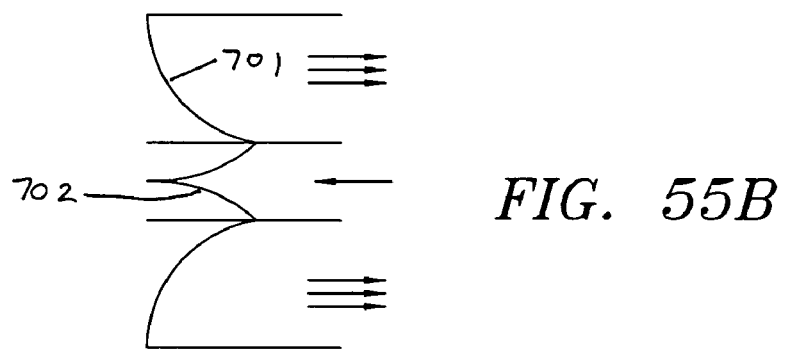
Figure 55C:
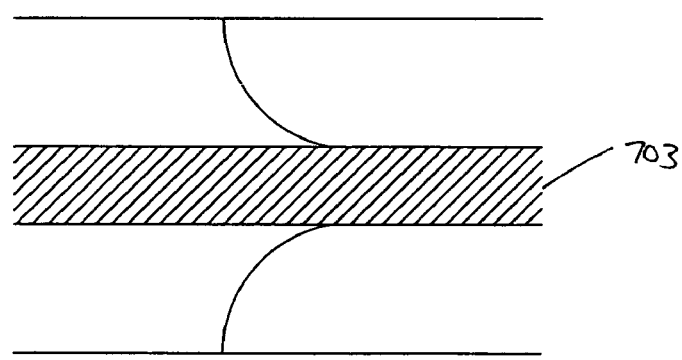

In one preferred embodiment, shown in FIGS. 55A and B, the present invention provides for a temporary valve (700), which may be deployed at a desired location in a collapsed state and then expanded and secured to the walls of the passageway. The temporary valve (700) comprises two concentric one-way valves, an outer valve (701) and an inner valve (702) disposed within the outer valve (701), that open in opposite directions as shown in FIG. 55B. The outer valve (701) opens in response to positive fluid flow pressure, thereby regulating blood flow in substantially one direction. The inner valve (702) opens in the opposite direction of the outer valve (701) to facilitate the insertion of catheter based equipment (703) as shown in FIG. 55C and functions as a seal through which such equipment may be passed. The pressure required to open the individual valves may be manipulated to facilitate positive fluid flow, while precluding or minimizing retrograde flow that might otherwise occur as a result of back flow pressure. Hence, it is contemplated that the inner valve (702) be configured or constructed to open with relatively more pressure than that required to open the outer valve.

The outer (701) and inner valves (702) of the temporary valve (700) may be coupled together by radial support members. In one embodiment, the radial support members couple the inner surface of the outer valve to the outer surface of the inner valve. The length of the radial support means depends upon the dimension of the blood vessel or body cavity within which the temporary valve is to be deployed.

The temporary valve may be constructed from material that is capable of self-expanding the temporary valve, once it is deployed from the collapsed state at the desired location. Once expanded, catheter based equipment required for the particular surgical procedure may be passed through and movably operated in relation to the temporary valve.

In another embodiment of the present invention, the temporary valve may be combined with a filter that extends distally from the temporary valve to capture debris material. In this embodiment, the temporary valve-filter device is preferably configured such that the open proximal end is secured to the temporary valve and the closed distal end comprises an opening or a third valve to facilitate the passage of the catheter equipment through the distal end of the bag and out of the temporary valve. Additional valves may also be positioned in the filter to coincide with one or more branching arteries.

In yet another preferred embodiment of the present invention, the temporary valve-filter device may include one or more traps within the filter bag to trap debris material within the bag to reduce the likelihood of debris material leaving the filter when the catheter equipment is being passed through the filter bag. The filter traps may be comprised of one or more valves disposed within the filter bag that are configured to open with retrograde pressure. Alternatively, the traps may be comprised of flaps that extend inwardly from the perimeter of the bag to create a cupping effect that traps particulate matter and directs it outwardly toward the perimeter of the filter bag. The filter traps may be constructed of material that is capable of facilitating and filtering antegrade fluid flow, while retaining the debris material within the filter bag.

The valve-filter assembly previously described may also incorporate multiple valves. In this arrangement, debris may be better and better entrapped, and thus reduces the chance of debris coming out of the valve-filter assembly. The present invention is particularly useful while performing an interventional procedure in vital arteries, such as the carotid arteries and the aorta, in which critical downstream blood vessels can become blocked with debris material.

One benefit of the current invention is that it provides fast, simple, and quick deployment. One may deploy both the filter and temporary valve simultaneously. The valve-filter assembly may also include a cannulation system at the downstream end of the filter to remove particles and debris. The valve-filter assembly may also include a grinder for cutting up or reducing the size of the debris. This debris, in turn, may be removed by a cannulation system or be allowed to remain in the filter.

The valve-filter assembly is well-suited for use in minimally invasive surgery where the valve-filter may be placed in the aorta between the aortic valve and the innominate branch or the braciocephalic branch. In such a configuration, the valve-filter may be put in place before the start of surgery and function as a valve. The valve-filter may further collect debris and particles during removal and clean up of the old valve. The valve-filter may also stay in place while the new valve is put in place and until the end of the procedure to function as protection and as a valve. A vascular filter system is well known to one skilled in the art, for example, U.S. Pat. No. 6,485,501 issued on Nov. 26, 2002.

In all of the embodiments described above, the invention may be part of a catheter. The invention may also be assembled onto a separate catheter. The valve-filter may also be part of a non-catheter device, placed directly into a blood vessel or other lumen. In both the catheter and non-catheter embodiments, the valve-filter may be introduced into the body by the ways described in the following non-inclusive list: femoral artery, femoral vein, carotid artery, jugular vein, mouth, nose, urethra, vagina, brachial artery, subclavian vein, open sternotomies, partial sternotomies, and other places in the arterial and venous system.

Furthermore, in all of the embodiments described above, the filter mesh of the valve-filter may be of any size and shape required to trap all of the material while still providing sufficient surface area for providing satisfactory flows during the use of the filter. The filter may be a sheet or bag of different mesh sizes. In a preferred embodiment, the mesh size is optimized taking the following factors into consideration: flow conditions, application site, size of filter bag, rate of clotting, etc.

Radiopaque markers and/or sonoreflective markers, may be located on the catheter and/or the valve-filter assembly. An embodiment of the valve-filter catheter is described having an aortic transillumination system for locating and monitoring the position and deployment state of the catheter and the valve-filter assembly without fluoroscopy.

Additionally, visualization techniques including transcranial Doppler ultrasonography, transesophageal echocardiograpy, transthoracic echocardiography, epicardiac echocardiography, and transcutaneous or intravascular ultrasoneography in conjunction with the procedure may be used to ensure effective filtration.

Alternatively, or additionally, the material of the filter screen in each embodiment of the filter catheter may be made of or coated with an adherent material or substance to capture or hold embolic debris which comes into contact with the filter screen within the valve-filter assembly. Suitable adherent materials include, but are not limited to, known biocompatible adhesives and bioadhesive materials or substances, which are hemocompatible and non-thrombogenic. Such material are known to those having ordinary skill in the art and are described in, among other references, U.S. Pat. Nos. 4,768,523, 5,055,046, 5,066,709, 5,197,973, 5,225,196, 5,374,431, 5,578,310, 5,645,062, 5,648,167, 5,651,982, and 5,665,477. In one particularly preferred embodiment, only the upstream side of the elements of the filter screen are coated with the adherent material to capture the embolic material which comes in contact with the upstream side of the filter screen after entering the filter assembly. Other bioactive substances, for example, heparin or thrombolytic agents, may be impregnated into or coated on the surface of the filter screen material or incorporated into an adhesive coating.

In a preferred method, blood is filtered during cardiac surgery, in particular during percutaneous valve surgery, to protect a patient from embolization. In this method, the valve-filter is positioned in the aorta between the aortic valve and the inominate branch, where it filters blood before it reaches the carotid arteries, brachiocephalic trunk, and left subclavian artery. The valve contains the embolic material and foreign matter dislodged during the surgery and also provides a temporary valve for use during valve surgery. Such a method may be utilized both on and off pump. Such a method may also be utilized for aortic, mitral, and pulmonary valve surgery and repair.

Although this invention has been exemplified for purposes of illustration and description by reference to certain specific embodiments, it will be apparent to those skilled in the art that various modifications and alterations of the illustrated examples are possible. Numerous modifications, alterations, alternate embodiments, and alternate materials may be contemplated by those skilled in the art and may be utilized in accomplishing the present invention. Any such changes which derive directly from the teachings herein, and which do not depart from the spirit and scope of the invention, are deemed to be covered by this invention.

The invention claimed is:

1. A valve assembly comprising:
    a replacement valve having a scalloped inflow annulus having a scalloped edge, an outflow annulus, and a plurality of leaflets between said scalloped inflow annulus and said outflow annulus; and
    an expandable and collapsible stent anchoring structure composed of a shape memory metal alloy material having an undulating inflow rim having a curvature that coextends with the scalloped edge of the inflow annulus and an outflow rim connected by support posts and adopted to support the replacement valve and the outflow rim being longitudinally displaced from the replacement valve leaflets, the anchoring structure inflow rim having an undulating configuration to support the scalloped inflow annulus of the replacement valve;
    said anchoring structure being dimensioned to extend longitudinally from an attachment location near the inflow annulus of a native valve sinus to an attachment location near the outflow annulus of a native valve sinus.

2. The valve assembly of claim 1, wherein said valve has three leaflets.

3. The valve assembly of claim 1, wherein said support posts are configured to coincide longitudinally with a native valve sinus commissural posts.

4. The valve assembly of claim 1, wherein said outflow rim comprises a plurality of rings.

5. The valve assembly of claim 4, wherein said plurality of rings are configured in an undulating pattern.

6. The valve assembly of claim 5, wherein said plurality of rings are substantially parallel to each other.

7. The valve assembly of claim 6, wherein said plurality of rings are connected by a vertical element.

8. The valve assembly of claim 1, wherein said inflow rim comprises a plurality of rings.

9. The valve assembly of claim 8, wherein said plurality of rings are configured in an undulating pattern.

10. The valve assembly of claim 9, wherein said plurality of rings are substantially parallel to each other.

11. The valve assembly of claim 10, wherein said plurality of rings are connected by a vertical element.

12. The valve assembly of claim 1, wherein said inflow rim comprises one ring.

13. The valve assembly of claim 12, wherein said ring is configured in an undulating pattern.

14. The valve assembly of claim 1, wherein said anchoring structure is collapsible to at least 50% of its expanded diameter.

15. A valve assembly comprising:
    a replacement valve having a scalloped inflow annulus, an outflow annulus, and a plurality of leaflets between said scalloped inflow annulus and said outflow annulus; and
    an expandable and collapsible stent anchoring structure composed of a shape memory metal alloy material having an inflow rim and an outflow rim connected by support posts and adopted to support the replacement valve and the outflow rim being longitudinally displaced from the replacement valve leaflets, the anchoring structure inflow rim having an undulating configuration to support the scalloped inflow annulus of the replacement valve;
    said anchoring structure being dimensioned to extend longitudinally from an attachment location near the inflow annulus of a native valve sinus to an attachment location near the outflow annulus of a native valve sinus
    wherein said support posts are configured to coincide longitudinally with a native valve sinus commissural posts and wherein said support posts comprise axially extending slots toward the outflow rim for the attachment of a valve's commissural tabs.

16. The valve assembly of claim 15, wherein said support posts comprise triangular shaped elements at the inflow rim.

17. The valve assembly of claim 16, wherein said support posts further comprise a plurality of bores on either side of said slots to facilitate attachment of the commissural tabs.

* * * * *